United States Patent
Darvish et al.

(10) Patent No.: US 8,321,013 B2
(45) Date of Patent: Nov. 27, 2012

(54) ELECTRICAL MUSCLE CONTROLLER AND PACING WITH HEMODYNAMIC ENHANCEMENT

(75) Inventors: Nissim Darvish, Hof HaCamel (IL); Bella Felsen, Haifa (IL); Itzhak Shemer, Haifa (IL); Judith Kornfeld, Zikhron-Yaakov (IL); Shlomo Ben-Haim, Orangeburg, NY (US); Maier Fenster, Petach-Tikva (IL); Yuval Mika, Closter, NJ (US)

(73) Assignee: Impulse Dynamics, N.V., Curacao (AN)

( * ) Notice: Subject to any disclaimer, the term of this patent is extended or adjusted under 35 U.S.C. 154(b) by 675 days.

(21) Appl. No.: 11/933,168

(22) Filed: Oct. 31, 2007

(65) Prior Publication Data
US 2008/0140142 A1 Jun. 12, 2008

Related U.S. Application Data

(63) Continuation-in-part of application No. 09/720,639, filed as application No. PCT/IL99/00392 on Jul. 18, 1999, now Pat. No. 7,460,907, application No. 11/933,168, which is a continuation-in-part of application No. 11/550,560, filed on Oct. 18, 2006, which is a continuation of application No. 10/866,213, filed on Jun. 10, 2004, now Pat. No. 7,167,748, which is a continuation of application No. 10/001,710, filed on Oct. 31, 2001, now Pat. No. 7,062,318, which is a continuation of application No. 09/723,989, filed on Nov. 28, 2000, now Pat. No. 6,330,476, which is a continuation of application No. 09/101,723, filed as application No. PCT/IL97/00012 on Jan. 8, 1997, now Pat. No. 6,317,631, which is a continuation of application No. 08/595,365, filed on Feb. 1, 1996.

(60) Provisional application No. 60/009,769, filed on Jan. 11, 1996, provisional application No. 60/011,117, filed on Feb. 5, 1996, provisional application No. 60/026,392, filed on Sep. 16, 1996.

(30) Foreign Application Priority Data

| Jan. 8, 1996 | (IL) | 116699 |
| Sep. 17, 1996 | (IL) | 119261 |
| Jul. 20, 1998 | (IL) | 125424 |

(51) Int. Cl.
*A61N 1/00* (2006.01)
(52) U.S. Cl. .................... 607/9; 607/2; 607/5
(58) Field of Classification Search ................ 607/2, 5, 607/9
See application file for complete search history.

(56) References Cited

U.S. PATENT DOCUMENTS
1,918,386 A 7/1933 Esau
(Continued)

FOREIGN PATENT DOCUMENTS
EP 148687 7/1985
(Continued)

OTHER PUBLICATIONS
Advisory Action Before the Filing of an Appeal Brief Dated Mar. 22, 2012 From the US Patent and Trademark Office Re. U.S. Appl. No. 11/886,154.
(Continued)

*Primary Examiner* — Nicole F Lavert
(74) *Attorney, Agent, or Firm* — William H. Dippert; Eckert Seamans Cherin & Mellott, LLC

(57) ABSTRACT

A method of modifying the force of contraction of at least a portion of a heart chamber is provided. A non-excitatory electric field of given duration is applied, at a delay after an activation of the heart, which increase the force of contraction by at least 5%. Apparatus is also provided for pacing with hemodynamic improvement. Circuitry applies an extended pacing signal to electrodes to pace the heart, the extended pacing signal having an overall duration greater than 8 ms from a time of initiation of application of that portion of the signal that initiates action potential propagation. The signal includes a train of biphasic pulses having pulse durations of at least 1 ms, and the signal has an amplitude that is at least three times as great as a threshold for pacing the heart and that is sufficient neither for cardioversion nor for defibrillation. Other embodiments are also described.

34 Claims, 34 Drawing Sheets

U.S. PATENT DOCUMENTS

| | | |
|---|---|---|
| 3,211,154 A | 10/1965 | Becker et al. |
| 3,541,390 A | 11/1970 | Jahnke |
| 3,572,345 A | 3/1971 | Auphan |
| 3,587,567 A | 6/1971 | Schiff |
| 3,651,805 A | 3/1972 | Breiling |
| 3,651,806 A | 3/1972 | Hirshberg |
| 3,796,221 A | 3/1974 | Hagfors |
| 3,911,930 A | 10/1975 | Hagfors et al. |
| 3,933,147 A | 1/1976 | Du Vall et al. |
| 3,942,536 A | 3/1976 | Mirowski et al. |
| 3,944,740 A | 3/1976 | Murase et al. |
| 3,952,750 A | 4/1976 | Mirowski et al. |
| 4,030,509 A | 6/1977 | Hellman et al. |
| 4,106,494 A | 8/1978 | McEachern |
| 4,164,216 A | 8/1979 | Person |
| 4,168,711 A | 9/1979 | Cannon, III et al. |
| 4,184,493 A | 1/1980 | Langer et al. |
| 4,202,340 A | 5/1980 | Langer et al. |
| 4,223,678 A | 9/1980 | Langer et al. |
| 4,237,895 A | 12/1980 | Johnson |
| 4,273,114 A | 6/1981 | Barkalow et al. |
| 4,293,734 A | 10/1981 | Pepper, Jr. |
| 4,312,354 A | 1/1982 | Walters |
| 4,315,503 A | 2/1982 | Ryaby et al. |
| 4,316,472 A | 2/1982 | Mirowski et al. |
| 4,337,776 A | 7/1982 | Daly et al. |
| 4,369,791 A | 1/1983 | Friedman |
| 4,384,585 A | 5/1983 | Zipes |
| 4,387,717 A | 6/1983 | Brownlee et al. |
| 4,403,614 A | 9/1983 | Engle et al. |
| 4,406,288 A | 9/1983 | Horwinski et al. |
| 4,407,288 A | 10/1983 | Langer et al. |
| 4,411,268 A | 10/1983 | Cox |
| 4,428,366 A | 1/1984 | Findl et al. |
| 4,440,172 A | 4/1984 | Langer |
| 4,506,680 A | 3/1985 | Stokes |
| 4,537,195 A | 8/1985 | McDonnell |
| 4,537,203 A | 8/1985 | Machida |
| 4,543,738 A | 10/1985 | Mower |
| 4,543,956 A | 10/1985 | Herscovici |
| 4,550,221 A | 10/1985 | Mabusth |
| 4,554,922 A | 11/1985 | Prystowsky |
| 4,554,992 A | 11/1985 | Kassai |
| 4,559,946 A | 12/1985 | Mower |
| 4,559,947 A | 12/1985 | Renger et al. |
| 4,566,456 A | 1/1986 | Koning |
| 4,572,191 A | 2/1986 | Mirowski et al. |
| 4,628,934 A | 12/1986 | Pohndorf et al. |
| 4,637,397 A | 1/1987 | Jones et al. |
| 4,639,720 A | 1/1987 | Rympalski et al. |
| 4,651,716 A | 3/1987 | Forester |
| 4,665,609 A | 5/1987 | Henry et al. |
| 4,674,508 A | 6/1987 | DeCote |
| 4,679,572 A | 7/1987 | Baker, Jr. |
| 4,686,332 A | 8/1987 | Greanias et al. |
| 4,690,155 A | 9/1987 | Hess |
| 4,693,253 A | 9/1987 | Adams |
| 4,708,145 A | 11/1987 | Tacker et al. |
| 4,717,581 A | 1/1988 | Robblee |
| 4,726,279 A | 2/1988 | Kepler et al. |
| 4,726,379 A | 2/1988 | Altman et al. |
| 4,765,341 A | 8/1988 | Mower et al. |
| 4,807,632 A | 2/1989 | Liess et al. |
| 4,830,006 A | 5/1989 | Haluska et al. |
| 4,834,100 A | 5/1989 | Charms |
| 4,850,959 A | 7/1989 | Findl |
| 4,870,974 A | 10/1989 | Wang |
| 4,878,553 A | 11/1989 | Yamanami et al. |
| 4,884,576 A | 12/1989 | Alt |
| 4,914,624 A | 4/1990 | Dunthorn et al. |
| 4,928,688 A | 5/1990 | Mower |
| 4,967,749 A | 11/1990 | Cohen |
| 4,971,058 A | 11/1990 | Pless et al. |
| 4,979,507 A | 12/1990 | Heinz et al. |
| 4,988,837 A | 1/1991 | Murakami et al. |
| 4,996,984 A | 3/1991 | Sweeney |
| 4,998,531 A | 3/1991 | Bocchi et al. |
| 4,998,532 A | 3/1991 | Griffith |
| 5,002,052 A | 3/1991 | Haluska et al. |
| 5,003,976 A | 4/1991 | Alt |
| 5,018,522 A | 5/1991 | Mehra |
| 5,020,544 A | 6/1991 | Dahl et al. |
| 5,022,396 A | 6/1991 | Watanabe |
| 5,026,397 A | 6/1991 | Aoki et al. |
| 5,041,107 A | 8/1991 | Heil, Jr. |
| 5,044,375 A | 9/1991 | Bach, Jr. et al. |
| 5,048,522 A | 9/1991 | Petrofsky |
| 5,063,929 A | 11/1991 | Bartelt et al. |
| 5,083,564 A | 1/1992 | Scherlag |
| 5,085,218 A | 2/1992 | Heil et al. |
| 5,087,243 A | 2/1992 | Avitall |
| 5,097,832 A | 3/1992 | Buchanan |
| 5,097,833 A | 3/1992 | Campos |
| 5,101,814 A | 4/1992 | Palti |
| 5,107,834 A | 4/1992 | Ideker et al. |
| 5,111,814 A * | 5/1992 | Goldfarb ........................ 607/48 |
| 5,111,815 A | 5/1992 | Mower |
| 5,129,394 A | 7/1992 | Mehra |
| 5,133,354 A | 7/1992 | Kallok |
| 5,137,021 A | 8/1992 | Wayne et al. |
| 5,144,554 A | 9/1992 | Zhang et al. |
| 5,154,501 A | 10/1992 | Svenson |
| 5,156,147 A | 10/1992 | Warren et al. |
| 5,156,149 A | 10/1992 | Hudrlik |
| 5,161,527 A | 11/1992 | Nappholz |
| 5,163,427 A | 11/1992 | Keimel |
| 5,163,428 A | 11/1992 | Pless |
| 5,172,690 A | 12/1992 | Nappholz et al. |
| 5,172,699 A | 12/1992 | Svenson et al. |
| 5,174,286 A | 12/1992 | Chirife |
| 5,184,616 A * | 2/1993 | Weiss ................. 607/4 |
| 5,184,620 A | 2/1993 | Cudahy et al. |
| 5,185,620 A | 2/1993 | Cooper |
| 5,188,104 A | 2/1993 | Wernicke et al. |
| 5,188,106 A | 2/1993 | Nappholz et al. |
| 5,190,041 A | 3/1993 | Palti |
| 5,199,428 A | 4/1993 | Obel et al. |
| 5,205,284 A | 4/1993 | Freeman |
| 5,213,098 A | 5/1993 | Bennett et al. |
| 5,231,381 A | 7/1993 | Duwaer |
| 5,233,985 A | 8/1993 | Hudrlik |
| 5,236,413 A | 8/1993 | Feiring |
| 5,243,980 A | 9/1993 | Mehra et al. |
| 5,267,560 A | 12/1993 | Cohen |
| 5,281,219 A | 1/1994 | Kallok |
| 5,282,785 A | 2/1994 | Shapland et al. |
| 5,284,491 A | 2/1994 | Sutton et al. |
| 5,286,254 A | 2/1994 | Shapland et al. |
| 5,292,344 A | 3/1994 | Douglas |
| 5,305,745 A | 4/1994 | Zacouto |
| 5,318,591 A * | 6/1994 | Causey et al. .................... 607/5 |
| 5,320,642 A | 6/1994 | Scherlag |
| 5,320,643 A | 6/1994 | Roline et al. |
| 5,324,327 A | 6/1994 | Cohen |
| 5,325,856 A * | 7/1994 | Nitzsche et al. ............. 600/516 |
| 5,327,887 A | 7/1994 | Nowakowski |
| 5,346,506 A | 9/1994 | Mower et al. |
| 5,350,403 A | 9/1994 | Stroetmann et al. |
| 5,353,800 A | 10/1994 | Pohndorf |
| 5,365,461 A | 11/1994 | Stein et al. |
| 5,366,485 A | 11/1994 | Kroll et al. |
| 5,366,486 A | 11/1994 | Zipes et al. |
| 5,368,040 A | 11/1994 | Carney |
| 5,370,665 A | 12/1994 | Hudrlik |
| 5,374,787 A | 12/1994 | Miller et al. |
| 5,381,160 A | 1/1995 | Landmeier |
| 5,386,835 A | 2/1995 | Elphick et al. |
| 5,386,837 A | 2/1995 | Sterzer |
| 5,387,419 A | 2/1995 | Levy |
| 5,391,192 A | 2/1995 | Lu |
| 5,391,199 A | 2/1995 | Ben-Haim |
| 5,397,344 A | 3/1995 | Garfield et al. |
| 5,398,683 A | 3/1995 | Edwards |
| 5,402,151 A | 3/1995 | Duwaer |
| 5,411,531 A | 5/1995 | Hill et al. |
| 5,415,629 A | 5/1995 | Henley |
| 5,417,717 A | 5/1995 | Salo et al. |

| Patent No. | Date | Name |
|---|---|---|
| 5,419,763 A | 5/1995 | Hildebrand |
| 5,423,872 A | 6/1995 | Cigaina |
| 5,425,363 A | 6/1995 | Wang |
| 5,431,682 A | 7/1995 | Hedberg |
| 5,431,688 A | 7/1995 | Freeman |
| 5,431,693 A | 7/1995 | Schroeppel |
| 5,433,730 A | 7/1995 | Alt |
| 5,443,485 A | 8/1995 | Housworth |
| 5,443,489 A | 8/1995 | Ben-Haim |
| 5,445,609 A | 8/1995 | Lattin et al. |
| 5,447,520 A | 9/1995 | Spano |
| 5,447,525 A | 9/1995 | Powell et al. |
| 5,447,526 A | 9/1995 | Karsdon |
| 5,458,568 A | 10/1995 | Racchini et al. |
| 5,464,020 A | 11/1995 | Lerner |
| 5,464,429 A | 11/1995 | Hedberg et al. |
| 5,468,254 A | 11/1995 | Hahn |
| 5,472,453 A | 12/1995 | Alt |
| 5,476,484 A | 12/1995 | Hedberg |
| 5,476,485 A | 12/1995 | Weinberg et al. |
| 5,476,487 A | 12/1995 | Sholder |
| 5,476,497 A | 12/1995 | Mower |
| 5,482,052 A | 1/1996 | Lerner |
| 5,489,293 A | 2/1996 | Pless et al. |
| 5,495,077 A | 2/1996 | Miller et al. |
| 5,499,971 A | 3/1996 | Shapland et al. |
| 5,501,662 A | 3/1996 | Hofman |
| 5,505,700 A | 4/1996 | Leone et al. |
| 5,510,813 A | 4/1996 | Makinwa et al. |
| 5,514,162 A | 5/1996 | Bornzin et al. |
| 5,520,642 A | 5/1996 | Bigagli et al. |
| 5,522,853 A | 6/1996 | Kroll |
| 5,527,345 A * | 6/1996 | Infinger ............................ 607/4 |
| 5,528,002 A | 6/1996 | Katabami |
| 5,531,764 A | 7/1996 | Adams et al. |
| 5,534,015 A | 7/1996 | Kroll et al. |
| 5,540,722 A | 7/1996 | Clare |
| 5,540,730 A | 7/1996 | Terry, Jr. et al. |
| 5,540,734 A | 7/1996 | Zabara |
| 5,543,589 A | 8/1996 | Buchana et al. |
| 5,549,646 A | 8/1996 | Katz et al. |
| 5,556,421 A | 9/1996 | Prutchi |
| 5,556,760 A | 9/1996 | Nakamura et al. |
| 5,558,640 A | 9/1996 | Pfeiler et al. |
| 5,561,165 A | 10/1996 | Lautt et al. |
| 5,562,708 A | 10/1996 | Combs et al. |
| 5,565,632 A | 10/1996 | Ogawa |
| 5,568,809 A | 10/1996 | Ben-Haim |
| 5,571,143 A | 11/1996 | Hoegnelid et al. |
| 5,571,997 A | 11/1996 | Gray et al. |
| 5,578,061 A | 11/1996 | Stroetmann et al. |
| 5,584,803 A | 12/1996 | Stevens |
| 5,584,868 A | 12/1996 | Salo et al. |
| 5,587,200 A | 12/1996 | Lorenz |
| 5,589,856 A | 12/1996 | Stein et al. |
| 5,601,609 A | 2/1997 | Duncan |
| 5,601,611 A | 2/1997 | Fayram et al. |
| 5,620,468 A | 4/1997 | Mongeon et al. |
| 5,622,687 A | 4/1997 | Krishnan et al. |
| 5,626,622 A | 5/1997 | Cooper |
| 5,632,267 A | 5/1997 | Hognelid et al. |
| 5,634,895 A | 6/1997 | Igo et al. |
| 5,634,899 A | 6/1997 | Shapland et al. |
| 5,649,966 A | 7/1997 | Noren et al. |
| 5,651,378 A | 7/1997 | Matheny |
| 5,654,030 A | 8/1997 | Munshi et al. |
| 5,662,687 A | 9/1997 | Hedberg et al. |
| 5,670,755 A | 9/1997 | Kwon |
| 5,674,251 A | 10/1997 | Combs et al. |
| 5,674,259 A | 10/1997 | Gray |
| 5,683,429 A | 11/1997 | Mehra |
| 5,683,431 A | 11/1997 | Wang |
| 5,687,734 A | 11/1997 | Dempsey et al. |
| 5,690,691 A | 11/1997 | Chen et al. |
| 5,697,953 A | 12/1997 | Kroll et al. |
| 5,713,924 A | 2/1998 | Min et al. |
| 5,713,929 A | 2/1998 | Hess et al. |
| 5,713,935 A | 2/1998 | Prutchi et al. |
| 5,720,768 A | 2/1998 | Verboven-Nelissen |
| 5,735,876 A | 4/1998 | Kroll et al. |
| 5,738,096 A | 4/1998 | Ben Haim |
| 5,738,105 A | 4/1998 | Kroll |
| 5,741,791 A | 4/1998 | Olsen |
| 5,749,906 A | 5/1998 | Kieval et al. |
| 5,755,740 A | 5/1998 | Nappholz |
| 5,777,607 A | 7/1998 | Koolen |
| 5,779,661 A | 7/1998 | Stephen et al. |
| 5,782,876 A | 7/1998 | Flammang |
| 5,782,881 A | 7/1998 | Lu et al. |
| 5,783,951 A | 7/1998 | Inoue et al. |
| 5,790,106 A | 8/1998 | Hirano et al. |
| 5,790,107 A | 8/1998 | Kasser et al. |
| 5,792,198 A | 8/1998 | Nappholz |
| 5,792,208 A | 8/1998 | Gray |
| 5,797,967 A | 8/1998 | KenKnight |
| 5,800,464 A | 9/1998 | Kieval |
| 5,807,234 A | 9/1998 | Bui et al. |
| 5,807,306 A | 9/1998 | Shapland et al. |
| 5,814,079 A | 9/1998 | Kieval |
| 5,825,352 A | 10/1998 | Bisset et al. |
| 5,841,078 A | 11/1998 | Miller et al. |
| 5,854,881 A | 12/1998 | Yoshida et al. |
| 5,861,014 A | 1/1999 | Familoni |
| 5,865,787 A | 2/1999 | Shapland et al. |
| 5,871,506 A | 2/1999 | Mower |
| 5,906,607 A | 5/1999 | Taylor et al. |
| 5,911,223 A | 6/1999 | Weaver et al. |
| 5,913,876 A | 6/1999 | Taylor et al. |
| 5,914,465 A | 6/1999 | Allen et al. |
| 5,919,216 A | 7/1999 | Houben et al. |
| 5,920,309 A | 7/1999 | Bisset et al. |
| 5,927,284 A | 7/1999 | Borst et al. |
| 5,954,761 A | 9/1999 | Machek et al. |
| 5,956,020 A | 9/1999 | D'Amico et al. |
| 5,962,246 A | 10/1999 | Ladner et al. |
| 5,991,649 A | 11/1999 | Garfield et al. |
| 5,995,872 A | 11/1999 | Bourgeois |
| 6,002,594 A | 12/1999 | Ledin et al. |
| 6,006,134 A | 12/1999 | Hill et al. |
| 6,023,640 A | 2/2000 | Ross |
| 6,026,326 A | 2/2000 | Bardy |
| 6,032,074 A | 2/2000 | Collins |
| 6,032,672 A | 3/2000 | Taylor |
| 6,037,882 A | 3/2000 | Levy |
| 6,041,252 A | 3/2000 | Walker et al. |
| 6,057,374 A | 5/2000 | Huntington et al. |
| 6,066,163 A | 5/2000 | John |
| 6,071,305 A | 6/2000 | Brown et al. |
| 6,075,520 A | 6/2000 | Inoue et al. |
| 6,083,249 A | 7/2000 | Familoni |
| 6,086,582 A | 7/2000 | Altman et al. |
| 6,093,167 A | 7/2000 | Houben et al. |
| 6,122,536 A | 9/2000 | Sun et al. |
| 6,128,007 A | 10/2000 | Seybold et al. |
| 6,133,906 A | 10/2000 | Geaghan |
| 6,135,978 A | 10/2000 | Houben et al. |
| 6,136,019 A | 10/2000 | Mower |
| 6,141,586 A | 10/2000 | Mower |
| 6,141,587 A | 10/2000 | Mower |
| 6,151,586 A | 11/2000 | Brown |
| 6,178,351 B1 | 1/2001 | Mower |
| 6,233,484 B1 | 5/2001 | Ben-Haim et al. |
| 6,233,487 B1 | 5/2001 | Mika et al. |
| 6,236,887 B1 | 5/2001 | Ben-Haim et al. |
| 6,239,389 B1 | 5/2001 | Allen et al. |
| 6,243,607 B1 | 6/2001 | Mintchev et al. |
| 6,261,280 B1 | 7/2001 | Houben et al. |
| 6,278,443 B1 | 8/2001 | Amro et al. |
| 6,285,906 B1 | 9/2001 | Ben-Haim et al. |
| 6,292,693 B1 | 9/2001 | Darvish et al. |
| 6,292,704 B1 | 9/2001 | Malonek et al. |
| 6,295,470 B1 | 9/2001 | Mower |
| 6,296,693 B1 | 10/2001 | McCarthy |
| 6,298,254 B2 | 10/2001 | Tamada |
| 6,298,268 B1 | 10/2001 | Ben-Haim et al. |
| 6,330,476 B1 | 12/2001 | Ben-Haim |
| 6,337,995 B1 | 1/2002 | Mower |
| 6,341,235 B1 | 1/2002 | Mower |

| | | |
|---|---|---|
| 6,343,232 B1 | 1/2002 | Mower |
| 6,363,279 B1 | 3/2002 | Ben-Haim et al. |
| 6,381,495 B1 | 4/2002 | Jenkins |
| 6,392,636 B1 | 5/2002 | Ferrari et al. |
| 6,411,847 B1 | 6/2002 | Mower |
| 6,417,846 B1 | 7/2002 | Lee |
| 6,424,864 B1 | 7/2002 | Matsuura |
| 6,433,069 B1 | 8/2002 | Oeltjen et al. |
| 6,449,511 B1 | 9/2002 | Mintchev et al. |
| 6,452,514 B1 | 9/2002 | Philipp |
| 6,463,323 B1 | 10/2002 | Conrad-Vlasak |
| 6,463,324 B1 | 10/2002 | Ben-Haim et al. |
| 6,473,069 B1 | 10/2002 | Gerpheide |
| 6,504,530 B1 | 1/2003 | Wilson et al. |
| 6,505,745 B1 | 1/2003 | Anderson |
| 6,507,093 B2 | 1/2003 | Kaneda et al. |
| RE38,119 E | 5/2003 | Mower |
| 6,567,700 B1 | 5/2003 | Turcott et al. |
| 6,570,557 B1 | 5/2003 | Westerman et al. |
| 6,571,127 B1 | 5/2003 | Ben-Haim et al. |
| 6,572,542 B1 | 6/2003 | Houben et al. |
| 6,583,676 B2 | 6/2003 | Krah et al. |
| 6,587,093 B1 | 7/2003 | Shaw et al. |
| 6,587,721 B1 | 7/2003 | Prutchi et al. |
| 6,600,953 B2 | 7/2003 | Flesler et al. |
| 6,611,258 B1 | 8/2003 | Tanaka et al. |
| 6,612,983 B1 | 9/2003 | Marchal |
| 6,630,123 B1 | 10/2003 | Woltering et al. |
| 6,633,280 B1 | 10/2003 | Matsumoto et al. |
| 6,634,895 B2 | 10/2003 | Agro |
| 6,652,444 B1 | 11/2003 | Ross |
| 6,658,297 B2 | 12/2003 | Loeb |
| 6,667,740 B2 | 12/2003 | Ely et al. |
| 6,684,104 B2 | 1/2004 | Gordon et al. |
| 6,690,156 B1 | 2/2004 | Weiner et al. |
| 6,762,752 B2 | 7/2004 | Perski et al. |
| 6,781,577 B2 | 8/2004 | Shigetaka |
| 6,810,286 B2 | 10/2004 | Donovan et al. |
| 6,853,862 B1 | 2/2005 | Marchal et al. |
| 6,919,205 B2 | 7/2005 | Brighton |
| 6,949,081 B1 | 9/2005 | Chance |
| 7,006,871 B1 | 2/2006 | Darvish et al. |
| 7,027,863 B1 | 4/2006 | Prutchi et al. |
| 7,062,318 B2 | 6/2006 | Ben-Haim et al. |
| 7,092,753 B2 | 8/2006 | Darvish et al. |
| 7,167,748 B2 | 1/2007 | Ben-Haim et al. |
| 7,171,263 B2 | 1/2007 | Darvish et al. |
| 7,190,997 B1 | 3/2007 | Darvish et al. |
| 7,460,907 B1 | 12/2008 | Darvish et al. |
| 7,840,262 B2 | 11/2010 | Mika et al. |
| 2002/0026141 A1 | 2/2002 | Houben et al. |
| 2002/0052632 A1 | 5/2002 | Ben-Haim et al. |
| 2002/0081732 A1 | 6/2002 | Bowlin et al. |
| 2002/0123771 A1 | 9/2002 | Ideker et al. |
| 2002/0161414 A1 | 10/2002 | Flesler et al. |
| 2002/0183682 A1 | 12/2002 | Darvish et al. |
| 2002/0183686 A1 | 12/2002 | Darvish et al. |
| 2003/0018367 A1 | 1/2003 | DiLorenzo |
| 2003/0028221 A1 | 2/2003 | Zhu et al. |
| 2003/0055464 A1 | 3/2003 | Darvish et al. |
| 2003/0100889 A1 | 5/2003 | Duverger et al. |
| 2003/0167476 A1 | 9/2003 | Conklin |
| 2003/0181958 A1 | 9/2003 | Doubak, III |
| 2003/0188899 A1 | 10/2003 | Chao et al. |
| 2003/0208242 A1 | 11/2003 | Harel et al. |
| 2003/0211475 A1 | 11/2003 | Roberts |
| 2004/0059393 A1 | 3/2004 | Policker et al. |
| 2004/0095333 A1 | 5/2004 | Morag et al. |
| 2004/0105040 A1 | 6/2004 | Oh et al. |
| 2004/0106954 A1 | 6/2004 | Whitehurst et al. |
| 2004/0138710 A1 | 7/2004 | Shemer et al. |
| 2004/0155871 A1 | 8/2004 | Perski et al. |
| 2004/0158289 A1 | 8/2004 | Girouard et al. |
| 2004/0230273 A1 | 11/2004 | Cates et al. |
| 2004/0243190 A1 | 12/2004 | Ben-Haim et al. |
| 2004/0249421 A1 | 12/2004 | Harel et al. |
| 2005/0033396 A1 | 2/2005 | Ospyka |
| 2005/0095227 A1 | 5/2005 | Rosenzweig et al. |
| 2005/0192542 A1 | 9/2005 | Dev et al. |
| 2006/0036126 A1 | 2/2006 | Ross et al. |
| 2006/0079475 A1 | 4/2006 | Zhang et al. |
| 2006/0085045 A1 | 4/2006 | Harel et al. |
| 2006/0097991 A1 | 5/2006 | Hotelling et al. |
| 2006/0184207 A1 | 8/2006 | Darvish et al. |
| 2007/0027487 A1 | 2/2007 | Mika et al. |
| 2007/0027490 A1 | 2/2007 | Ben-Haim et al. |
| 2007/0088393 A1 | 4/2007 | Ben-Haim et al. |
| 2007/0156177 A1 | 7/2007 | Harel et al. |
| 2007/0162079 A1 | 7/2007 | Shemer et al. |
| 2007/0171211 A1 | 7/2007 | Perski et al. |
| 2008/0058879 A1 | 3/2008 | Ben-Haim et al. |
| 2008/0065159 A1 | 3/2008 | Ben-Haim et al. |
| 2008/0065163 A1 | 3/2008 | Ben-Haim et al. |
| 2008/0065164 A1 | 3/2008 | Ben-Haim et al. |
| 2009/0062893 A1 | 3/2009 | Spehr et al. |
| 2009/0292324 A1 | 11/2009 | Rousso et al. |
| 2010/0016923 A1 | 1/2010 | Rousso et al. |

FOREIGN PATENT DOCUMENTS

| | | |
|---|---|---|
| EP | 0156593 | 10/1985 |
| EP | 0250931 | 1/1988 |
| EP | 0314078 B1 | 5/1989 |
| EP | 0481684 | 4/1992 |
| EP | 0 503 839 | 9/1992 |
| EP | 0503839 | 9/1992 |
| EP | 0528751 | 2/1993 |
| EP | 0220916 | 4/1994 |
| EP | 727 241 | 8/1996 |
| EP | 1263498 | 12/2002 |
| EP | 0910429 | 3/2005 |
| GB | 1394171 | 5/1975 |
| GB | 2280377 | 2/1995 |
| JP | 62-112530 | 5/1987 |
| JP | 62-275471 | 11/1987 |
| JP | 62275471 | 11/1987 |
| JP | 04-117967 | 4/1992 |
| JP | 04117967 A2 | 4/1992 |
| JP | 04-282168 | 10/1992 |
| JP | 04-365493 | 12/1992 |
| JP | 4365493 | 12/1992 |
| JP | 06-169998 | 6/1994 |
| JP | 06-506619 | 7/1994 |
| JP | 07-126600 | 5/1995 |
| JP | 7126600 | 5/1995 |
| JP | 07-144024 | 6/1995 |
| JP | 08-243176 | 9/1996 |
| JP | 8243176 A2 | 9/1996 |
| RU | 386634 | 10/1973 |
| RU | 553977 | 5/1977 |
| RU | 831131 | 5/1981 |
| RU | 2014844 | 6/1994 |
| RU | 2055606 | 3/1996 |
| RU | 2075980 | 3/1997 |
| RU | 2077273 | 4/1997 |
| RU | 2078547 | 5/1997 |
| WO | WO 92/00716 | 1/1992 |
| WO | WO 92/13592 | 8/1992 |
| WO | WO 93/02743 | 2/1993 |
| WO | WO 93/02745 | 2/1993 |
| WO | WO 93/08874 | 5/1993 |
| WO | WO 93/18820 | 9/1993 |
| WO | WO 94/17855 | 8/1994 |
| WO | WO 95/08316 | 9/1995 |
| WO | WO 96/10358 | 4/1996 |
| WO | WO 96/16696 | 6/1996 |
| WO | WO 97/15227 | 1/1997 |
| WO | WO 97/25101 | 1/1997 |
| WO | WO 97/06849 | 2/1997 |
| WO | WO 97/25098 | 7/1997 |
| WO | WO 97/26042 | 7/1997 |
| WO | WO 97/27900 | 7/1997 |
| WO | WO 98/10828 | 3/1998 |
| WO | WO 98/10829 | 3/1998 |
| WO | WO 98/10830 | 3/1998 |
| WO | WO 98/10831 | 3/1998 |
| WO | WO 98/10832 | 3/1998 |
| WO | WO 9810831 | 3/1998 |
| WO | WO 98/15317 | 4/1998 |

| | | |
|---|---|---|
| WO | WO 98/19719 | 4/1998 |
| WO | WO 98/19719 | 5/1998 |
| WO | WO 98/56378 | 12/1998 |
| WO | WO 98/57701 | 12/1998 |
| WO | WO 99/06105 | 2/1999 |
| WO | WO 99/09971 | 3/1999 |
| WO | WO 99/55360 | 4/1999 |
| WO | WO 99/24110 | 5/1999 |
| WO | WO 99/29307 | 6/1999 |
| WO | WO 99/59548 | 11/1999 |
| WO | WO 00/01443 | 1/2000 |
| WO | WO 0004947 | 2/2000 |
| WO | WO 00/16741 | 3/2000 |
| WO | WO 00/27475 | 5/2000 |
| WO | WO 00/42914 | 7/2000 |
| WO | WO 00/12525 | 9/2000 |
| WO | WO 00/53257 | 9/2000 |
| WO | WO 00/74773 | 12/2000 |
| WO | WO 01/24871 | 4/2001 |
| WO | WO 01/49367 | 7/2001 |
| WO | WO 01/52931 | 7/2001 |
| WO | WO 01/66183 | 9/2001 |
| WO | WO 01/91854 | 12/2001 |
| WO | WO 01/93950 | 12/2001 |
| WO | WO 01/93951 | 12/2001 |
| WO | WO 02/10791 | 2/2002 |
| WO | WO 02/053093 | 7/2002 |
| WO | WO 02/082968 | 10/2002 |
| WO | WO 03/045493 | 5/2003 |
| WO | WO 2004/059393 | 7/2004 |
| WO | WO 2004/070396 | 8/2004 |
| WO | WO 2004/080533 | 9/2004 |
| WO | WO 2005/023081 | 3/2005 |
| WO | WO 2005/087310 | 9/2005 |
| WO | WO 2005/114369 | 12/2005 |
| WO | WO 2006/073671 | 7/2006 |
| WO | WO 2006/087717 | 8/2006 |
| WO | WO 2006/097934 | 9/2006 |
| WO | WO 2006/097935 | 9/2006 |
| WO | WO 2006/119467 | 9/2006 |

OTHER PUBLICATIONS

Antman, E.M. et al. "Treatment of 150 Cases of Life-Threatening Digitalis Intoxication with Digoxin-Specific Fab Antibody Fragments;" Jun. 1990 Circulation; vol. 81: No. 6: pp. 1744-1752.

Antoni, H. et al. "Polarization Effects of Sinusoidal 50-Cycle Alternating Current on Membrane Potential of Mammalian Cardiac Fibers", Pfluegers Arch. 314, pp. 274-291 (1970).

Bach, S.M., Tach Arrhythmia Detection, Implantable Cardioverter Defibrilator Therapy: The Engineering-Clinical Interface, Chapter 15, pp. 303-323, Eds, Mark W. Kroll and Michael H. Lehmann, Kluwer Academic Publishers, USA , 1997.

Bakker, P.F., et al., "Beneficial Effects of Biventricular Pacing of Congestive Heart Failure", PACE, vol. 17, Apr. 1994, Part 11, one page.

Bakker, P.F., et al., "Biventricular Pacing Improves Functional Capacity in Patients with End-Stage Congestive Heart Failure" PACE, vol. 17, Apr. 1995, Part 11, one page.

Bargheer K. et al., "Prolongation of Monophasic Action Potential Duration and the Refractory Period in the Human Heart by Tedisamil, a New Potassium-Blocking Agent", J. Eur Heart 15 (10), Oct. 1994, pp. 1409-1414.

Bers, D.M., Excitation-Contraction Coupling and Cardiac Contractile Force, Kluwer Academic Publishers, London, 1993.

Borst, et al. "Coronary Artery Bypass Grafting Without Cardiopulomonary Bypass and Without Interuption of Native Coronary Flow Using a Novel Anastomosis site restraining device ('Octupus')", Journal of the American College of Cardiology, 27 (6), May 1996.

Cano, N.J. et al. "Dose-Dependent Reversal of Digoxin-Inhibited Activity of an In-Vitro NA+K+ATPase Model by Digoxin-Specific Antibody;" May 1996; pp. 107-1011; Toxicology Letters; vol. 85; No. 2.

Cazeau S. et al., "Multisite Pacing for End-Stage Heart Failure: Early Experience", Pacing and Clinical Electrophysiology vol. 19, Nov. 1996, Part 11, pp. 1748-1757.

Cooper, W., "Postextrasystolic Potentiation: Do We Really Know What It Means and How to Use It?" Circulation, vol. 88, No. 6, Dec. 1993, pp. 2962-2971.

Dillon, SM., "Optical Recordings in the Rabbit Heart Show that Defibrillation Strength Shocks Prolong the Duration of Depolarization and the Refractory Period" in Circ Res., 69 (3), Sep. 1991, pp. 842-856.

Dillon, SM., abstract of "Synchronized Repolarization After Defibrillation Shocks. A possible Component of the Defibrillation Process Demonstration by Optical Recordings in Rabbit Heart", Circulation, May 1992, vol. 85, No. 5, pp. 1865-1878.

Fain, E.S., et al. "Improved Internal Defibrillation Efficacy with a Biphasic Waveform", American Heart Journal 117 (2), Feb. 1989, pp. 358-364.

Fleg, J.L. et al., "Impact of Age on the Cardiovasvular Response to Dynamic Upright Exercise in Healthy Men and Women", J. Appl. Physiol., vol. 78, 1995, p. 890.

Foster, A.H, et al., "Acute Hemodynamic Effects of Atrio-Biventricular Pacing in Humans", 1995, The Society of Thoracic Surgeons vol. 59, pp. 294-299.

Franz, M.R., "Bridging the Gap Between Basic and Clinical Electrophysiology: What Can be Learned from Monophasic Action Potential Recordings?", J. Cardiovasc Electrophysiol 5(8), Aug. 1994, pp. 699-710.

Franz, M.R.,"Method and Theory of Monophasic Action Potential Recording", Prog. Cardiovasc Dis 33 (6), May-Jun. 1991, pp. 347-368.

Franz, M.R., "Progress in Cardiovascular Disease: Monophasic Action Potential Symposium, I. Introduction", Prog. Cardiovasc Dis 33 (6), May-Jun. 1991 pp. 345-346.

Fromer et al., "Ultrarapid Subthreshold Stimulation for Termination of Atrioventricular Node Reentrant Tachycardia", Journal of the American College of Cardiology 20 (Oct. 1992), pp. 879-883.

Fu. P and B.J. Bardakjian, "System Identification of Electrically Coupled Smooth Muscle Cells: The Passive Electrically Coupled Smooth Muscle Cells: The Passive Electrical Properties", published in IEEE Transactions on Biomedical Engineering, 38(11), pp. 1130-1140, 1991.

Ham, Frederic M and Han, Soowhan, "Classification of Cardiac Arrhythmias Using Fuzzy Artmap"; IEEE Transactions on Biomedical Engineering, vol. 43, No. 4, Apr. 1996.

Hoffman, B.F. et al., "Effects of Postextrasystolic Potentiation on Normal & Failing Hearts", Bulletin of New York Academy of Medicine, 41 in 1965, pp. 498-534.

Josephson, M.E., Clinical Cardiac Electrophysiology: Techniques and Interpertations, 2nd. Edition, Lea & Febiger, Philadelphia, 1991.

King, A. et al., "The Inotropic Action of Paired Pulse Stimulation in the Normal and Failing Heart: An Experimental Study", Cardiovascular Research, vol. 2, Apr. 1968, pp. 122-129.

Knisley et al., "Prolgongation and Shortening of Action Potentials by Electrical Shocks in Frog Ventricular Muscle", American Journal of Physiology 6 (Heart Circ. Physiol. 35, 1994) pp. H2348-H2358.

Koller, et al., "Relation Between Repolarization and Refractoriness During Programmed Electrical Stimulation in the Human Right Ventricle", Circulation 91(9), 2378-2384, 1995.

Langberg, Jonathan J. et al., "Identification of Ventricular Tachycardia with Use of the Morphology of the Endocardial Electrogram", Circulation, vol. 77, No. 6, Jun. 1988.

McVeigh, E.R et al., "Noninvasive Measurement of Transmural Gradients in Myocardial Strain with MR Imaging", Radiology 180 (3), Sep. 1991, pp. 677, 679-684.

Mercando, A.D., et al., "Automated Detection of Tachardias by Antitachicardia Devices", Chapter 100, pp. 943-948, in Cardiac Electrophysiology from Cell to Bedside, Eds. Douglas P. Zipes and Jose Jalife, publishers W.B. Saunders Company (1990).

Moran, R.J. et al; "Digoxin-Specific Fab Fragments Impair Renal Function in the Rat:" 1994; pp. 854-856; Journal of Pharmacy and Pharmacology; vol. 46: No. 10.

Morse, et al., "A Guide to Cardiac Pacemakers,Defibrillators and Related Products", Droege Computing Services, Durham, NC.

Merck Manual, The, Section 3, The 16th Edition of the Merck Manual, Published in 1992.

Paul, VE., et al. "Automatic Recognition of Ventricular Arrythmias Using Temporal Electrogram Anaylsis" Pace, vol. 14, pp. 1265-1273, (1991).

Qiuzhen Xue et al., "Neural-Network-Based Adaptive Matched Filtering for QRS Detection", IEEE Transactions on Biomedical Engineering, vol. 39, No. 4. Apr. 1992.

Saksena et al., "Dual-site Atrial Pacing in Atrial Fibrillation", JACC, vol. 28, No. 3, Sep. 1996, pp. 687-694.

Shumaik, G.M. et al, "Oleander Poisoning; Treatment with Digoxin-Specific Fab Antibody Fragments;" Jul. 1988; pp. 732-735; Annals of Emergency Medicine; vol. 17; No. 7.

Sweeny RJ, et al., abstract of "Countershock Strength-Duration Relationship for Myocardial Refractory Period Extension", Acad Emerg. Med., Jan. 1995, vol. 2, No. 1, pp. 57-62.

Sweeny RJ, et al., abstract of "Refractory Interval After Transcardiac Shocks During Ventricular Fibrillation", Circulation, Dec. 1996, vol. 94, No. 11, pp. 2947-2952.

Sweeny RJ, et al., abstract of "Ventricular Refractory Period Extension Caused by Defibrillation Shocks", Circulation, Sep. 1990, vol. 82, No. 3, pp. 965-972.

Talit, U. et al., "The Effect of External Cardiac Pacing on Stroke Volume", Pace 13, May 1990, pp. 598-560.

Tsong, T.Y., "Electroportion of Cell Membranes" Aug. 1991; pp. 297-306; Biophysical Journal; vol. 60.

Verrier, et al, "Electrophysiologic Basis for T Wave Alternans as an Index of Vulnerability to Ventricular Fibrillation" Journal of Cardiovascular Electrophysiology, vol. 5, pp. 445-461, 1994.

Webster, John G., ed., Design of Cardiac Pacemakers, IEEE Press, Piscataway, New Jersey, 1995.

Wessale, J.L. et al., "Stroke Volume and Three Phase Cardiac Output Rate Relationship with Ventricular Pacing" Pace 13, May 1990, pp. 673-680.

Wirtzfeld, A. et al., "Physiological Pacing: Present Status and Future Developments", Pace 10 Jan.-Feb. 1987, Part I, pp. 41-57.

Zipes, D et al., Cardiac Electrophysiology from Cell to Bedside, 1990, W.B. Saunders Co., Philadelphia.

Guidant Product Catalogue, 2001, 2 pages.

"The Latest Tetralogy of Fallot Discussion with Graphical Support Including Video of Echocardiography and Catherization" Pediatric Electrophysiologypicu Book ("An On-Line Resource for Pediatric Critical Care").

Brumwell D.A. et al. "The Amplifier: Sensing the Depolarization", Implantable Cardioverter Defibrillator Therapy: The Engineering-Clinical Interface, Chapt. 14, pp. 275-302, Eds. Kroll and Lehmann, Kluwer Academic Publishers, USA 1997.

Gill RJ, et al., abstract of "Refractory Period Extension During Ventricular Pacing at Fibrillatory Pacing Rates" Pacing Clin. Elctrophysiol, Mar. 1997, vol. 20, No. 3, pp. 647-653.

Hardage, M.L. and Sweeney, M.B., "Anti-Tachycardia Pacing and Cardioversion", Implantable Cardiovertre Defibrilator Therapy: The Engineering-Clinical Interface, Chapt. 6, pp. 325-342, Eds. Mark W. Kroll and Michael H. Lehmann, Kluwer Academic Publishers U.S.A 1997.

Matheny R.G. and C.J. Shaar, "Vagus Nerve Stimulation as a Method to Temporarily Slow or Arrest the Heart" Annals of Thoracic Surgery. 63 (6) Supplement, pp. S28-S29, Jun. 1997.

Supino, C.G., "The System", Implantable Cardioverter Defibrillator Therapy: The Engineering-Clinal Interface, Chapt. 8, pp. 183-172, Eds. Mark W. Kroll and Michael H. Lehmann, Kluwer Academic Publishers, USA 1997.

Thakor et al., "Effect of Varying Pacing Waveform Shapes on Propagation and Hemodynamics in the Rabbit Heart", The Americal Journal of Cardiology 79 (6A), pp. 36-43, 1997.

Josephson, M.E., Clinical Cardiac Electrophysiology: Techniques and Interpretations, 2nd Edition, Lea & Febiger, Philadelphia, 1991, Chapters 3 and 15.

Morse, et al., A Guide to Cardiac Pacemakers, Defibrillators and Related Products, Droege Computing Services, Durham, NC, pp. 2-1 to 2-8.

Merck Manual, The, Section 3, the 16th Edition of the Merck Manual, Published 1992, pp. 471-473.

Saksena et al., Prevention of Recurent Atrial Fibrillation With Chronic Dual-Site Right Atrial Pacing, JACC, vol. 28, No. 3, Sep. 1996, pp. 687-694.

Webster, John G., ed., Design of Cardiac Pacemakers, IEEE Press, Piscataway, New Jersey, 1995, Chapters 5, 9, and 13-16.

Zipes, D., et al., Cardiac Electrophysiology from Cell to Bedside, 1990 W.B. Saunders Co., Philadelphia, Chapters 87, 99-102, and 104.

"The Latest Tetralogy of Fallot Discussion with Graphical Support including Video of Echocardiography and Catherization" Pediatric Electrophysiologypicu Book ("An Online Resource for Pediatric Critical Care"), 1998.

J. L. Wessale et al., "Stroke Volume and Three Phase Cardiac Output Rate Relationship with Ventricular Pacing", *PACE* 13, May 1990, pp. 673-680.

A. Wirtzfeld et al., "Physiological Pacing: Present Status and Future Developments", *PACE* 10 Jan.-Feb. 1987, Part I, pp. 41-57.

U. Talit et al., "The Effect of External Cardiac Pacing on Stroke Volume", *PACE* 13, May 1990, pp. 598-602.

John G. Webster, ed., *Design of Cardiac Pacemakers*, IEEE Press, Piscataway, New Jersey, 1995.

E. S. Fain et al., "Improved Internal Defibrillation Efficacy with a Biphasic Waveform", *American Heart Journal* 117(2), Feb. 1989, pp. 358-364.

Knisley et al., "Prolongation and Shortening of Action Potentials by Electrical Shocks in Frog Ventricular Muscle", *American Journal of Physiology* 6 (*Heart Circ. Physiol*. 35, 1994) pp. H2348-H2358.

Thakor et al., "Effect of Varying Pacing Waveform Shapes on Propagation and Hemodynamics in the Rabbit Heart", *The American Journal of Cardiology* 79(6A), pp. 36-43. 1997.

M. R. Franz, "Method and Theory of Monophasic Action Potential Recording", *Prog. Cardiovasc Dis* 33(6), May-Jun. 1991, pp. 347-368.

M.R.Franz, "Bridging the Gap between Basic and Clinical Electrophysiology: What Can Be Learned from Monophasic Action Potential Recordings?", *J. Cardiovasc Electrophysiol* 5(8), Aug. 1994, pp. 699-710.

K. Bargheer et al., "Prolongation of Monophasic Action Potential Duration and the Refractory Period in the Human Heart by Tedisamil, a New Potassium-Blocking Agent", *J. Eur Heart* 15(10), Oct. 1994, pp. 1409-1414.

M.R. Franz, "Progress in Cardiovascular Diseases: Monophasic Action Potential Symposium, I. Intoduction", *Prog. Cardiovasc Dis* 33(6), May-Jun. 1991, pp. 345-346.

E. R. McVeigh et al., "Noninvasive Measurement of Transmural Gradients in Myocardial Strain with MR Imaging", *Radiology* 180(3), Sep. 1991, pp. 677, 679-684.

D. M. Bers, *Excitation-Contraction Coupling and Cardiac Contractile Force*. 1991.

D. Zipes et al., *Cardiac Electrophysiology from Cell to Bedside*, 1990,W. B. Saunders Co., Philadelphia. 1990.

M. E. Josephson, *Clinical Cardiac Electrophysiology: Techniques and Interpretations*, 2nd Edition, Lea & Febiger, Philadelphia. 1991.

H. Antoni et al., "Polarization Effects of Sinusoidal 50 Hz Alternating Current on Membrane Potential of Mammalian Cardiac Fibres", 1970.

Notice of Non-Compliant Amendment Dated Dec. 12, 2011 From the US Patent and Trademark Office Re. U.S. Appl. No. 11/792,811.

Notice of Allowance Dated Jan. 14, 2011 From the US Patent and Trademark Office Re.: U.S. Appl. No. 11/550,560.

Official Action Dated Jan. 3, 2011 From the US Patent and Trademark Office Re.: U.S. Appl. No. 11/932,149.

Official Action Dated Jan. 24, 2011 From the US Patent and Trademark Office Re.: U.S. Appl. No. 11/919,491.

Response Dated Feb. 3, 2011 to Official Action of Jan. 3, 2011 From the US Patent and Trademark Office Re.: U.S. Appl. No. 11/932,149.

Response Dated Feb. 7, 2011 to Official Action of Oct. 5, 2010 From the US Patent and Trademark Office Re.: U.S. Appl. No. 10/039,845.

Response Dated Feb. 14, 2011 to Official Action Dated Jan. 13, 2011 From the US Patent and Trademark Office Re.: U.S. Appl. No. 11/931,889.

Hammond et al. "Motor Innervation of the Cricopharyngeus Muscle by the Recurrent Lanryngeal Nerve", Journal of Applied Physiology, JAP, 83: 89-94, 1997.

Sutton et al. "The Foundation of Cardiac Pacing, Part I: An Illustrated Practical Guide to Basic Pacing", The Bakken Research Center Series, Chap.4: 50-59, 1991.

Response Dated Oct. 11, 2011 to Official Action of May 12, 2011 From the US Patent and Trademark Office Re.: U.S. Appl. No. 10/039,845.

USPTO Public Print Out of Interference File Content of Interference Dated Apr. 4, 2011 From the US Patent and Trademark Office Re. Interference No. 105,765.

USPTO Public Print Out of Interference File Content of Interference Dated Apr. 4, 2011 From the US Patent and Trademark Office Re. Interference No. 105,768.

Notice of Non-Compliant Amendment Dated Jun. 1, 2011 From the US Patent and Trademark Office Re. U.S. Appl. No. 11/886,154.

Official Action Dated May 12, 2011 From the US Patent and Trademark Office Re.: U.S. Appl. No. 10/039,845.

Official Action Dated Apr. 14, 2011 From the US Patent and Trademark Office Re.: U.S. Appl. No. 11/932,149.

Official Action Dated Apr. 28, 2011 From the US Patent and Trademark Office Re.: U.S. Appl. No. 11/931,889.

Response Dated May 15, 2011 to Office Action of Nov. 25, 2010 From the State Intellectual Property Office (SIPO) of the People's Republic of China Re.: Application No. 200480012687.5. & Claims in English.

Response Dated Apr. 20, 2011 to Official Action of Mar. 22, 2011 From the US Patent and Trademark Office Re. U.S. Appl. No. 11/886,154.

Supplemental Response Dated Apr. 18, 2011 to Response of Apr. 10, 2011 to Official Action of Jan. 6, 2011 From the US Patent and Trademark Office Re.: U.S. Appl. No. 11/931,724.

Translation of Office Action Dated Apr. 20, 2011 From the State Intellectual Property Office (SIPO) of the People's Republic of China Re.: Application No. 200480012687.5.

Communication Pursuant to Article 94(3) EPC Dated Aug. 26, 2011 From the European Patent Office Re. Application No. 06759102.4.

Communication Pursuant to Article 94(3) EPC Dated Aug. 26, 2011 From the European Patent Office Re.: Application No. 05853465.2.

Notice of Non-Compliant Amendment Dated Jul. 15, 2011 From the US Patent and Trademark Office Re. U.S. Appl. No. 11/886,154.

Official Action Dated Aug. 9, 2011 From the US Patent and Trademark Office Re.: U.S. Appl. No. 11/932,149.

Official Action Dated Oct. 10, 2008 From the US Patent and Trademark Office Re. U.S. Appl. No. 09/980,748.

Official Action Dated Oct. 11, 2011 From the US Patent and Trademark Office Re.: U.S. Appl. No. 11/919,491.

Official Action Dated Sep. 11, 2009 From the US Patent and Trademark Office Re. U.S. Appl. No. 09/980,748.

Official Action Dated Sep. 14, 2011 From the US Patent and Trademark Office Re. U.S. Appl. No. 11/886,154.

Official Action Dated May 21, 2007 From the US Patent and Trademark Office Re. U.S. Appl. No. 09/980,748.

Official Action Dated Dec. 23, 2010 From the US Patent and Trademark Office Re. U.S. Appl. No. 09/980,748.

Official Action Dated Feb. 28, 2008 From the US Patent and Trademark Office Re. U.S. Appl. No. 09/980,748.

Official Action Dated Apr. 29, 2009 From the US Patent and Trademark Office Re. U.S. Appl. No. 09/980,748.

Official Action Dated Aug. 30, 2006 From the US Patent and Trademark Office Re. U.S. Appl. No. 09/980,748.

Official Action Dated Mar. 31, 2011 From the US Patent and Trademark Office Re. U.S. Appl. No. 11/673,812.

Response Dated Aug. 1, 2011 to Notice of Non-Compliant Amendment of Jul. 15, 2011 From the US Patent and Trademark Office Re. U.S. Appl. No. 11/886,154.

Response Dated Jan. 24, 2011 to Supplementary Partial European Search Report of Nov. 4, 2010 From the European Patent Office Re. Application No. 04719312.3.

Response Dated Jul. 27, 2011 to Official Action of Apr. 28, 2011 From the US Patent and Trademark Office Re. U.S. Appl. No. 11/931,889.

Response Dated Jul. 27, 2011 to Official Action of Apr. 28, 2011 From the US Patent and Trademark Office Re.: U.S. Appl. No. 11/931,889.

Response Dated Jun. 29, 2011 to Notice of Non-Compliant Amendment of Jun. 1, 2011 From the US Patent and Trademark Office Re. U.S. Appl. No. 11/886,154.

Response Dated Aug. 31, 2011 to Official Action of Mar. 31, 2011 From the US Patent and Trademark Office Re. U.S. Appl. No. 11/673,812.

Response Dated Jul. 31, 2011 to Official Action of Apr. 14, 2011 From the US Patent and Trademark Office Re.: U.S. Appl. No. 11/932,149.

Translation of Notice of Reasons for Rejection Dated Jul. 18, 2006 From the Japanese Patent Office Re.: Application No. 09-529637.

Translation of Office Action Dated Aug. 3, 2011 From the State Intellectual Property Office (SIPO) of the People's Republic of China Re.: Application No. 200480012687.5.

Erol-Yilmaz et al. "Reversed Remodelling of Dilated Left Sided Cardiomyopathy After Upgrading from VVIR to VVIR Biventricular Pacing", Europace, 4: 445-449, 2002.

Holst et al. "Nervous Control of Pancreatic Endocrine Secretion in Pigs. I. Insulin and Glucagon Responses to Electrical Stimulation of the Vagus Nerves", Acta Physiologica Scandinavica, 111(1): 1-7, Jan. 1981. Abstract.

Holst et al. "Nervous Control of Pancreatic Endocrine Secretion in Pigs. II. The Effect of Pharmacological Blocking Agents on the Response to Vagal Stimulation", Acta Physiologica Scandinavica, 111(1): 9-14, 1981. Abstract.

Horner et al. "Electrode for Recording Direction of Activation, Conduction Velocity and Monophasic Action Potential of Myocardium", American Journal of Physiology, 272(4): H1917-H1927, 1997. Abstract.

Magnus et al. "Model of ?—Cell Mitochondrial Calcium Handling and Electrical Activity. II. Mitochondrial Variables", American Journal of Physiology, Cell Physiology, 274(43): C1174-C1184, 1998.

Park et al. "Significant Cholinergic Role in Secretin-Stimulated Exocrine Secretion in isolated Rat Pancreas", American Journal of Physiology, AJP—Gastrointestinal and Liver Physiology, 274(2): G413-G418, Feb. 1998.

Porksen et al. "Section 6: Pulsatile and Phasic Insulin Release in Normal and Diabetic Man. Pulsatile Insulin Secretion: Detection, Regulation, and Role in Diabetes", Diabetes, 51(Supp1.1): S245-S254, Feb. 2002.

Sutton et al. "What Is a Pacemaker?", The Foundations of Cardiac Pacing, Part 1: An Illustrated Practical Guide to Basic Pacing, Chap. 4.5: 73-74, 1991.

Wang et al. "Islet Amyloid Polypeptide Tonally Inhibits Beta-, Alpha-, and Delta-Cell Secretion in Isolated Rat Pancreatic Islets", American Journal of Physiology, AJP—Endocrinology and Metabolism, 276(1 Pt.1): E19-E24, 1999.

Webster "Electrodes, Leads, and Biocompatibility", Design of Cardiac Pacemakers, IEEE Press, p. 141-144, 1995.

Xue et al. "Neural-Network-Based Adaptive Matched Filtering for QRS Detection", IEEE Transactions on Biomedical Engineering, 39(4): 317-329, 1992. Abstract.

Official Action Dated Feb. 15, 2012 From the US Patent and Trademark Office Re. U.S. Appl. No. 11/802,685.

Office Action Dated Jan. 18, 2012 From the State Intellectual Property Office (SIPO) of the People's Republic of China Re.: Application No. 200480012687.5 and Its Translation Into English.

Office Action Dated Feb. 21, 2012 From the US Patent and Trademark Office Re. U.S. Appl. No. 10/116,201.

Official Action Dated Dec. 20, 2011 From the US Patent and Trademark Office Re.: U.S. Appl. No. 10/039,845.

Response Dated Dec. 8, 2011 to Office Action of Aug. 3, 2011 From the State Intellectual Property Office (SIPO) of the People's Republic of China Re.: Application No. 200480012687.5.

Response Dated Dec. 14, 2011 to Official Action of Sep. 14, 2011 From the US Patent and Trademark Office Re. U.S. Appl. No. 11/886,154.

Official Action Dated Jan. 4, 2012 From the US Patent and Trademark Office Re. U.S. Appl. No. 11/673,812.

Official Action Dated Dec. 15, 2011 From the US Patent and Trademark Office Re. U.S. Appl. No. 12/910,943.
Response Dated Dec. 8, 2011 to Official Action of Aug. 9, 2011 From the US Patent and Trademark Office Re.: U.S. Appl. No. 11/932,149.
Response Dated Dec. 27, 2011 to Communication Pursuant to Article 94(3) EPC of Aug. 16, 2011 From the European Patent Office Re. Application No. 06759102.4.
Official Action Dated Jan. 18, 2012 From the US Patent and Trademark Office Re. U.S. Appl. No. 11/886,154.
U.S. Appl. No. 90/008,688, filed Jun. 15, 2007, Ben Haim.
U.S. Appl. No. 90/008,689, Ben Haim.
U.S. Appl. No. 90/008,707, filed Jun. 7, 2007, Ben Haim.
U.S. Appl. No. 95/000,032, Ben Haim.
Amended Request for Ex Parte Reexamination of US Patent No. 6,317,631 Dated Aug. 20, 2007 From the US Patent and Trademark Office Re.: U.S. Appl. No. 90/008,689.
Communication Pursuant to Article 94(3) EPC Dated Mar. 2, 2009 From the European Patent Office Re.: Application No. 05853465.2.
Communication Pursuant to Article 94(3) EPC Dated Aug. 11, 2010 From the European Patent Office Re. Application No. 99931435.4.
Communication Pursuant to Article 94(3) EPC Dated Jan. 29, 2009 From the European Patent Office Re.: Application No. 04106247.2.
Communication Pursuant to Article 96(2) EPC Dated Mar. 2, 2007 From the European Patent Office Re.: Application No. 97929478.2.
Communication to Pursuant to Article 94(3) EPC Dated Mar. 4, 2009 From the European Search Report Re.: Application No. 06759102.4.
Inter Partes Reexamination Communication of Patent US 6,330,476 Dated Sep. 4, 2007 From the US Patent and Trademark Office Re.: U.S. Appl. No. 95/000,032.
International Preliminary Report on Patentability Dated Nov. 15, 2007 From the International Bureau of WIPO Re.: Application No. PCT/US2006/017281.
International Preliminary Report on Patentability Dated Jun. 21, 2007 From the International Bureau of WIPO Re.: Application No. Jun. 21, 2007.
International Preliminary Report on Patentability Dated Sep. 27, 2007 From the International Bureau of WIPO Re.: Application No. PCT/IL2006/000345.
International Search Report and the Written Opinion Dated May 12, 2006 From the International Searching Authority Re.: Application No. PCT/US05/44557.
International Search Report and the Written Opinion Dated Oct. 16, 2006 From the International Searching Authority Re.: Application No. PCT/US06/17281.
Invitation Pursuant to Rule 62a(1) EPC and Rule 63(1) EPC Dated May 5, 2010 From the European Patent Office Re.: Application No. 04719312.3.
Notice of Allowance Dated May 27, 2010 From the US Patent and Trademark Office Re.: U.S. Appl. No. 10/549,216.
Notice of Allowance Dated Dec. 28, 2010 From the US Patent and Trademark Office Re.: U.S. Appl. No. 11/932,064.
Office Action Dated Jan. 8, 2010 From the State Intellectual Property Office (SIPO) of the People's Republic of China Re.: Application No. 200480012687.5 and Its Translation Into English.
Office Action Dated Oct. 12, 2004 From the Israeli Patent Office Re.: Application No. 128955.
Office Action Dated Jul. 13, 2009 From the State Intellectual Property Office of the People's Republic of China Re.: Application No. 200480027083.3 and Its Translation Into English.
Office Action Dated Dec. 15, 2008 From the State Intellectual Property Office (SIPO) of the People's Republic of China Re.: Application No. 200480012687.5 and Its Translation Into English.
Official Action Dated Aug. 1, 2007 From the US Patent and Trademark Office Re.: U.S. Appl. No. 90/008,312.
Official Action Dated Jun. 1, 2009 From the US Patent and Trademark Office Re.: U.S. Appl. No. 10/039,845.
Official Action Dated Dec. 2, 2009 From the US Patent and Trademark Office Re.: U.S. Appl. No. 11/932,149.
Official Action Dated Nov. 3, 2009 From the US Patent and Trademark Office Re.: U.S. Appl. No. 11/931,724.
Official Action Dated Feb. 4, 2010 From the US Patent and Trademark Office Re.: U.S. Appl. No. 10/039,845.
Official Action Dated Dec. 5, 2008 From the US Patent and Trademark Office Re.: U.S. Appl. No. 11/550,560.
Official Action Dated Jan. 5, 2010 From the US Patent and Trademark Office Re.: U.S. Appl. No. 11/802,685.
Official Action Dated Nov. 5, 2009 From the US Patent and Trademark Office Re.: U.S. Appl. No. 10/549,216.
Official Action Dated Oct. 5, 2010 From the US Patent and Trademark Office Re.: U.S. Appl. No. 10/039,845.
Official Action Dated Jan. 6, 2011 From the US Patent and Trademark Office Re.: U.S. Appl. No. 11/931,724.
Official Action Dated Mar. 6, 2009 From the US Patent and Trademark Office Re.: U.S. Appl. No. 11/931,889.
Official Action Dated Mar. 6, 2009 From the US Patent and Trademark Office Re.: U.S. Appl. No. 11/932,064.
Official Action Dated Oct. 6, 2009 From the US Patent and Trademark Office Re.: U.S. Appl. No. 11/550,560.
Official Action Dated Oct. 8, 2009 From the US Patent and Trademark Office Re.: U.S. Appl. No. 10/116,201.
Official Action Dated Jun. 11, 2010 From the US Patent and Trademark Office Re.: U.S. Appl. No. 11/550,560.
Official Action Dated Jun. 11, 2010 From the US Patent and Trademark Office Re.: U.S. Appl. No. 11/932,064.
Official Action Dated Sep. 12, 2008 From the US Patent and Trademark Office Re.: U.S. Appl. No. 10/039,845.
Official Action Dated Jan. 13, 2011 From the US Patent and Trademark Office Re.: U.S. Appl. No. 11/931,889.
Official Action Dated Oct. 13, 2010 From the US Patent and Trademark Office Re.: U.S. Appl. No. 11/919,491.
Official Action Dated Sep. 14, 2009 From the US Patent and Trademark Office Re.: U.S. Appl. No. 11/931,889.
Official Action Dated Jul. 15, 2008 From the US Patent and Trademark Office Re.: U.S. Appl. No. 10/116,201.
Official Action Dated Jun. 17, 2010 From the US Patent and Trademark Office Re.: U.S. Appl. No. 10/549,216.
Official Action Dated Jul. 18, 2007 From the US Patent and Trademark Office Re.: U.S. Appl. No. 10/039,845.
Official Action Dated Jul. 21, 2010 From the US Patent and 'trademark Office Re.: U.S. Appl. No. 11/802,685.
Official Action Dated May 21, 2010 From the US Patent and Trademark Office Re. U.S. Appl. No. 10/116,201.
Official Action Dated Jun. 23, 2009 From the US Patent and Trademark Office Re.: U.S. Appl. No. 10/549,216.
Official Action Dated Jun. 26, 2008 From the US Patent and Trademark Office Re.: U.S. Appl. No. 11/536,794.
Official Action Dated Aug. 28, 2009 From the US Patent and Trademark Office Re.: U.S. Appl. No. 11/802,685.
Official Action Dated Aug. 28, 2009 From the US Patent and Trademark Office Re.: U.S. Appl. No. 11/932,064.
Official Action Dated Jun. 28, 2010 From the US Patent and Trademark Office Re.: U.S. Appl. No. 11/931,889.
Official Action Dated Apr. 30, 2010 From the US Patent and Trademark Office Re.: U.S. Appl. No. 11/931,724.
Official Action Dated Apr. 30, 2010 From the US Patent and Trademark Office Re.: U.S. Appl. No. 11/932,149.
Official Action Dated Aug. 31, 2007 From the US Patent and Trademark Office Re.: U.S. Appl. No. 11/536,794.
Official Action Dated Aug. 31, 2010 From the US Patent and Trademark Office Re.: U.S. Appl. No. 11/550,560.
Request for Ex Parte Reexamination of Patent No. 6,363,279—IDS Submitted Dec. 31, 2007 From the US Patent and Trademark Office Re.: U.S. Appl. No. 90/008,688.
Request for Ex Parte Reexamination of Patent No. 6,363,279—Notice of Intent to Issue Reexamination Certificate Dated Mar. 18, 2009 From the US Patent and Trademark Office Re.: U.S. Appl. No. 90/008,688.
Request for Ex Parte Reexamination of Patent No. 6,363,279—Official Action Dated Jun. 20, 2008 From the US Patent and Trademark Office Re.: U.S. Appl. No. 90/008,688.
Request for Ex Parte Reexamination of Patent No. 6,363,279—Order Granting Request Dated Nov. 5, 2007 From the US Patent and Trademark Office Re.: U.S. Appl. No. 90/008,688.

Request for Ex Parte Reexamination of Patent No. 6,363,279 Dated Jun. 8, 2007 From the US Patent and Trademark Office Re.: U.S. Appl. No. 90/008,688.
Request for Ex Parte Reexamination of Patent No. 6,363,279, Response to Official Action Dated Jun. 20, 2008 Submitted Aug. 20, 2008 From the US Patent and Trademark Office Re.: U.S. Appl. No. 90/008,688.
Request for Ex Parte Reexamination of US Patent No. 6,236,887—IDS Submitted Oct. 17, 2007 From the US Patent and Trademark Office Re.: U.S. Appl. No. 90/008,707.
Request for Ex Parte Reexamination of US Patent No. 6,236,887—IDS Submitted Sep. 29, 2008 From the US Patent and Trademark Office Re.: U.S. Appl. No. 90/008,707.
Request for Ex Parte Reexamination of US Patent No. 6,236,887—Notice of Intent to Issue Ex Parte Examination Certificate Dated Mar. 19, 2009 From the US Patent and Trademark Office Re.: U.S. Appl. No. 90/008,707.
Request for Ex Parte Reexamination of US Patent No. 6,236,887—Official Action and IDS Considered Dated Jun. 20, 2008 From the US Patent and Trademark Office Re.: U.S. Appl. No. 90/008,707.
Request for Ex Parte Reexamination of US Patent No. 6,236,887—Official Action Granting Request for Ex Parte Examination Dated Aug. 17, 2007 From the US Patent and Trademark Office Re.: U.S. Appl. No. 90/008,707.
Request for Ex Parte Reexamination of US Patent No. 6,236,887 Dated Jun. 13, 2007 From the US Patent and Trademark Office Re.: U.S. Appl. No. 90/008,707.
Request for Ex Parte Reexamination of US Patent No. 6,298,268—Certificate of Reexamination Issued Mar. 7, 2006, U.S. Appl. No. 90/006,788.
Request for Ex Parte Reexamination of US Patent No. 6,298,268—IDS Considered Feb. 22, 2005, U.S. Appl. No. 90/006,788.
Request for Ex Parte Reexamination of US Patent No. 6,298,268—Notice of Intent to Issue Certificate of Reexamination Dated Mar. 29, 2005, U.S. Appl. No. 90/006,788.
Request for Ex Parte Reexamination of US Patent No. 6,298,268 Dated Oct. 10, 2003, U.S. Appl. No. 90/006,788.
Request for Ex Parte Reexamination of US Patent No. 6,298,268 Order Granting Request for Ex Parte Reexamination Dated Dec. 19, 2003, U.S. Appl. No. 90/006,788.
Request for Ex Parte Reexamination of US Patent No. 6,317,631—Amendment in Response to Official Action Dated Jun. 20, 2008, Filed Aug. 20, 2008 From the US Patent and Trademark Office Re.: U.S. Appl. No. 90/008,689.
Request for Ex Parte Reexamination of US Patent No. 6,317,631—IDS Dated Sep. 26, 2008 From the US Patent and Trademark Office Re.: U.S. Appl. No. 90/008,689.
Request for Ex Parte Reexamination of US Patent No. 6,317,631—IDS Dated Dec. 31, 2007 From the US Patent and Trademark Office Re.: U.S. Appl. No. 90/008,689.
Request for Ex Parte Reexamination of US Patent No. 6,317,631—Notice of Intent to Issue Certificate of Reexamination Dated Mar. 18, 2009 From the US Patent and Trademark Office Re.: U.S. Appl. No. 90/008,689.
Request for Ex Parte Reexamination of US Patent No. 6,317,631—Official Action Dated Jun. 20, 2008, U.S. Appl. No. 90/008,689.
Request for Ex Parte Reexamination of US Patent No. 6,317,631—Order Granting Reexamination Dated Nov. 5, 2007, U.S. Appl. No. 90/008,689.
Request for Ex Parte Reexamination of US Patent No. 6,317,631—IDS Dated Jun. 8, 2007, U.S. Appl. No. 90/008,689.
Request for Ex Parte Reexamination of US Patent No. 6,330,476—IDS Dated May 31, 2006.
Request for Ex Parte Reexamination of US Patent No. 6,330,476—Comments by 3rd Party Requestor, Response Thereto and Official Action Issued Jul. 16, 2008, U.S. Appl. No. 95/000,032.
Request for Ex Parte Reexamination of US Patent No. 6,330,476—Communication of Right to Appeal dated Jul. 16, 2008, U.S. Appl. No. 95/000,032.
Request for Ex Parte Reexamination of US Patent No. 6,330,476—IDS Filed May 4, 2007, U.S. Appl. No. 95/000,032.

Request for Ex Parte Reexamination of US Patent No. 6,330,476—Official Action by USPTO Issued Mar. 23, 2004, U.S. Appl. No. 95/000,032.
Request for Ex Parte Reexamination of US Patent No. 6,330,476—Order Granting Request for Reexamination Dated Mar. 23, 2004 From the US Patent and Trademark Office Re.: U.S. Appl. No. 95/000,032.
Request for Ex Parte Reexamination of US Patent No. 6,330,476 Dated Dec. 31, 2003 From the US Patent and Trademark Office Re.: U.S. Appl. No. 95/000,032.
Request for Ex Parte Reexamination of US Patent No. 6,463,324—Amendment in Response to Official Action Dated Aug. 1, 2007 Filed Oct. 1, 2007 From the US Patent and Trademark Office Re.: U.S. Appl. No. 90/008,312.
Request for Ex Parte Reexamination of in Patent No. 6,463,324—Certificate of Reexamination Dated Apr. 29, 2008 From the US Patent and Trademark Office Re.: U.S. Appl. No. 90/008,312.
Request for Ex Parte Reexamination of US Patent No. 6,463,324—Official Action—Notice of Intent to Reexamine Dated Jan. 24, 2008 From the US Patent and Trademark Office Re.: U.S. Appl. No. 90/008,312.
Request for Ex Parte Reexamination of US Patent No. 6,463,324—Official Action Dated Aug. 1, 2007 From the US Patent and Trademark Office Re.: U.S. Appl. No. 90/008,312.
Request for Ex Parte Reexamination of US Patent No. 6,463,324—Official Action, Interview Summary and References Considered Dated Nov. 6, 2007 From the US Patent and Trademark Office Re.: U.S. Appl. No. 90/008,312.
Request for Ex Parte Reexamination of US Patent No. 6,463,324 Dated Nov. 1, 2006 From the US Patent and Trademark Office Re.: U.S. Appl. No. 90/008,312.
Response Dated Jul. 1, 2010 to Invitation Pursuant to Rule 62a(1) EPC and Rule 63(1) EPC of May 5, 2010 From the European Patent Office Re.: Application No. 04719312.3.
Response Dated Mar. 1, 2010 to Official Action of Aug. 28, 2009 From the US Patent and Trademark Office Re.: U.S. Appl. No. 11/932,064.
Response Dated Oct. 1, 2007 to Official Action of Aug. 1, 2007 From the US Patent and Trademark Office Re.: U.S. Appl. No. 90/008,312.
Response Dated Sep. 1, 2004 to Communication Pursuant to Article 96(2) EPC of Mar. 2, 2004 From the European Patent Office Re.: Application No. 97929478.2.
Response Dated Feb. 2, 2010 to Official Action of Dec. 2, 2009 From the US Patent and Trademark Office Re.: U.S. Appl. No. 11/932,149.
Response Dated Apr. 3, 2008 to Official Action of Jan. 3, 2008 From the US Patent and Trademark Office Re.: U.S. Appl. No. 10/116,201.
Response Dated Mar. 4, 2010 to Official Action of Nov. 5, 2010 From the US Patent and Trademark Office Re.: U.S. Appl. No. 10/549,216.
Response Dated May 4, 2009 to Official Action of Nov. 3, 2008 From the US Patent and Trademark Office Re.: U.S. Appl. No. 10/116,201.
Response Dated May 4, 2010 to Official Action of Jan. 5, 2010 From the US Patent and Trademark Office Re.: U.S. Appl. No. 11/802,685.
Response Dated Oct. 4, 2007 to Official Action of Sep. 4, 2007 From the US Patent and Trademark Office Re.: U.S. Appl. No. 95/000,032.
Response Dated Apr. 6, 2010 to Official Action of Oct. 6, 2009 From the US Patent and Trademark Office Re.: U.S. Appl. No. 11/550,560.
Response Dated May 6, 2010 to Office Action Dated Jan. 8, 2010 From the State Intellectual Property Office (SIPO) of the People's Republic of China Re.: Application No. 200480012687.5.
Response Dated Feb. 7, 2010 to Official Action of Dec. 2, 2009 From the US Patent and Trademark Office Re.: U.S. Appl. No. 11/932,149.
Response Dated Feb. 7, 2010 to Official Action of Nov. 3, 2009 From the US Patent and Trademark Office Re.: U.S. Appl. No. 11/931,724.
Response Dated Feb. 9, 2010 to Official Action of Oct. 8, 2009 From the US Patent and Trademark Office Re.: U.S. Appl. No. 10/116,201.
Response Dated Oct. 12, 2010 to Official Action of Jun. 11, 2010 From the US Patent and Trademark Office Re.: U.S. Appl. No. 11/932,064.
Response Dated Dec. 13, 2010 to Official Action of Jun. 11, 2010 From the US Patent and Trademark Office Re.: U.S. Appl. No. 11/550,560.

Response Dated Dec. 13, 2010 to Official Action of Oct. 13, 2010 From the US Patent and Trademark Office Re.: U.S. Appl. No. 11/919,491.
Response Dated Jul. 13, 2010 to Notice of Reasons for Rejection of Apr. 27, 2010 From the Japanese Patent Office Re.: Application No. 2007-206282.
Response Dated Oct. 13, 2010 to Official Action of Apr. 30, 2010 From the US Patent and Trademark Office Re.: U.S. Appl. No. 11/932,149.
Response Dated Mar. 15, 2010 to Official Action of Sep. 14, 2009 From the US Patent and Trademark Office Re.: U.S. Appl. No. 11/931,889.
Response Dated Jan. 17, 2008 to Official Action of Jul. 18, 2007 From the US Patent and Trademark Office Re.: U.S. Appl. No. 10/039,845.
Response Dated Apr. 20, 2006 to Communication Pursuant ot Article 96(2) EPC of Nov. 2, 2005 From the European Patent Office Re.: Application No. 97929478.2.
Response Dated Aug. 20, 2008 to Official Action of Jun. 20, 2008 From the US Patent and Trademark Office Re.: U.S. Appl. No. 90/008,689.
Response Dated Sep. 20, 2010 to Official Action of May 21, 2010 From the US Patent and Trademark Office Re. U.S. Appl. No. 10/116,201.
Response Dated May 21, 2008 to Office Action of Dec. 11, 2007 From the Japanese Patent Office Re.: Application No. 09-525055.
Response Dated Nov. 22, 2009 to Official Action of Jun. 1, 2009 From the US Patent and Trademark Office Re.: U.S. Appl. No. 10/039,845.
Response Dated Nov. 22, 2010 to Official Action of Jul. 21, 2010 From the US Patent and Trademark Office Re.: U.S. Appl. No. 11/802,685.
Response Dated Dec. 24, 2006 to Office Action of Jul. 18, 2006 From the Japanese Patent Office Re.: Application No. 10-513446.
Response Dated Dec. 25, 2006 to Notice of Reasons for Rejection of Jul. 18, 2006 From the Japanese Patent Office Re.: Application No. 09-529637.
Response Dated Oct. 28, 2010 to Official Action of Jun. 28, 2010 From the US Patent and Trademark Office Re.: U.S. Appl. No. 11/931,889.
Response Dated Sep. 30, 2010 to Official Action of Apr. 30, 2010 From the US Patent and Trademark Office Re.: U.S. Appl. No. 11/931,724.
Response in Conjunction With an RCE Dated May 4, 2010 to Official Action Dated Feb. 4, 2010 From the US Patent and Trademark Office Re.: U.S. Appl. No. 10/039,845.
Summons to Attend Oral Proceedings Pursuant to Rule 115(1) EPC Dated Dec. 22, 2008 From the European Patent Office Re.: Application No. 97929480.8.
Supplementary European Search Report and the European Search Opinion Dated Nov. 28, 2008 From the European Patent Office Re.: Application No. 006759102.4.
Supplementary European Search Report and the European Search Opinion Dated Nov. 28, 2008 From the European Patent Office Re.: Application No. 05853465.2.
Supplementary Partial European Search Report Dated Nov. 4, 2010 From the European Patent Office Re. Application No. 04719312.3.
Translation of Notice of Reasons for Rejection Dated Jul. 18, 2006 From the Japanese Patent Office Re.: Application No. 9-529637.
Translation of Notice of Reasons for Rejection Dated Apr. 27, 2010 From the Japanese Patent Office Re.: Application No. 2007-206282.
Adeghate et al. "Effect of Electrical Field Stimulation on Insulin and Glucagon Secretion From the Pancreas of Normal and Diabetic Rats", Hormone and Metabolic Research, 33(5): 281-289, May 2001. Abstract.
Bergsten et al. "Synchronous Oscillations of Cytoplasmic Ca2+ and Insulin Release in Glucose-Stimulated Pancreatic Islets", The Journal of Biological Chemistry, 269(12): 8749-8753, Mar. 25, 1994.
Blank et al. "Initial Interactions in Electromagnetic Field-Induced Biosynthesis", Journal of Cellular Physiology, 199: 359-363, 2004.
Burfeind et al "The Effects of Mechanical Cardiac Stabilization on Left Ventricular Performance", Europeari Journal of Cardio-Thoracic Surgery, 14: 285-289, 1998.
Devedeux et al. "Uterine Electromyography: A Critical Review", American Journal of Obstetric Gynecology, 169(6): 1636-1653, 1993.
Fromer et al. "Ultrarapid Subthreshold Stimulation for Termination of Atriventricular Node Reentrant Tachycardia", Journal of the American College Cardiology, 20: 879-883, 1992.
Gardner "Natriuretic Peptides: Markers or Modulators of Cardiac Hypertrophy?", Trends in Endocrinology and Metabolism, 14(9): 411-416, Nov. 2003.
Gilmour Jr. et al. "Dynamics of Circus Movement Re-Entry Across Canine Purkinje Fibre-Muscle Junctions", The Journal of Physiology, 476(3): 473-485, 1994.
Gilmour Jr. et al. "Overdrive Suppression of Conduction at the Canine Purkinje-Muscle Junction", Circulation, 76(6): 1388-1396, 1987.
Gold et al. "Evidence That Glucose 'Marks' Beta Cells Resulting in Preferential Release of Newly Synthesized Insulin", Science, 218(4567): 56-58, Oct. 1, 1982. Abstract.
Gomis et al. "Oscillatory Patterns of Electrical Activity in Mouse PancreaticIslets of Langerhans Recorded in Vivo", Pfl?gers Archiv European Journal of Physiology, 432(3): 510-515, 1996.
Gussoni et al. "Dystrophin Expression in the MDX Mouse Restored by Stem Cell Transplantation", Nature, 401(6751): 390-394, 1999.
Highfill et al. "Large-Scale Production of Murine Bone Marrow Cells in an Airlift Packed Bed Bioreactor", Biotechnology and Bioengineering, 50(5): 514-520, 1996.
Hinke et al. "Dipeptidyl Peptidase IV (DPIV/CD26) Degradation of Glucagon. Characterization of Glucagon Degradation Products and DPIV-Resistant Analogs", The Journal of Biological Chemistry, 275(6): 3827-3834, Feb. 11, 2000.
Jaremko et al. "Advances Towards the Implantable Artifical Pancreas for Treatment of Diabetes", Diabetes Care, 21(3): 444-450, 1998.
Kurose et al. "Glucagon, Insulin and Somatostatin Secretion in Response to Sympathetic Neural Activation in Streptozotocin-Induced Diabetic Rats. A Study With the Isolated Perfused Rat Pancreas In Vitro", Diabetologia, 35(11): 1035-1041, Nov. 1992. Abstract.
Luiken et al. "Contraction-Induced Fatty Acid Translocase/CD36 Translocation in Rat Cardiac Myocytes Is Mediated Through AMP-Activated Protein Kinase Signaling", Diabetes, 52: 1627-1634, 2003.
Meurer et al. "Properties of Native and in Vitro Glycosylated Forms of the Glucogan-Like Peptide-1 Receptor Antagonist Exendin(9-39)", Metabolism: Clinical and Experimental, 48(6): 716-724, Jun. 1999. Abstract.
Misler et al. "Electrophysiology of Stimulus-Secretion Coupling in Human Beta-Cells", Diabetes, 41(10): 1221-1228, Oct. 1992. Abstract.
Nadal et al. "Homologous and Heterologous Asynchronicity Between Identified ?-, ?- and ?- Cells Within Intact Islets of Langerhans in the Mouse", Journal of Physiology, 517(Pt.1): 85-93, 1999.
Ohinata et al. "Proadrenomedullin N-Terminal 20 Peptide (PAMP) Elevates Blood Glucose Levels Via Bombesin Receptor in Mice", FEBS Letters, 473(2): 207-211, May 2000. Abstract.
P?rksen et al. "Section 6: Pulsatile and Phasic Insulin Release in Normal and Diabetic Man. Pulsatile Insulin Secretion: Detection, Regulation, and Role in Diabetes", Diabetes, 51(Suppl.1): S245-S254, Feb. 2002.
Palti et al. "Islets of Langerhans Generate Wavelike Electric Activity Modulated by Glucose Concentration", Diabetes, 45(5): 595-601, May 1996. Abstract.
Patterson et al. "Therapeutic Angiogenesis: The New Electrophysiology?", Circulation, 99(20): 2614-2616, 1999.
Pokrovsky et al. "Physiology of Man", 1: 82-83, 94, 2: 42, 54.
Rivera et al. "Regulation of Protein Secretion Through Controlled Aggregation in the Endoplasmic Reticulum", Science, 287(5454): 826-830, Feb. 4, 2000. Abstract.
Sakuma et al. "A Model Analysis of Aftereffects of High-Intensity DC Stimulation on Action Potential of Ventricular Muscle", IEEE Transactions on Biomedical Engineering, 45(2): 258-267, 1998, Abstract.
San Mauro et al. "Nerves of the Heart: A Comprehensive Review With a Clinical Point of View", Neuroanatomy, 8: 28-31, 2009.

Schirra et al. "Exendin(9-39) Amide Is an Antagonist of Glucagon-Like Peptide-1(7-36) Amide in Humans", Journal of Clinical Investigation, 101(7): 1421-1430, Apr. 1998.

Schirra et al. "Mechanisms of the Antidiabetic Action of Subcutaneous Glucagon-Like Peptide-1 (17-36) Amide in Non-Insulin Dependent Diabetes Mellitus", Journal of Endocrinology Ltd., 156(1): 177-186, Jan 1998. Abstract.

Serre et al. "Exendin-(9-39) Is an Inverse Agonist of the Murine Glucagon-Like Peptide-1 Receptor: Implications for Basal Intracellular Cyclic Adenosine 3',5'-Monophosphate Levels and ?-Cells Glucose Competence", Endocrinology, 139(11): 4448-4454, 1998.

Shah et al. "Impact of Lack of Suppression of Glucagon on Glucose Tolerance in Humans", American Journal of Physiology, AJP—Endocrinology and Metabolism, 277(2 Pt.1): E283-E290, 1999.

Shmit et al. "Physiology of Man", Moscow Medicine, Mir, 1: 78, 1996.

Shuba et al. "Physiology of Vessel Smooth Muscles", Kiev Naukova Dumka, 142: 11-15, 142, 1988.

Singh et al. "Effects of Islet Hormones on Nerve-Mediated and Acetylcholine-Evoked Secretory Responses in the Isolated Pancreas of Normal and Diabetic Rats", International Journal of Molecular Medicine, 1(3): 627-634, Mar. 1998. Abstract.

Soria et al. "Cytosolic Calcium Oscillations and Insulin Release in Pancreatic Islets of Langerhans", Diabetes & Metabolism, 24: 37-40, 1998.

Sukhorukov et al. "The Effect of Electrical Deformation Forces on the Electropermeabilization of Erythrocyte Membranes in Low-and High-Conductivity Media", The Journal of Membrane Biology, 163(3): 235-245, 1998. Abstract.

Swerdlow et al. "Cardiovascular Collapse Caused by Electrocardiographically Silent 60-Hz Intracardiac Leakage Current: Implications for Electrical Safety", Circulation, 99: 2559-2564, 1999.

Todd et al. "Subcutaneous Glucagon-Like Peptide I Improves Postprandial Glycaemic Control Over a 3-Week Period in Patients With Early Type 2 Diabetes", Clinical Science, 95: 325-329, 1998.

Valdeolmillos et al. "In Vivo Synchronous Membrane Potential Oscillations in Mouse Pancreatic Beta-Cells: Lack of Co-Ordination Between Islets", Journal of Physiology, 493(1): 9-18, 1996.

Van Riper et al. "Electrical Field Stimulation-Mediated Relaxation of a Rabbit Middle Cerebral Artery. Evidence of a Cholinergic Endothelium-Dependent Component", Circulation Research, 70(6): 1104-1112, Jun. 1992.

Wang et al. "Islet Amyloid Polypeptide Tonally Inhibits ?-, ?-, and ?-Cell Secretion in isolated Rat Pancreatic Islets", American Journal of Physiology, AJP—Endocrinology and Metabolism, 276(1 Pt.1): E19-E24, 1999.

Wright et al. "Structure of Fab hGR-2 F6, A Competitive Antagonist of the Glucagon Receptor", Acta Crystallographica, Section D, Biological Crystallography, 56(Pt.5): 573-580, May 2000. Abstract.

Yonemura et al. "Amelioration of Diabetes Mellitus in Partially Depancreatized Rats by Poly(ADP-Ribose) Synthetase Inhibitors. Evidence of Islet B-Cell Regeneration", Diabetes, 33(4): 401-404, Apr. 1984. Abstract.

Zhou et al. "Prevention of Action Potentials During Extracellular Electrical Stimulation of Long Duration", Journal of Cardiovascular & Electrophysiology, 8(7): 779-789, 1997. Abstract.

Official Action Dated Feb. 17, 2012 From the US Patent and Trademark Office Re.: U.S. Appl. No. 11/932,149.

Response Dated Jul. 25, 2011 to Official Action Dated Jan. 24, 2011 From the US Patent and Trademark Office Re.: U.S. Appl. No. 11/919,491.

Official Action Dated Nov. 8, 2011 From the US Patent and Trademark Office Re.: U.S. Appl. No. 11/931,889.

Official Action Dated Mar. 22, 2011 From the US Patent and Trademark Office Re. U.S. Appl. No. 11/886,154.

Response Dated Apr. 10, 2011 to Official Action of Jan. 6, 2011 From the US Patent and Trademark Office Re.: U.S. Appl. No. 11/931,724.

\* cited by examiner

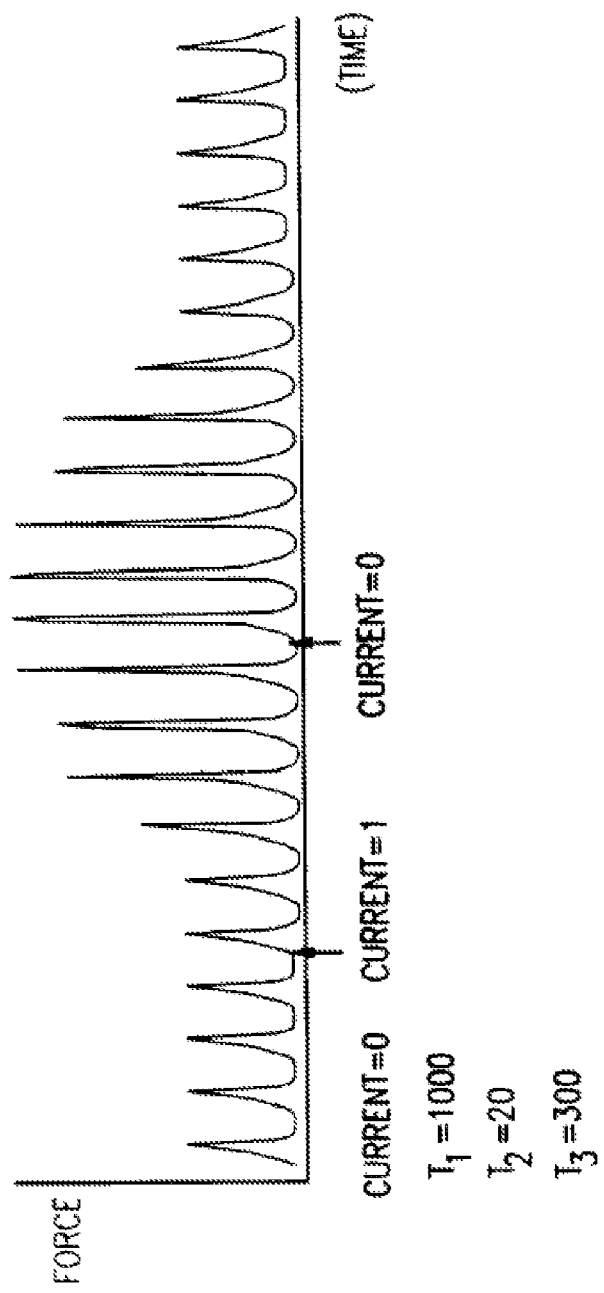

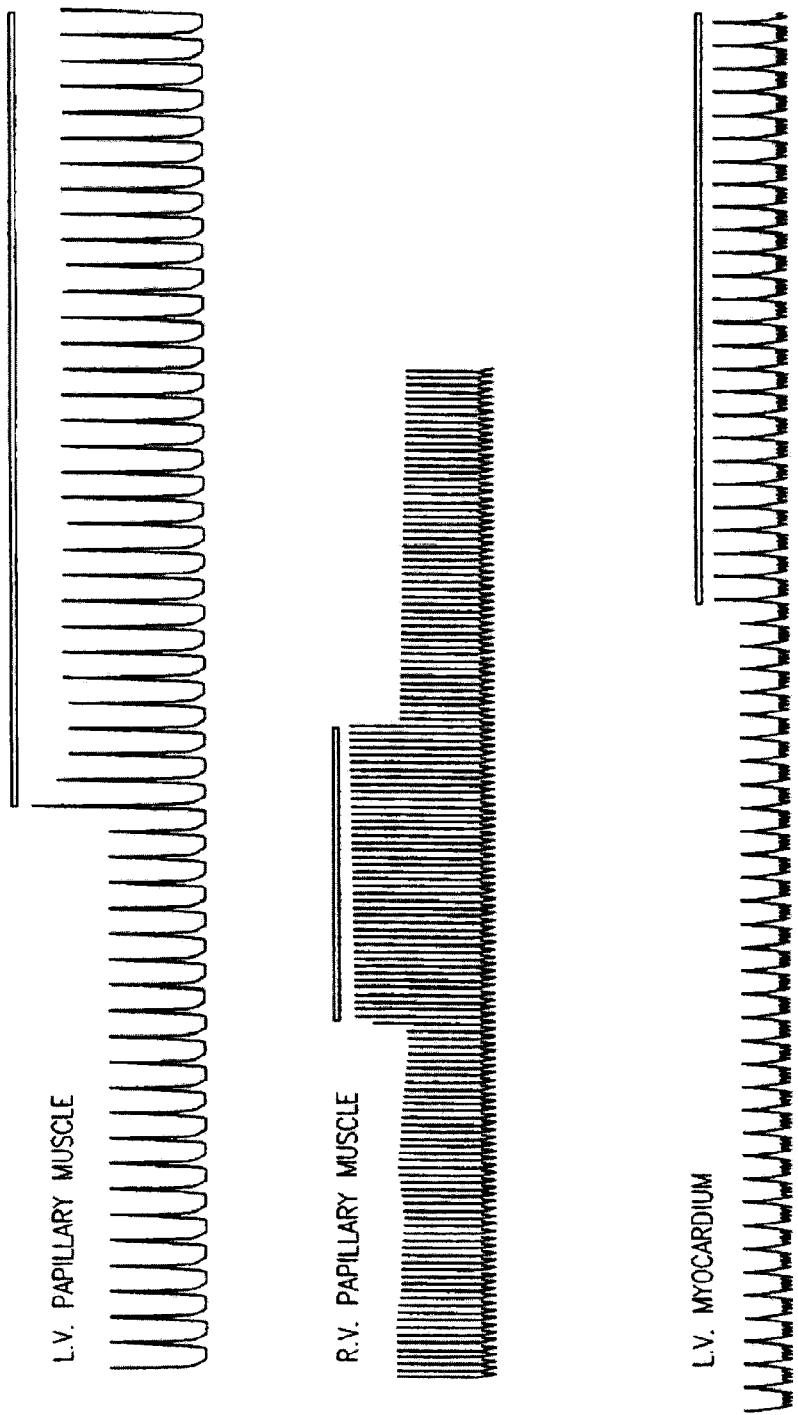

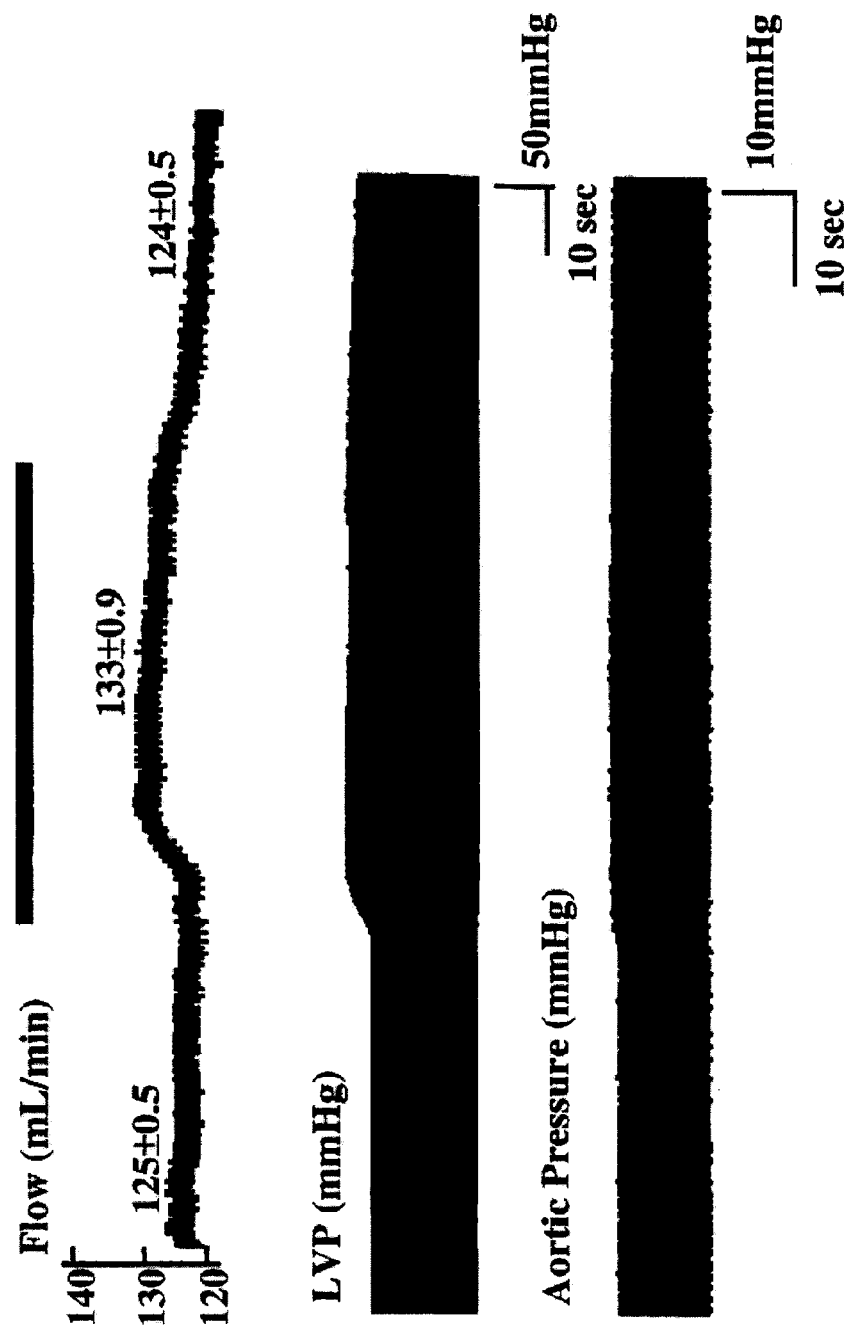

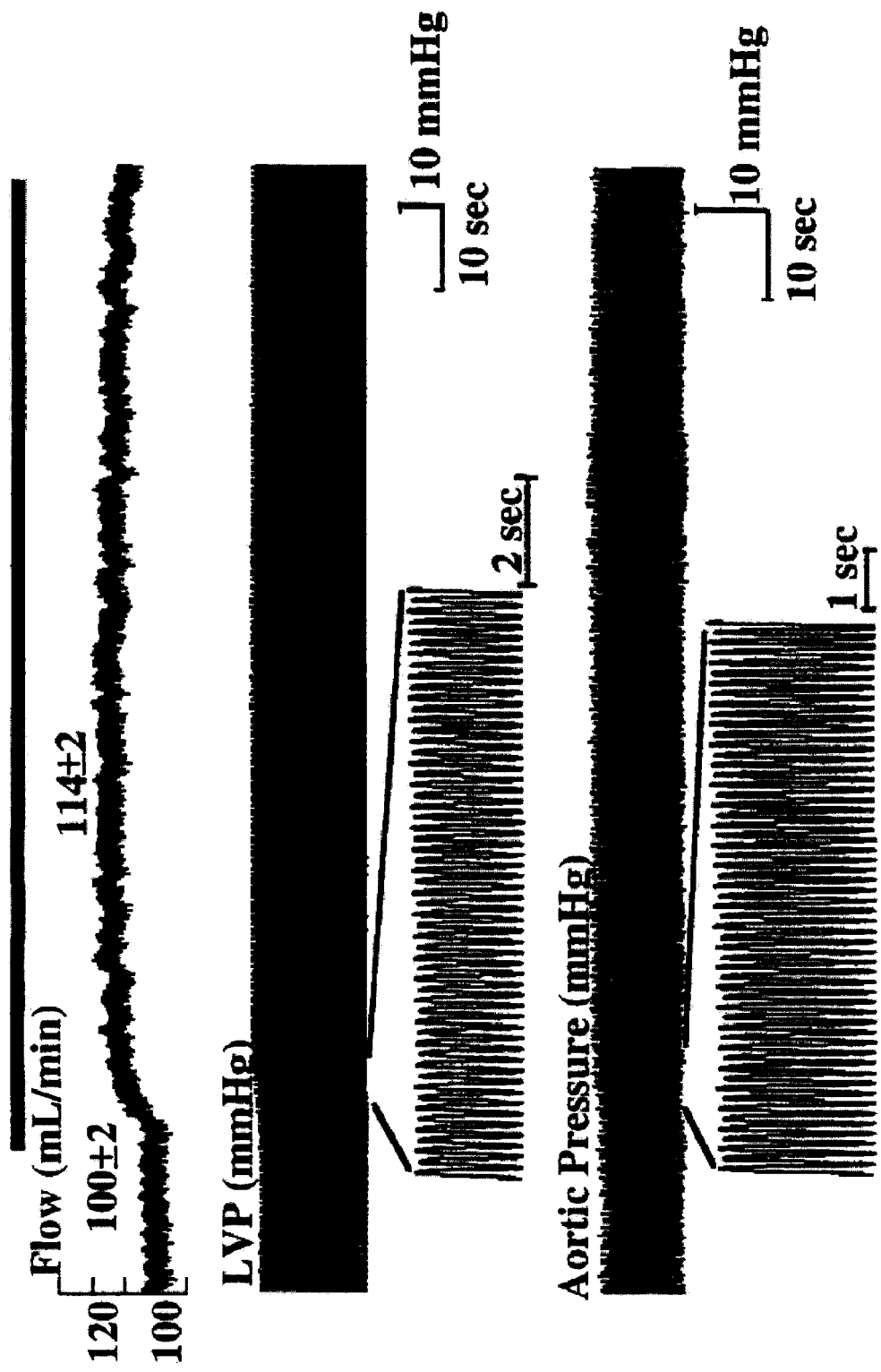

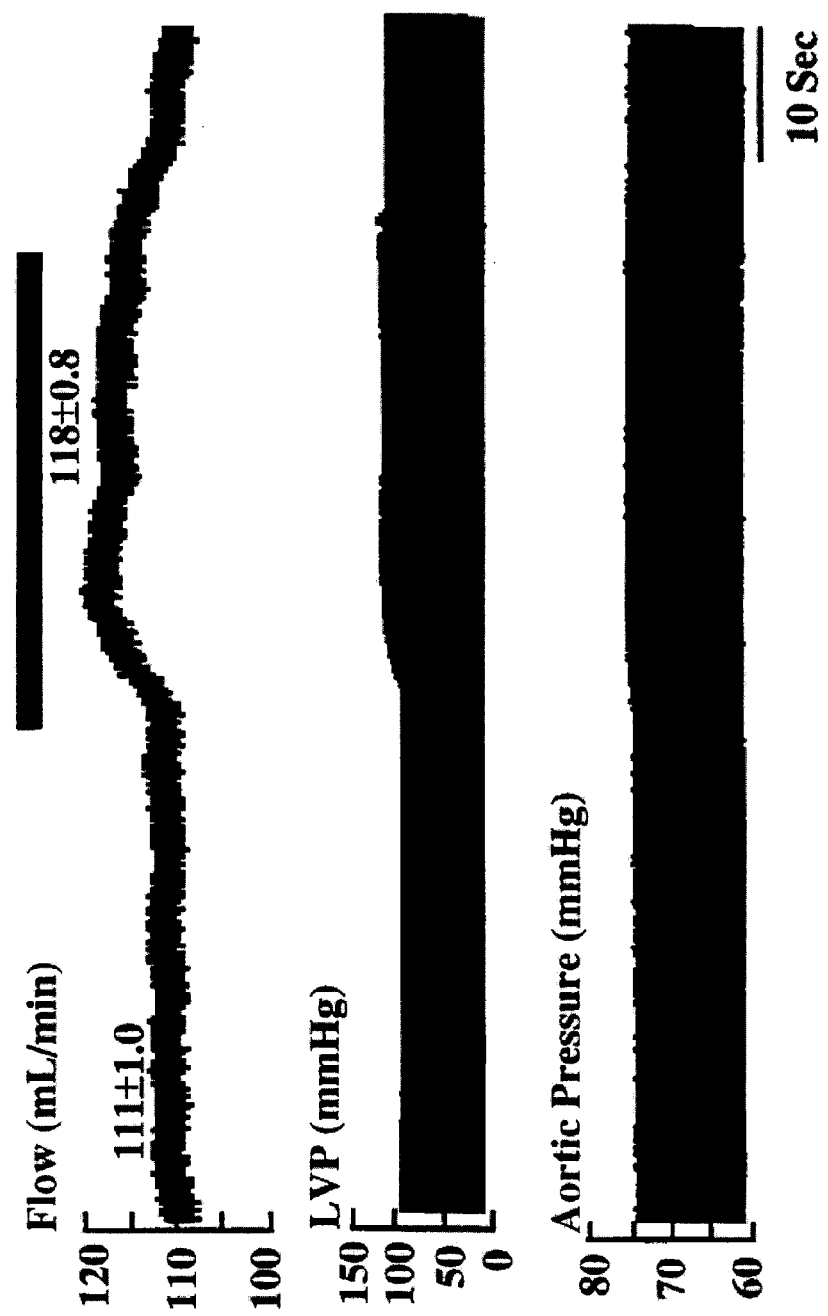

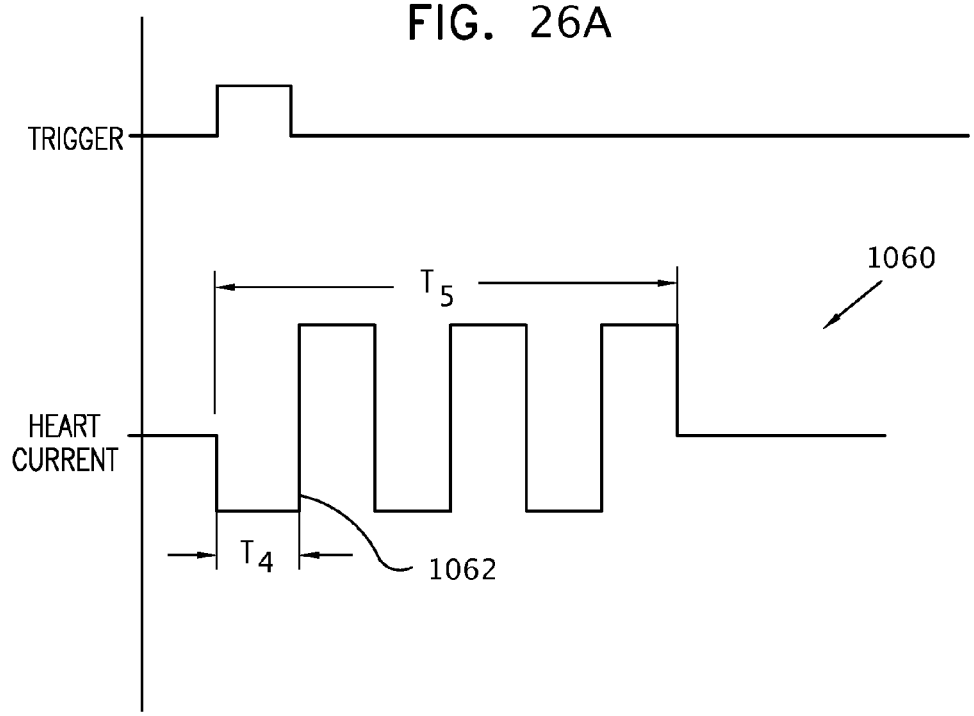
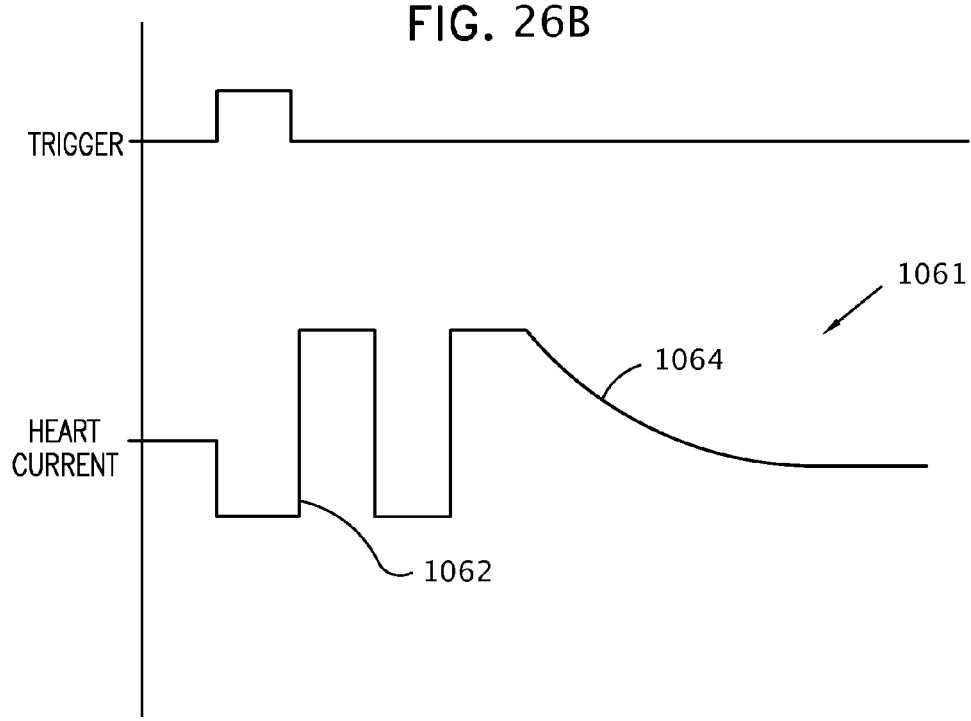

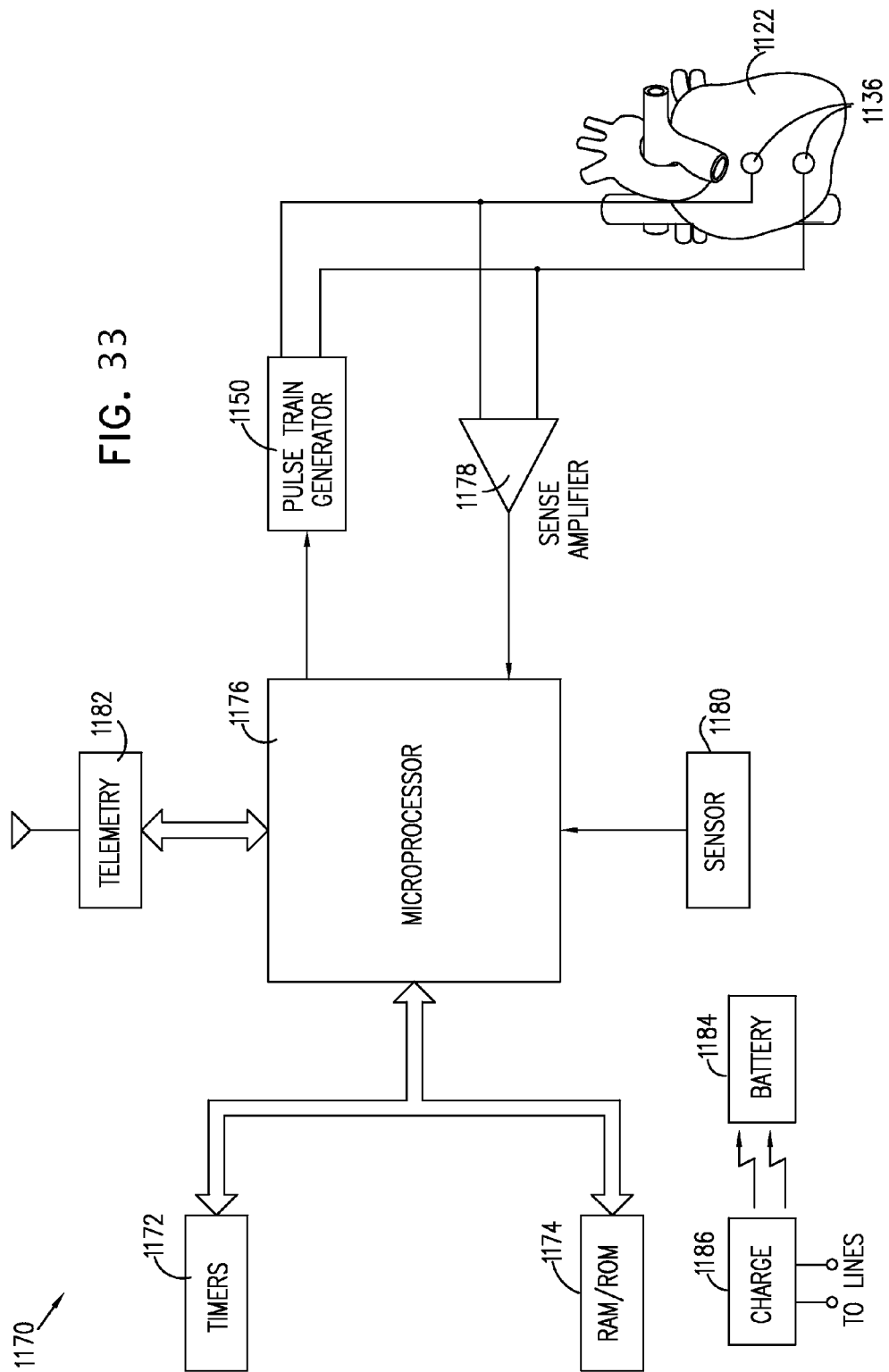

US 8,321,013 B2

ELECTRICAL MUSCLE CONTROLLER AND PACING WITH HEMODYNAMIC ENHANCEMENT

CROSS-REFERENCES TO RELATED APPLICATIONS

The present application is:

(a) a continuation-in-part of U.S. patent Ser. No. 09/720,639, now U.S. Pat. No. 7,460,907, entitled "Pacing with hemodynamic enhancement," filed May 16, 2001, which is a US national phase of PCT Patent Application PCT/IL99/00392, published as WO2000/004947, entitled "Pacing with hemodynamic enhancement," filed Jul. 18, 1999, which claims priority from Israel Patent Application 125,424, entitled "Pacing with hemodynamics enhancement," filed Jul. 20, 1998, abandoned; and (b) a continuation-in-part of commonly assigned U.S. patent application Ser. No. 11/550,560, published as U.S. 2007-0088393, entitled "Electrical muscle controller," filed Oct. 18, 2006, pending, which is a continuation of commonly assigned U.S. patent application Ser. No. 10/866,213, entitled "Electrical muscle controller," filed Jun. 10, 2004 (now U.S. Pat. No. 7,167,748), which is a continuation of commonly assigned U.S. patent application Ser. No. 10/001,710, entitled "Electrical muscle controller," filed Oct. 31, 2001 (now U.S. Pat. No. 7,062,318), which is a continuation of U.S. patent application Ser. No. 09/723,989, entitled "Electrical muscle controller using a non-excitatory electric field," filed Nov. 28, 2000 (now U.S. Pat. No. 6,330,476), which is a continuation of commonly assigned U.S. patent application Ser. No. 09/101,723, entitled "Electrical muscle controller using a non-excitatory electric field," filed Aug. 13, 1998, (now U.S. Pat. No. 6,317,631), which is a US national phase of PCT Patent Application PCT/IL97/00012, published as WO1997/025098, entitled "Electrical muscle controller," filed Jan. 8, 1997, which is related to the following US and Israeli applications, the disclosures of which are also incorporated herein by reference:

(1) U.S. Provisional Patent Application 60/009,769, entitled "Cardiac Electromechanics," filed Jan. 11, 1996;
(2) Israel Patent Application 116,699, entitled "Cardiac Electromechanics," filed Jan. 8, 1996;
(3) U.S. Provisional Patent Application 60/011,117, entitled "Electrical Muscle Controller," filed Feb. 5, 1996;
(4) Israeli Patent Application 119,261, entitled "Electrical Muscle Controller," filed Sep. 17, 1996;
(5) U.S. Provisional Patent Application 60/026,392, entitled "Electrical Muscle Controller," filed Sep. 16, 1996; and
(6) U.S. patent application Ser. No. 08/595,365, entitled "Cardiac electromechanics," filed Feb. 1, 1996, (now U.S. Pat. No. 5,738,096).

The disclosures of all aforementioned patents and patent applications are incorporated herein by reference.

FIELD OF THE INVENTION

The present invention relates generally to cardiac therapeutic devices, and specifically to cardiac pacemakers. The present invention additionally relates to cardiac muscular control, in particular control using non-excitatory electrical signals.

BACKGROUND OF THE INVENTION

The heart is a muscular pump whose mechanical activation is controlled by electrical stimulation generated at a right atrium and passed to the entire heart. In a normal heart, the electrical stimulation that drives the heart originates as action potentials in a group of pacemaker cells lying in a sino-atrial (SA) node in the right atrium. These action potentials then spread rapidly to both right and left atria. When the action potential reaches an unactivated muscle cell, the cell depolarizes (thereby continuing the spread of the action potential) and contracts. The action potentials then enter the heart's conduction system and, after a short delay, spread through the left and right ventricles of the heart. It should be appreciated that activation signals are propagated within the heart by sequentially activating connected muscle fibers. Each cardiac muscle cell generates a new action potential for stimulating the next cell, after a short delay and in response to the activation signal which reaches it. Regular electrical currents can be conducted in the heart, using the electrolytic properties of the body fluids, however, due the relatively large resistance of the heart muscle, this conduction cannot be used to transmit the activation signal.

In a muscle cell of a cardiac ventricle, the resting potential across its cellular membrane is approximately $-90$ mV (millivolts) (the inside is negatively charged with respect to the outside). FIG. 1A shows a transmembrane action potential of a ventricle cardiac muscle cell during the cardiac cycle. When an activation signal reaches one end of the cell, a depolarization wave rapidly advances along the cellular membrane until the entire membrane is depolarized, usually to approximately $+20$ mV (23). Complete depolarization of the cell membrane occurs in a very short time, about a few millisecond. The cell then rapidly (not as rapid as the depolarization) depolarizes by about 10 mV. After the rapid depolarization, the cell slowly repolarizes by about 20 mV over a period of approximately 200 to 300 msec (milliseconds), called the plateau (25 in FIG. 1A). It is during the plateau that the muscle contraction occurs. At the end of the plateau, the cell rapidly repolarizes (27 in FIG. 1A) back to its resting potential (21 in FIG. 1A). Different cardiac muscle cells have different electrical characteristics, in particular, cells in an SA node do not have a substantial plateau and do not reach as low a resting potential as ventricular cells.

In the following discussion, it should be appreciated that the exact mechanisms which govern action potentials and ionic pumps and channels are only partly known. Many theories exist and the field in is a constant state of flux.

The electrical activity mirrors chemical activity in a cell. Before depolarization (at resting), the concentration of sodium ions inside the cell is about one tenth the concentration in the interstitial fluid outside the cell. Potassium ions are about thirty-five times more concentrated inside the cell than outside. Calcium ions are over ten thousand times more concentrated outside the cell than inside the cell. These concentration differentials are maintained by the selective permeability of the membrane to different ions and by ionic pumps in the membrane of the cell which continuously pump sodium and calcium ions out and potassium ions in. One result of the concentration differences between the cell and the external environment is a large negative potential inside the cell, about 90 mV as indicated above.

When a portion of the cell membrane is depolarized, such as by an action potential, the depolarization wave spreads along the membrane. This wave causes a plurality of voltage-gated sodium channels to open. An influx of sodium through these channels rapidly changes the potential of the membrane from negative to positive (23 in FIG. 1A). Once the voltage becomes less negative, these channels begin to close, and do not open until the cell is again depolarized. It should be noted that the sodium channels must be at a negative voltage of at least a particular value in order to be primed for reopening. Thus, these channels cannot be opened by an activation potential before the cell has sufficiently repolarized. In most cells, the sodium channels usually close more gradually than they open. After the rapid depolarization, the membrane starts a fast repolarization process. The mechanism for the fast repolarization is not fully understood, although closing of the sodium channels appears to be an important factor. Following a short phase of rapid repolarization, a relatively long period (200 to 300 msec) of slow repolarization term the plateau stage (25 in FIG. 1A) occurs. During the plateau it is not believed to be possible to initiate another action potential in the cell, because the sodium channels are inactivated.

Two mechanisms appear to be largely responsible for the long duration of the plateau, an inward current of calcium ions and an outward current of potassium ions. Both currents flow with their concentration gradients, across the membrane. The net result is that the two types of current electrically subtract from each other. In general, the flow of potassium and calcium is many times slower than the flow of the sodium, which is the reason why the plateau lasts so long. According to some theories, the potassium channels may also open as a result of the action potential, however, the probability of a potassium channel opening is dependent on the potential. Thus, many channels open only after the depolarization of the cell is under way, or completed. Possibly, at least some of the potassium channels are activated by the calcium ions. In addition, some of the potassium channels are triggered by the repolarization of the membrane. The membrane permeability to potassium gradually increases, following its drop during the rapid depolarization (23 in FIG. 1A). The calcium channels also conduct sodium back into the cell, which helps extend the plateau duration.

The inward calcium current during the normal cardiac action potential contributes to the action potential plateau and is also involved in the contractions (directly and/or indirectly) in the cardiac muscle cells. In a process termed calcium induced calcium release, the inward current of calcium induces the release of calcium ions stored in intracellular calcium stores (probably the sacroplasmic reticulum). The existence and importance of a physical link between the reticulum and the calcium channels in cardiac muscle is unclear. However, the response curve of these calcium stores may be bell-shaped, so that too great an influx of calcium may reduce the amount of available calcium relative to amount made available by a smaller influx.

In single cells and in groups of cells, time is required for cells to recover partial and full excitability during the repolarization process. While the cell is repolarizing (25, 27 in FIG. 1A), it enters a state of hyper polarization, during which the cell cannot be stimulated again to fire a new action potential. This state is called the refractory period. The refractory period is divided into two parts. During an absolute refractory period, the cell cannot be re-excited by an outside stimulus, regardless of the voltage level of the stimulus. During a relative refractory period, a much larger than usual stimulus signal is required to cause the cell to fire a new action potential. The refractory state is probably caused by the sodium channels requiring priming by a negative voltage, so the cell membrane cannot depolarize by flow of sodium ions until it is sufficiently repolarized. Once the cell returns to its resting potential (21 in FIG. 1A), the cell may be depolarized again.

In an experimental methodology called voltage clamping, an electrical potential is maintained across at least a portion of a cell membrane to study the effects of voltage on ionic channels, ionic pumps and on the reactivity of the cell.

It is known that by applying a positive potential across the membrane, a cell may be made more sensitive to a depolarization signal. Some cells in the heart, such as the cells in the SA node (the natural pacemaker of the heart) have a resting potential of about −55 mV. As a result, their voltage-gated sodium channels are permanently inactivated and the depolarization stage (23 in FIG. 1A) is slower than in ventricular cells (in general, the action potential of an SA node cell is different from that shown in FIG. 1A). However, cells in the SA node have a built-in leakage current, which causes a self-depolarization of the cell on a periodic basis. In general it appears that when the potential of a cell stay below about −60 mV for a few msec, the voltage-gated sodium channels are blocked. Applying a negative potential across its membrane make a cell less sensitive to depolarization and also hyperpolarizes the cell membrane, which seems to reduce conduction velocity.

In modern cardiology, many parameters of the heart's activation can be controlled. Pharmaceuticals can be used to control the conduction velocity, excitability, contractility and duration of the refractory periods in the heart. These pharmaceuticals may be used to treat arrhythmias and prevent fibrillations. A special kind of control can be achieved using a pacemaker. A pacemaker is an electronic device which is typically implanted to replace the heart's electrical excitation system or to bypass a blocked portion of the conduction system. In some types of pacemaker implantation, portions of the heart's conduction system, for example an atrial-ventricle (AV) node, must be ablated in order for the pacemaker to operate correctly.

Another type of cardiac electronic device is a defibrillator. As an end result of many diseases, the heart may become more susceptible to fibrillation, in which the activation of the heart is substantially random. A defibrillator senses this randomness and resets the heart by applying a high voltage impulse(s) to the heart.

Pharmaceuticals are generally limited in their effectiveness in that they affect both healthy and diseased segments of the heart, usually, with a relatively low precision. Electronic pacemakers, are further limited in that they are invasive, generally require destruction of heart tissue and are not usually optimal in their effects. Defibrillators have substantially only one limitation. The act of defibrillation is very painful to the patient and traumatic to the heart.

An article entitled "Electrical stimulation of cardiac myoctes," by Ravi Ranjan and Nitish V. Thakor, in Annals of Biomedical Engineering, Vol. 23, pp. 812 821, published by the Biomedical Engineering Society, 1995, the disclosure of which is incorporated herein by reference, describes several experiments in applying electric fields to cardiac muscle cells. These experiments were performed to test theories relating to electrical defibrillation, where each cell is exposed to different strengths and different relative orientations of electric fields. One result of these experiments was the discovery that if a defibrillation shock is applied during repolarization, the repolarization time is extended. In addition, it was reported that cells have a preferred polarization. Cardiac muscle cells tend to be more irregular at one end of the cell than at the other end of the cell. It is theorized in the article, that local "hot spots" of high electrical fields are generated at the irregular end sites and that these "hot spots" are the sites of initial depolarization within the cell, since it is at these sites that the threshold for depolarization is first reached. This theory also explains that cells are more sensitive to electric fields in their longitudinal direction than in their transverse direction, since the irregularities are concentrated at the cell ends. In addition, the asymmetric irregularity of the cells may explain results which showed a preferred polarity of the applied electric field.

The electrical activation of skeletal muscle cells is similar to that of cardiac cells, in that a depolarization event induces contraction of muscle fibers. However, skeletal muscle is divided into isolated muscle bundles, each of which is individually innervated by action potential generating nerve cells. Thus, the effect of an action potential in skeletal muscle is local, while in a cardiac muscle (where all the muscle cells are electrically connected), an action potential is transmitted to the entire heart from a single location of action potential generation. In addition, the chemical aspects of activation of skeletal muscle is somewhat different from those of cardiac muscle.

An article entitled "Muscle recruitment with infrafascicular electrodes", by Nicola Nannini and Kenneth Horch, IEEE Transactions on Biomedical Engineering, Vol. 38, No. 8, pp. 769-776, August 1991, the disclosure of which is incorporated herein by reference, describes a method of varying the contractile force of skeletal muscles, by "recruiting" a varying number of muscle fibers. During the recruiting, the contractile force of a muscle is determined by the number of muscle fibers which are activated by a stimulus.

However, it is generally accepted that cardiac muscle fibers function as a syncytium such that each and every cell contracts at each beat. Thus, there are no cardiac muscles fibers available for recruitment (described in an article entitled "Excitation contraction coupling and cardiac contractile force", by Donald M. Bers, Chapter 2, page 17, Kluwer Academic, 1991, the disclosure of which is incorporated herein by reference). This citation also states that in cardiac muscle cells, contractile force is varied in large part by changes in peak calcium.

An article entitled "Effect of field stimulation on cellular repolarization in rabbit myocardium", by Stephen B. Knisley, William M. Smith and Raymond E. Ideker, Circulation Research, Vol. 70, No. 4, pp. 707 715, April 1992, the disclosure of which is incorporated herein by reference, describes the effect of an electrical field on rabbit myocardium. In particular, this article describes prolongation of an action potential as a result of a defibrillation shock and ways by which this effect can cause defibrillation to fail. One hypothesis is that defibrillation affects cardiac cells by exciting certain cells which are relatively less refractory than others and causes the excited cells to generate a new action potential, effectively increasing the depolarization time.

An article entitled "Optical recording in the rabbit heart show that defibrillation strength shocks prolong the duration of depolarization and the refractory period", by Stephen M. Dillon, Circulation Research, Vol. 69, No. 3, pp. 842 856, September, 1991, the disclosure of which is incorporated herein by reference, explains the effect of prolonged repolarization as caused by the generation of a new action potential in what was thought to be refractory tissue as a result of the defibrillation shock. This article also proves experimentally that such an electric shock does not damage the cardiac muscle tissue and that the effect of a second action potential is not due to recruitment of previously unactivated muscle fibers. It is hypothesized in this article that the shocks hyperpolarize portions of the cellular membrane and thus reactivate the sodium channels. In the experiments described in this article, the activity of calcium channels is blocked by the application of methoxy-veraparmil.

An article entitled "Electrical resistances of interstitial and microvascular space as determinants of the extracellular electrical field and velocity of propagation in ventricular myocardium", by Johannes Fleischhauer, Lilly Lehmann and Andre G. Kleber, Circulation, Vol. 92, No. 3, pp. 587 594, Aug. 1, 1995, the disclosure of which is incorporated herein by reference, describes electrical conduction characteristics of cardiac muscle.

An article entitled "Inhomogeneity of cellular activation time and Vmax in normal myocardial tissue under electrical field stimulation", by Akihiko Taniguchi, Junji Toyama, Itsuo Kodama, Takafumi Anno, Masaki Shirakawa and Shiro Usui, American Journal of Physiology, Vol. 267 (Heart Circulation Physiology, Vol. 36), pp. H694-H705, 1994, the disclosure of which is incorporated herein by reference, describes various interactions between electro-tonic currents and action potential upstrokes.

An article entitled "Effect of light on calcium transport in bull sperm cells", by R. Lubart, H. Friedmann, T. Levinshal, R. Lavie and H. Breitbart, Journal of Photochemical Photobiology B, Vol. 14, No. 4, pp. 337 341, Sep. 12, 1992, the disclosure of which is incorporated herein by reference, describes an effect of light on bull sperm cells, in which laser light increases the calcium transport in these cells. It is also known that low level laser light affects calcium transport in other types of cells, for example as described in U.S. Pat. No. 5,464,436, the disclosure of which is incorporated herein by reference.

The ability of electromagnetic radiation to affect calcium transport in cardiac myocytes is well documented. Loginov V A, "Accumulation of calcium ions in myocardial sarcoplasmic reticulum of restrained rats exposed to the pulsed electromagnetic field", in Aviakosm Ekolog Med, Vol. 26, No. 2, pp. 49 51, March April, 1992, the disclosure of which is incorporated herein by reference, describes an experiment in which rats were exposed to a 1 Hz field of between 6 and 24 mTesla. After one month, a reduction of 33 percent in the velocity of calcium accumulation was observed. After a second month, the accumulation velocity was back to normal, probably due to an adaptation mechanism.

Schwartz J L, House D E, and Mealing G A, in "Exposure of frog hearts to CW or amplitude-modulated VHF fields: Selective efflux of calcium ions at 16 Hz", Bioelectromagnetics, Vol. 11, No. 4, pp. 349 358, 1990, the disclosure of which is incorporated herein by reference, describe an experiment in which the efflux of calcium ions in isolated frog hearts was increased by between 18 and 21% by the application of a 16 Hz modulated VHF electromagnetic field.

Lindstrom E, Lindstrom P, Berglund A, Lundgren E, and Mild K H, in "Intracellular calcium oscillations in a T-cell line after exposure to extremely-low-frequency magnetic fields with variable frequencies and flux densities", Bioelectromagnetics, Vol. 16, No. 1, pp. 41 47, 1995, the disclosure of which is incorporated herein by reference, describe an experiment in which magnetic fields, at frequency between 5 and 100 Hz (Peak at 50 Hz) and with intensities of between 0.04 and 0.15 mTesla affected calcium ion transport in T-cells.

Loginov V A, Gorbatenkova N V, and Klimovitskii Vla, in "Effects of an impulse electromagnetic field on calcium ion accumulation in the sarcoplasmatic reticulum of the rat myocardium", Kosm Biol Aviakosm Med, Vol. 25, No. 5, pp. 51 53, September October, 1991, the disclosure of which is incorporated herein by reference, describe an experiment in which a 100 minute exposure to a 1 msec impulse, 10 Hz frequency and 1-10 mTesla field produced a 70% inhibition of calcium transfer across the sarcoplasmic reticulum. The effect is hypothesized to be associated with direct inhibition of Ca-ATPase.

It should be noted that some researchers claim that low frequency magnetic fields do not have the above reported effects. For example, Coulton L A and Barker A T, in an article entitled "Magnetic fields and intracellular calcium: effects on lymphocytes exposed to conditions for Cyclotron Resonance", Phys Med Biol, Vol. 38, No. 3, pp. 347 360, March, 1993, the disclosure of which is incorporated herein by references, exposed lymphocytes to radiation at 16 and 50 Hz, for a duration of 60 minutes and failed to detect any changes in calcium concentration.

Pumir A, Plaza F, and Krinsky Vl, in an article entitled "Control of rotating waves in cardiac muscle: Analysis of the effect of electric fields", Proc R Soc Lond B Biol Sci, Vol. 257, No. 1349, pp. 129 34, Aug. 22, 1994, the disclosure of which is incorporated herein by reference, describe that an application of an external electric field to cardiac muscle affects conduction velocity by a few percent. This effect is due to the hyperpolarization of one end of muscle cells and a depolarization of the other end of the cell. In particular, an externally applied electric field favors propagation antiparallel to it. It is suggested in the article to use this effect on conduction velocity to treat arrhythmias by urging rotating waves, which are the precursors to arrhythmias, to drift sideways to non-excitable tissue and die.

An article entitled "Control of muscle contractile force through indirect high-frequency stimulation", by M. Sblomonow, E. Eldred, J. Lyman, and J. Foster, American Journal of Physical Medicine, Vol. 62, No. 2, pp. 71 82, April 1983, the disclosure of which is incorporated herein by reference, describes a method of controlling skeletal muscle contraction by varying various parameters of a 500 Hz pulse of electrical stimulation to the muscle.

A reference entitled "Biomedical engineering handbook", ed. Joseph D. Bronzino, chapter 82.4, page 1288, IEEE press/CRC press, 1995, which is incorporated herein by reference, describes the use of precisely timed subthreshold stimuli, simultaneous stimulation at multiple sites and pacing with elevated energies at the site of a tachycardia foci, to prevent tachycardia However, none of these methods had proven practical at the time the book was written. In addition a biphasic defibrillation scheme is described and it is theorized that biphasic defibrillation schemes are more effective by virtue of a larger voltage change when the phase changes or by the biphasic waveform causing hyperpolarization of tissue and reactivation of sodium channels.

An article entitled "Subthreshold conditioning stimuli prolong human ventricular refractoriness", Windle J R, Miles W M, Zipes D P, and Prystowsky E N, American Journal of Cardiology, Vol. 57, No. 6, pp. 381 386, February, 1986, the disclosure of which is incorporated herein by reference, describes a study in which subthreshold stimuli were applied before a premature stimulus and effectively blocked the premature stimulus from having a pro-arrhythmic effect by a mechanism of increasing the refractory period of right ventricular heart tissue.

An article entitled "Ultrarapid subthreshold stimulation for termination of atrioventricular node reentrant tachycardia", Fromer M, and Shenasa M, Journal of the American Collage of Cardiology, Vol. 20, No. 4, pp. 879 883, October, 1992, the disclosure of which is incorporated herein by reference, describes a study in which trains of subthreshold stimuli were applied asynchronously to an area near a reentry circuit and thereby terminated the arrhythmia. Subthreshold stimuli were described as having both an inhibitory and a facilitating effect on conduction. In addition, subthreshold stimuli are described as reducing the threshold of excitability, possibly even causing an action potential.

An article entitled "Inhibition of premature ventricular extrastimuli by subthreshold conditioning stimuli", Skale B, Kallok M J, Prystowsky E N, Gill R M, and Zipes D P, Journal of the American Collage of Cardiology, Vol. 6, No. 1, pp. 133 140, July, 1985, the disclosure of which is incorporated herein by reference, describes an animal study in which a train of 1 msec duration pulses were applied to a ventricle 2 msec before a premature stimuli, inhibited the response to the premature stimuli, with a high frequency train delaying the response for a much longer amount of time (152 msec) than a single pulse (20 msec). The delay between the pacing of the ventricle and the pulse train was 75 msec. However, the subthreshold stimuli only had this effect when delivered to the same site as the premature stimulus. It is suggested to use a subthreshold stimuli in to prevent or terminate tachycardias, however, it is noted that this suggestion is restrained by the spatial limitation of the technique.

An article entitled "The phase of supernormal excitation in relation to the strength of subthreshold stimuli", Yokoyama M, Japanese Heart Journal, Vol. 17, No. 3, pp. 35 325, May, 1976, the disclosure of which is incorporated herein by reference, describes the effect of varying the amplitude of a subthreshold stimuli on supernormal excitation. When the amplitude of the stimuli was increased, the supernormal excitation phase increased in length.

In certain heart diseases, either congenital or acquired, natural pacing is replaced or assisted by artificial pacing induced by a pacemaker, which is generally implanted in the patient's chest. Pacemakers known in the art provide artificial excitatory pulses to the heart tissue to control the heart rhythm. Early pacemakers were asynchronous pulse generators that operated at a fixed invariant rate. Later, demand type pacemakers were developed, in which stimulation pulses are produced only when a naturally-occurring heartbeat is not detected within some maximum type period.

Cardiac pacemakers are required to deliver a stimulus pulse of sufficient magnitude and duration to cause an action potential to propagate from the point of excitation, leading to heart muscle contraction. Thus, the primary function of a pacemaker is to regulate heart rhythm rather than the contractility of the muscle. Furthermore, it is known in the art that the use of a pacemaker generally results in decreased contractility of the cardiac muscle and, consequently, a decreased cardiac output (CO) for a given heart rate.

The hemodynamic effect of different types of pacemakers has long been researched. For example, Wessale et al., in an article entitled "Stroke Volume and Three Phase Cardiac Output Rate Relationship with Ventricular Pacing," *Pacing Clin Electophysiol* 13 (May, 1990), pp. 673-680, describe a three-phase relationship between pacing rate and cardiac output. At a low pacing rate CO increases with increasing rate. There is an intermediate range of rates in which CO stays steady, and above which a further rate increase will cause a decrease in CO. This, of course, causes a major problem for the patient, since a demand for a higher pacing rate typically stems from a demand for an increase in tissue oxygen supply. Research and clinical experience show that with various types of pacemakers, some cardiac output augmentation may take place initially, but is not maintained on a long-term basis and may even deteriorate compared to the situation before beginning pacing. (See, for example, Wirtzfeld et al., "Physiological Pacing: Present Status and Future Developments," *Pacing Clin Electrophysiol* 10 (January, 1987), pp. 41-47.

Talit et al., in "The Effect of External Cardiac Pacing on Stroke Volume," *Pacing Clin Electrophysiol* 13 (May, 1990), pp. 598-602, evaluated the hemodynamic effects of external cardiac pacing on ten subjects and found a decrease of 23% in stroke volume and 14% decrease in cardiac output when compared to the values of these parameters that were obtained prior to pacing.

It is a principle of pacing that the optimal pacing mode is that which gives optimal hemodynamics, thus making the patient the most comfortable. This principle has guided researchers to attempt to regulate the mechanical performance of the heart by synchronization of the contraction of the heart chambers using sequential A/V or multisite pacing. Attempts have also been made to provide pacemakers with improved physiological sensing capabilities, for use in giving feedback to the pacemaker.

FIG. 24A is a schematic diagram illustrating elements of a pacemaker pulse generator 1020 for pacing a heart 1022, as is known in the art. Such pacemakers are described, for example, in *Design of Cardiac Pacemakers*, John G. Webster, ed. (IEEE Press, Piscataway, N.J., 1995), which is incorporated herein by reference. Pacemaker 1020 comprises a battery 1024 or other power source, which charges a tank capacitor 1028 via a charge pump 1026 (or voltage multiplier). To apply a pacing pulse to heart 1022, a switch 1030 is closed, transferring stored charge from capacitor 1028 via a DC-blocking capacitor 1034 to electrodes 1036. Switch 1030 is then opened, and a discharge switch 1032 is preferably closed in order to remove charge buildup on capacitor 1028.

FIG. 24B is a timing diagram illustrating a typical pacing signal 1038 generated by pacemaker 1020 across electrodes 1036. Switch 1030 is closed for a very short period, typically between 0.1 and 1.5 ms, in order to produce a sharp, narrow, cathodic (negative voltage) pacing pulse 1040 with a total discharge of 0.1-50 µC. The amplitude and duration of the pulse are programmable in order to adjust the stimulus that is applied to the heart. Typically, for safety and reliability of pacing, the amplitude of the pulse is set empirically to roughly twice the rheobase, which is the minimum electrical current that will cause the myocardial cell membranes to depolarize. The pacing pulse duration is set to up to twice the chronaxie time, which is the pulse duration that will cause depolarization at twice the rheobase current. A longer duration or higher amplitude has been considered undesirable, because it would tend to discharge battery 1024 prematurely without any improvement in the pacemaker performance or in the physiological performance of the heart or the safety of the pacing. In fact, substantial research and product development efforts in the pacing field have been dedicated to finding pacing methods and waveforms that reduce the amount of energy that must be applied to the heart, in order to prolong battery and circuit lifetime.

After pacing switch 1030 is opened, discharge switch 1032 is closed, typically for about 20 ms, causing an anodic (positive voltage) discharge phase 1042 to appear across electrodes 1036. The specific duration and amplitude of this phase of the pacing waveform are not significant from the point of view of pacing, since it is intended only to remove residual charge and does not provide any stimulation to the heart.

A number of authors have suggested varying the shape and/or duration of the pacing pulse in order to obtain improved pacing effects or to reduce the pulse amplitude or charge flux needed to provide a desired level of stimulation. Among other techniques, biphasic pulses (including both cathodic and anodic portions) or bursts of pulses have been used for defibrillation and antitachycardic pacing.

For example, U.S. Pat. No. 5,531,764 to Adams et al. describes an implantable defibrillator having programmable shock waveforms of different shapes and magnitudes in different combinations and sequences.

Fain et al., in their work "Improved Internal Defibrillation Efficacy with a Biphasic Waveform," in the *American Heart Journal* 117 (February, 1989), pp. 358-64, show that a biphasic truncated exponential shock waveform significantly reduces the initial voltage and energy requirements for effective defibrillation.

Fromer et al., in an article entitled "Ultrarapid Subthreshold Stimulation for Termination of Atrioventricular Node Reentrant Tachycardia," in *Journal of the American College of Cardiology* 20 (October, 1992), pp. 879-83, describe the application of a train of stimuli to intracardiac electrodes in order to terminate tachycardic episodes without the need for cardioversion. The train ranged from 4 to 16 pulses, each 2 ms long. The pulse train was thus meant, under certain circumstances, to take the place of or precede more drastic defibrillative measures, and not to pace the heart.

Similarly, Hedberg, et al., in U.S. Pat. No. 5,622,687, describe an implantable defibrillator which applies a train of low-energy defibrillation pulses in order to defibrillate the heart with a lower total energy flux than would ordinarily be required using conventional defibrillation pulses. The train includes between 2 and 10 pulses, preferably about 10 ms apart. The width of the pulses is not specified. The pulses may be either monophasic or biphasic. In any case, the clinical and technical considerations in generating signals of the type employed by a defibrillator are entirely different from those involved in pacing the heart.

Kinsley, et al., in an article entitled "Prolongation and Shortening of Action Potentials by Electrical Shocks in Frog Ventricular Muscle," in the *American Journal of Physiology* 6 (*Heart Circ. Physiol.* 35, 1994), pp. H2348-H2358, describe measurements of contraction length and intracellular action potential following application of shocks to heart tissue. By varying the strength of the shocks, the contraction strength of the tissue could be increased, and the action potentials lengthened or shortened. The authors propose that such techniques could be used in defibrillation, but make no suggestion with regard to pacing the heart.

U.S. Pat. No. 4,312,354, to Walters, describes a pacemaker with a circuit for pulse width modulation of the stimulus pulses applied to the heart. The purpose of the modulation is not to directly affect the pacing itself, but rather to afford a means for indicating to an external telemetry unit a control state of the pacemaker.

Thakor, et al., in an article entitled "Effect of Varying Pacing Waveform Shapes on Propagation and Hemodynamics in the Rabbit Heart," in *The American Journal of Cardiology* 79 (Mar. 20, 1997), pp. 36-43, describe experiments using biphasic pacing pulses to increase the speed of electrical conduction in heart muscle fibers. Both monophasic and biphasic pulses of 2 to 8 ms total duration were applied to isolated muscle fibers using unipolar electrodes. The biphasic pulses consisted of a single cathodic pulse immediately followed by a single anodic pulse, or vice versa. The article reports that propagation of the resulting electrical potentials along the fibers was significantly faster for the biphasic stimulation. It was observed that pacing with an anodic/cathodic biphasic pulse resulted in faster electrical conduction, and led to an earlier development of pressure in the muscle fiber and a shorter duration of the pressure waveform than did monophasic pulses. The authors suggest that the biphasic pulse could be associated with the ability to augment muscular contraction.

PCT patent application PCT/IL97/00012, published as WO 97/25098, to Ben-Haim et al., which is incorporated herein by reference, describes methods for modifying the force of contraction of at least a portion of a heart chamber by applying a non-excitatory electric field to the heart at a delay after electrical activation of the portion. The non-excitatory field is such as does not induce activation potentials in cardiac muscle cells, but rather modifies the cells' response to the activation. The non-excitatory field may be applied in combination with a pacemaker or defibrillator, which applies an excitatory signal (i.e., pacing or defibrillation pulses) to the heart muscle.

The following references, which are incorporated herein by reference, may be of interest:

U.S. Pat. No. 3,572,345 to Auphan
U.S. Pat. No. 3,587,567 to Schiff
U.S. Pat. No. 3,651,805 Breiling
U.S. Pat. No. 3,942,536 to Mirowski et al.
U.S. Pat. No. 3,952,750 to Mirowski et al.
U.S. Pat. No. 4,030,509 to Heilman et al.
U.S. Pat. No. 4,106,494 to McEachern
U.S. Pat. No. 4,164,216 to Person
U.S. Pat. No. 4,184,493 to Langer et al.
U.S. Pat. No. 4,202,340 to Langer et al.
U.S. Pat. No. 4,223,678 to Langer et al.
U.S. Pat. No. 4,237,895 to Johnson
U.S. Pat. No. 4,273,114 to Barkalow et al.
U.S. Pat. No. 4,312,354 to Walters
U.S. Pat. No. 4,316,472 to Mirowski et al.
U.S. Pat. No. 4,384,585 to Zipes
U.S. Pat. No. 4,387,717 to Brownlee et al.
U.S. Pat. No. 4,403,614 to Engle et al.
U.S. Pat. No. 4,407,288 to Langer et al.
U.S. Pat. No. 4,440,172 to Langer
U.S. Pat. No. 4,506,680 to Stokes
U.S. Pat. No. 4,543,956 to Herscovici
U.S. Pat. No. 4,554,922 to Prystowsky et al.
U.S. Pat. No. 4,559,946 to Mower
U.S. Pat. No. 4,559,947 to Renger et al.
U.S. Pat. No. 4,566,456 to Koning et al.
U.S. Pat. No. 4,572,191 to Mirowski et al.
U.S. Pat. No. 4,628,934 to Pohndorf et al.
U.S. Pat. No. 4,651,716 to Forester et al.
U.S. Pat. No. 4,674,508 to DeCote
U.S. Pat. No. 4,679,572 to Baker, Jr.
U.S. Pat. No. 4,690,155 to Hess
U.S. Pat. No. 4,726,279 to Kepler et al.
U.S. Pat. No. 4,726,379 to Altman et al.
U.S. Pat. No. 4,765,341 to Mower et al.
U.S. Pat. No. 4,830,006 to Haluska et al.
U.S. Pat. No. 4,928,688 to Mower
U.S. Pat. No. 4,971,058 to Pless et al.
U.S. Pat. No. 4,979,507 to Heinz et al.
U.S. Pat. No. 4,998,531 to Bocchi et al.
U.S. Pat. No. 5,003,976 to Alt
U.S. Pat. No. 5,020,544 to Dahl et al.
U.S. Pat. No. 5,022,396 to Watanabe
U.S. Pat. No. 5,044,375 to Bach, Jr. et al.
U.S. Pat. No. 5,083,564 to Scherlag
U.S. Pat. No. 5,087,243 to Avitall
U.S. Pat. No. 5,097,832 to Buchanan
U.S. Pat. No. 5,111,815 to Mower
U.S. Pat. No. 5,129,394 to Mehra
U.S. Pat. No. 5,137,021 to Wayne et al.
U.S. Pat. No. 5,154,501 to Svenson et al.
U.S. Pat. No. 5,156,147 to Warren et al.
U.S. Pat. No. 5,156,149 to Hudrlik
U.S. Pat. No. 5,161,527 to Nappholz et al.
U.S. Pat. No. 5,163,428 to Pless
U.S. Pat. No. 5,172,699 to Svenson et al.
U.S. Pat. No. 5,184,620 to Cudahy et al.
U.S. Pat. No. 5,199,428 to Obel et al.
U.S. Pat. No. 5,205,284 to Freeman
U.S. Pat. No. 5,213,098 to Bennett et al.
U.S. Pat. No. 5,236,413 to Feiring
U.S. Pat. No. 5,281,219 to Kallok
U.S. Pat. No. 5,282,785 to Shapland et al.
U.S. Pat. No. 5,284,491 to Sutton et al.
U.S. Pat. No. 5,286,254 to Shapland et al.
U.S. Pat. No. 5,305,745 to Zacouto
U.S. Pat. No. 5,320,642 to Sherlag
U.S. Pat. No. 5,320,643 to Roline et al.
U.S. Pat. No. 5,327,887 to Nowakowski
U.S. Pat. No. 5,346,506 to Mower et al.
U.S. Pat. No. 5,353,800 to Pohndorf et al.
U.S. Pat. No. 5,366,486 to Zipes et al.
U.S. Pat. No. 5,368,040 to Carney
U.S. Pat. No. 5,370,665 to Hudrlik
U.S. Pat. No. 5,386,837 to Sterzer
U.S. Pat. No. 5,387,419 to Levy et al.
U.S. Pat. No. 5,391,192 to Lu et al.
U.S. Pat. No. 5,391,199 to Ben-Haim
U.S. Pat. No. 5,398,683 to Edwards et al.
U.S. Pat. No. 5,415,629 to Henley
U.S. Pat. No. 5,417,717 to Salo et al.
U.S. Pat. No. 5,419,763 to Hildebrand
U.S. Pat. No. 5,425,363 to Wang
U.S. Pat. No. 5,443,485 to Housworth et al.
U.S. Pat. No. 5,443,489 to Ben-Haim
U.S. Pat. No. 5,447,520 to Spano et al.
U.S. Pat. No. 5,458,568 to Racchini et al.
U.S. Pat. No. 5,464,020 to Lemer
U.S. Pat. No. 5,468,254 to Hahn et al.
U.S. Pat. No. 5,472,453 to Alt
U.S. Pat. No. 5,476,484 to Hedberg
U.S. Pat. No. 5,476,485 to Weinberg et al.
U.S. Pat. No. 5,476,497 to Mower et al.
U.S. Pat. No. 5,482,052 to Lerner
U.S. Pat. No. 5,499,971 to Shapland et al.
U.S. Pat. No. 5,501,662 to Hofmann
U.S. Pat. No. 5,514,162 to Bomzin et al.
U.S. Pat. No. 5,520,642 to Bigagli et al.
U.S. Pat. No. 5,531,764 to Adams et al.
U.S. Pat. No. 5,540,722 to Clare et al.
U.S. Pat. No. 5,549,646 to Kayz et al.
U.S. Pat. No. 5,556,421 to Prutchi et al.
U.S. Pat. No. 5,568,809 to Ben-Haim
U.S. Pat. No. 5,571,143 to Hoegnelid et al.
U.S. Pat. No. 5,584,803 to Stevens et al.
U.S. Pat. No. 5,584,868 to Salo et al.
U.S. Pat. No. 5,587,200 to Lorenz et al.
U.S. Pat. No. 5,601,609 to Duncan
U.S. Pat. No. 5,601,611 to Fayram et al.
U.S. Pat. No. 5,626,622 to Cooper
U.S. Pat. No. 5,634,899 to Shapland et al.
U.S. Pat. No. 5,649,966 to Noren et al.
U.S. Pat. No. 5,651,378 to Matheny et al.
U.S. Pat. No. 5,662,687 to Hedberg et al.
U.S. Pat. No. 5,674,251 to Combs et al.
U.S. Pat. No. 5,674,259 to Gray
U.S. Pat. No. 5,683,431 to Wang
U.S. Pat. No. 5,687,734 to Dempsey et al.
U.S. Pat. No. 5,713,935 to Prutchi et al.
U.S. Pat. No. 5,720,768 to Verboven-Nelissen
U.S. Pat. No. 5,735,876 to Kroll et al.
U.S. Pat. No. 5,738,096 to Ben Haim
U.S. Pat. No. 5,738,105 to Kroll
U.S. Pat. No. 5,749,906 to Kieval et al.

U.S. Pat. No. 5,755,740 to Nappholtz
U.S. Pat. No. 5,782,876 to Flammang
U.S. Pat. No. 5,782,881 to Lu et al.
U.S. Pat. No. 5,792,198 to Nappholz
U.S. Pat. No. 5,792,208 to Gray
U.S. Pat. No. 5,797,967 to KenKnight
U.S. Pat. No. 5,800,464 to Kieval
U.S. Pat. No. 5,807,234 to Bui et al.
U.S. Pat. No. 5,814,079 to Kieval
U.S. Pat. No. 5,865,787 to Shapland et al.
U.S. Pat. No. 5,871,506 to Mower
U.S. Pat. No. 5,906,607 to Taylor et al.
U.S. Pat. No. 5,913,876 to Taylor et al.
U.S. Pat. No. 5,927,284 to Borst et al.
U.S. Pat. No. 6,006,134 to Hill et al.
U.S. Pat. No. 6,032,074 to Collins
U.S. Pat. No. 6,032,672 to Taylor
U.S. Pat. No. 6,041,252 to Walker et al.
U.S. Pat. No. 6,067,470 to Mower
U.S. Pat. No. 6,071,305 to Brown et al.
U.S. Pat. No. 6,086,582 to Altman et al.
U.S. Pat. No. 6,136,019 to Mower
U.S. Pat. No. 6,141,586 to Mower
U.S. Pat. No. 6,151,586 to Brown
U.S. Pat. No. 6,178,351 to Mower
U.S. Pat. No. 6,295,470 to Mower
U.S. Pat. No. 6,317,631 to Ben-Haim et al.
U.S. Pat. No. 6,337,995 to Mower
U.S. Pat. No. 6,341,235 to Mower
U.S. Pat. No. 6,343,232 to Mower
U.S. Pat. No. 6,411,847 to Mower
U.S. Reissue Pat. RE38119 to Mower
EP 0 148 687 February, 1988
EP 0 314 078 October, 1993
EP 0 727 241 August, 1996
JP 04-117967 April, 1992
JP 4-365493 December, 1992
JP 7-126600 May, 1995
JP 8-243176 September, 1996
PCT Publication WO 92/00716 January, 1992
PCT Publication WO 95/08316 March, 1993
PCT Publication WO 97/25101 July, 1997
PCT Publication WO 98/10831 March, 1998
PCT Publication WO 91/19534 December, 1999
PCT Publication WO 00/04947 February, 2000
Antman, E. M. et al. "Treatment of 150 Cases of Life-Threatening Digitalis Intoxication with Digoxin-Specific Fab Antibody Fragments;" June 1990 Circulation; vol. 81: No. 6: pp. 1744-1752.
Antoni, H. et al. "Polarization Effects of Sinusoidal 50-Cycle Alternating Current on Membrane Potential of Mammalian Cardiac Fibers", Pfluegers Arch. 314, pp. 274-291 (1970).
Bach, S. M., Tach Arrhythmia Detection, Implantable Cardioverter Defibrilator Therapy The Engineering-Clinical Interface, Chapter 15, pp. 303-323, Eds, Mark W. Kroll and Michael H. Lehmann, Kluwer Academic Publishers, USA, 1997.
Bakker, P. F., et al., "Beneficial Effects of Biventricular Pacing of Congestive Heart Failure", PACE, vol. 17, April 1994, Part 11, one page. cited by other.
Bakker, P. F., et al., "Biventricular Pacing Improves Functional Capacity in Patients with End-Stage Congestive Heart Failure" PACE, vol. 17, April 1995, Part 11, one page.
Bargheer K. et al., "Prolongation of Monophasic Action Potential Duration and the Refractory Period in the Human Heart by Tedisamil, a New Potassium-Blocking Agent", J. Eur Heart 15 (10), October 1994, pp. 1409-1414. cited by other.
Borst, et al. "Coronary Artery Bypass Grafting Without Cardiopulomonary Bypass and Without Interruption of Native Coronary Flow Using a Novel Anastomosis site restraining device ("Octupus")", Journal of the American College of Cardiology, 27 (6), May 1996. cited by other.
Cano, N. J. et al. "Dose-Dependent Reversal of Digoxin-Inhibited Activity of an In-Vitro NA+K+ATPase Model by Digoxin-Specific Antibody;" May 1996; pp. 107-1011; Toxicology Letters; vol. 85; No. 2.
Cazeau S. et al., "Multisite Pacing for End-Stage Heart Failure: Early Experience", Pacing and Clinical Electrophysiology vol. 19, November 1996, Part 11, pp. 1748-1757.
Cooper, W., "Postextrasystolic Potentiation: Do We Really Know What It Means and How To Use It?" Circulation, vol. 88, No. 6, December 1993, pp. 2962-2971.
Dillon, S M., abstract of "Synchronized Repolarization After Defibrillation Shocks. A Possible Component of the Defibrillation Process Demonstration By Optical Recordings in Rabbit Heart", Circulation, May 1992, vol. 85, No. 5, pp. 1865-1878.
Fain, E. S., et al. "Improved Internal Defibrillation Efficacy with a Biphasic Waveform", American Heart Journal 117 (2), February 1989, pp. 358-364.
Fleg, J. L. et al., "Impact of Age on the Cardiovasvular Response to Dynamic Upright Exercise in Healthy Men and Women", J. Appl. Physiol., vol. 78, 1995, p. 890.
Foster, A. H, et al., "Acute Hemodynamic Effects of Atrio-Biventricular Pacing in Humans", 1995, The Society of Thoracic Surgeons vol. 59, pp. 294-299.
Franz, M. R., "Bridging the Gap Between Basic and Clinical Electrophysiology: What Can be Learned from Monophasic Action Potential Recordings?", J. Cardiovasc Electrophysiol 5(8), August 1994, pp. 699-710.
Franz, M. R., "Method and Theory of Monophasic Action Potential Recording", Prog. Cardiovasc Dis 33 (6), May-June 1991, pp. 347-368.
Franz, M. R., "Progress in Cardiovascular Disease: Monophasic Action Potential Symposium, I. Introduction", Prog. Cardiovasc Dis 33 (6), May-June 1991 pp. 345-346.
Fu. P and B. J. Bardakjian, "System Identification of Electrically Coupled Smooth Muscle Cells: The Passive Electrically Coupled Smooth Muscle Cells: The Passive Electrical Properties", published in IEEE Transactions on Biomedical Engineering, 38(11), pp. 1130-1140, 1991.
Ham, Frederic M and Han, Soowhan, "Classification of Cardiac Arrhythmias Using Fuzzy Artmap"; IEEE Transactions on Biomedical Engineering, vol. 43, No. 4, April 1996.
Hoffman, B. F. et al., "Effects of Postextrasytolic Potentiation on Normal & Failing Hearts", Bulletin of New York Academy of Medicine, 41 in 1965, pp. 498-534.
Josephson, M. E., Clinical Cardiac Electrophysiology: Techniques and Interpretations, 2nd. Edition, Lea & Febiger, Philadelphia, 1991.
King, A. et al., The Inotropic Action of Paired Pulse Stimulation in the Normal and Failing Heart: An Experimental Study, Cardiovascular Research, vol. 2, April 1968, pp. 122-129.
Knisley et al., "Prolgongation and Shortening of Action Potentials by Electrical Shocks in Frog Ventricular Muscle", American Journal of Physiology 6 (Heart Circ. Physiol. 35, 1994) pp. H2348-H2358.

Koller, et al., "Relation Between Repolarization and Refractoriness During Programmed Electrical Stimulation in the Human Right Ventricle", Circulation 91(9), 2378-2384, 1995.

Langberg, Jonathan J. et al., "Identification of Ventricular Tachycardia with Use of the Morphology of the Endocardial Electrogram", Circulation, vol. 77, No. 6, June 1988. cited by other.

McVeigh, E. R et al., "Noninvasive Measurement of Transmural Gradients in Myocardial Strain with MR Imaging", Radiology 180 (3), September 1991, pp. 677, 679-684. cited by other.

Mercando, A. D., et al., "Automated Detection of Tachardias by Antitachicardia Devices", Chapter 100, pp. 943-948, in Cardiac Electrophysiology from Cell to Bedside, Eds. Douglas P. Zipes and Jose Jalife, publishers W.B. Saunders Company (1990).

Moran, R. J. et al; "Digoxin-Specific Fab Fragments Impair Renal Function in the Rat:" 1994; pp. 854-856; Journal of Pharmacy and Pharmacology; vol. 46: No. 10.

Morse, et al., "A Guide to Cardiac Pacemakers, Defibrillators and Related Products", Droege Computing Services, Durham, N.C.

Merck Manual, The, Section 3, the 16th Edition of the Merck Manual, Published in 1992.

Paul, V E., et al. "Automatic Recognition of Ventricular Arrythmias Using Temporal Electrogram Anaylsis" Pace, vol. 14, pp. 1265-1273, (1991).

Qiuzhen Xue et al., "Neural-Network-Based Adaptive Matched Filtering for QRS Detection", IEEE Transactions on Biomedical Engineering, vol. 39, No. 4. April 1992.

Saksena et al., "Dual-site Atrial Pacing in Atrial Fibrillation", JACC, vol. 28, No. 3, September 1996, pp. 687-694.

Shumaik, G. M. et al, "Oleander Poisoning; Treatment with Digoxin-Specific Fab Antibody Fragments;" July 1988; pp. 732-735; Annals of Emergency Medicine; vol. 17; No. 7.

Sweeny R J, et al., abstract of "Countershock Strength-Duration Relationship for Myocardial Refractory Period Extension", Acad Emerg. Med., January 1995, vol. 2, No. 1, pp. 57-62.

Sweeny R J, et al., abstract of "Refractory Interval After Transcardiac Shocks During Ventricular Fibrillation", Circulation, December 1996, vol. 94, No. 11, pp. 2947-2952.

Sweeny R J, et al., abstract of "Ventricular Refractory Period Extension Caused by Defibrillation Shocks", Circulation, September 1990, vol. 82, No. 3, pp. 965-972.

Talit, U. et al., "The Effect of External Cardiac Pacing on Stroke Volume", Pace 13, May 1990, pp. 598-560.

Tsong, T. Y., "Electroportion of Cell Membranes" August 1991; pp. 297-306; Biophysical Journal; vol. 60.

Verrier, et al, "Electrophysiologic Basis for T Wave Alternans as an Indeox of Vulnerability to Ventricular Fibrillation" Journal of Cardiovascular Electrophysiology, vol. 5, pp. 445-461, 1994.

Webster, John G., ed., Design of Cardiac Pacemakers, IEEE Press, Piscataway, N.J., 1995.

Wessale, J. L. et al., "Stroke Volume and Three Phase Cardiac Output Rate Relationship with Ventricular Pacing" Pace 13, May 1990, pp. 673-680.

Wirtzfeld, A. et al., "Physiological Pacing: Present Status and Future Developments", Pace 10 January-February 1987, Part I, pp. 41-57.

Zipes, D et al., Cardiac Electrophysiology from Cell to Bedside, 1990, W.B. Saunders Co., Philadelphia.

Guidant Product Catalogue, 2001, 2 pages.

"The Latest Tetralogy of Fallot Discussion with Graphical Support Including Video of Echocardiography and Catherization" Pediatric Electrophysiologypicu Book ("An On-Line Resource for Pediatric Critical Care").

Brumwell D. A. et al. "The Amplifier: Sensing the Depolarization", Implantable Cardioverter Defibrillator Therapy: The Engineering-Clinical Interface, Chap. 14, pp. 275-302, Eds. Kroll and Lehmann, Kluwer Academic Publishers, USA 1997.

Gill R J, et al., abstract of "Refractory Period Extension During Ventricular Pacing at Fibrillatory Pacing Rates" Pacing Clin. Electrophysiol, March 1997, vol. 20, No. 3, pp. 647-653.

Hardage, M. L. and Sweeney, M. B., "Anti-Tachycardia Pacing and Cardioversion", Implantable Cardiovertre Defibrilator Therapy: The Engineering-Clinical Interface, Chapt. 6, pp. 325-342, Eds. Mark W. Kroll and Michael H. Lehmann, Kluwer Academic Publishers U.S.A 1997.

Matheny R. G. and C. J. Shaar, "Vagus Nerve Stimulation as a Method to Temporarily Slow or Arrest the Heart" Annals of Thoracic Surgery. 63 (6) Supplement, pp. S28-29, June 1997.

Supino, C. G., "The System", Implantable Cardioverter Defibrillator Therapy: The Engineering-Clinal Interface, Chapt. 8, pp. 163-172, Eds. Mark W. Kroll and Michael H. Lehmann, Kluwer Academic Publishers, USA 1997.

Thakor et al., "Effect of Varying Pacing Waveform Shapes on Propagation and Hemodynamics in the Rabbit Heart", The American Journal of Cardiology 79 (6A), pp. 36-43. 1997.

R, Ranjan & N. V. Thakor (1995) Annals of Biomedical Engineering 23: pp. 812-821 "Electrical Stimulation Of Cardiac Myocytes".

N. Nannini & K. Horch (1991) IEEE Transactions on Biomedical Engineering 38: pp. 769-776: "Muscle Recruitment With Intrafascicular Electrodes".

D. M. Bers (1991) "Excitation Contraction Coupling And Cardiac Contractile Force"; Chapter 2, p. 17, Kluwer Academic.

S. B. Knisley et al. (19912) Circulation Research 70: pp. 707-715 "Effect Of Field Stimulation On Cellular Repolarization In Rabbit Myocardium".

S. M. Dillion (1991) Circulation Research 69: pp. 842-856; "Optial Recordings In The Rabbit Heart Show That Defibrillation Strength Shocks Prolong The Duration Of . . . ".

J. Fleischhauer et al. (1995) Circulation 92: pp. 587-594; "Electrical Resistances Of Interstitial And Microvascular Space As Determinants Of The Extracellular Electrical . . . ".

A. Taniguchi et al.; Am. J. Physiol. p. 267: H694-H705; "Inhomogeneity Of Cellular Activation Time And Vmax In Normal Myocardial Tissue Under Electrical Field . . . ".

R. Lubart et al. (1992) J. Photochemical Photobiology B 14; pp. 337-341 "Effect Of Light On Calcium Transport In Bull Sperm Cells".

V. A. Loginov (1992) Aviakosm Ekolog Med 26: pp. 49-51; "Accumulation Of Calcium Ions In Myocardial Sacoplasmic Reticulum Of Restrained Rats Exposed To The . . . ".

J. L. Schwartz et al. (1990) Bioelectromagnetics 11: pp. 349-358; "Exposure Of Frog Hearts To CW Or Amplitude-Modified VHF Fields: Selective Efflux Of Calcium Ions . . . ".

E. Lindstrom et al. 1995) Bioelectromagnetics 16: pp. 41-47: "intracellular Calcium Oscillations In A T-Cell Line After Exposure To Extremely-Low-Frequency Magnetic . . . ".

V. A. Loginov et al. (1991) Kosm Biol Aviakosm Med 15; pp. 51-53; "Effects Of An Impulse Electromagnetic Field On Calcium Ion Accumulation In The Sarcoplasmic . . . ".

L. A. Coulton & A. T. Barker (1993) Phys. Med. Biol. 38; pp. 347-360; "Magnetic Fields And Intracellular Calcium; Effects On Lymphocytes Exposed To Conditions For . . . ".

A. Pumir et al. (1994) Proc. R. Soc. Lond. B. Biol. Sci. 257; pp. 129-134; "Control of Rotating Waves In Cardiac Muscle: Analysis Of The Effect Of Electric Fields".

M. Sblomonow et al. (1983) Am. J. Physical Medicine 62: pp. 71-82; "Control Of Muscle Contractile Force Through Indirect High-Frequency Stimulation".

J. D. Bronzino (1995) "Biomedical Engineering Handbook", Chapter 82.5; p. 1288, "IEEE press/CRC press".

J. R. Windle et al. (1986) Am. J. Cardiol. 57: pp. 381-386; "Subthreshold Conditioning Stimuli Prolong Human Ventricular Refractoriness".

M. Fromer & M. Shenasa (1992) J. Am. Coll. Cardio. 20; pp. 879-883; "Ultrarapid Subthreshold Stimulation For Termination Of Atriventricular Node Reentrant Tachycardia".

B. Skale et al. (1985) J. Am. Coll. Cardiol. 6: pp. 133-140; "Inhibition Of Premature Ventricular Extrastimuli By Subthreshold Conditioning Stimuli".

M. Yokoyama (1976) Japanese HEart Journal 17; pp. 315-325; "The Phase Of Supernormal Excitation In Relation To The Strength Of Subthreshold Stimuli".

Cheng et al (1993) Science 262; Oct. 29; "Calcium Sparks: Elementary Events Underlying Excitation-Contraction Coupling In Heart Muscle".

Stevenson et al.; Am J. Cardiol. 57; (6) "Electrophysiological Characteristics Of Ventricular Tachycardia Or Fibrillation In Relation To Age Of Myocardial Infarction". cited by other.

SUMMARY OF THE INVENTION

Some signals described herein are "multi-functional signals," meaning that they have at least two separate functions. For example, an extended pacing signal as described herein is a multi-functional signal, in that it both paces the heart and modulates (e.g., enhances) contractility. Similarly, a signal that includes an excitatory portion followed (after a delay as low as zero, or longer, as described herein) by a non-excitatory portion, is a multi-functional signal.

It is an object of some aspects of the present invention to provide a method for locally controlling the electrical and/or mechanical activity of cardiac muscle cells, in situ. Preferably, continuous control is applied. Alternatively, discrete control is applied. Further preferably, the control may be varied between cardiac cycles. One example of electrical control is shortening the refractory period of a muscle fiber by applying a negative voltage to the outside of the cell. The cell may also be totally blocked from reacting by maintaining a sufficiently positive voltage to the outside of the cell, so that an activation signal fails to sufficiently depolarize the cellular membrane. One example of mechanical control includes increasing or decreasing the strength of contraction and the duration of the contraction. This may be achieved by extending or shortening the plateau and/or the action potential duration by applying non-excitatory voltage potentials across the cell. The increase in strength of contraction may include an increase in peak force of contraction attained by muscle fibers, may be an increase in an average force of contraction, by synchronization of contraction of individual fibers or may include changing the timing of the peak strength.

It should be appreciated that some aspects of the present invention are different from both pacemaker operation and defibrillator operation. A pacemaker exerts excitatory electric fields for many cycles, while a defibrillator does not repeat its applied electric field for many cycles, due to the disruptive effect of the defibrillation current on cardiac contraction. In fact, the main effect of the defibrillation current is to reset the synchronization of the heart by forcing a significant percentage of the cardiac tissue into a refractory state. Also, defibrillation currents are several orders of magnitude stronger than pacing currents. It is a particular aspect of some embodiments of the present invention that the regular activation of the heart is not disrupted, rather, the activation of the heart is controlled, over a substantial number of cycles, by varying parameters of the reactivity of segments of cardiac muscle cells.

In some aspects of the invention, where the heart is artificially paced in addition to being controlled in accordance with the present invention, the activation cycle of the heart is normal with respect to the pacing. For example, when the control is applied locally, such that the activation of the rest of the heart is not affected.

In some aspect of the invention, the control is initiated as a response to an unusual cardiac event, such as the onset of fibrillation or the onset of various types of arrhythmias. However, in other aspects of the present invention, the control is initiated in response to a desired increase in cardiac output or other long-term effects, such as reducing the probability of ventricular fibrillation (VF) or increasing the coronary blood flow.

Another difference between defibrillation, pacing and some embodiments of the present invention is that defibrillation and pacing are applied as techniques to affect the entire heart (or at least an entire chamber), while certain embodiments of the present invention, for example, fences (described below), are applied to local portion of the heart (which may be as large as an entire chamber) with the aim of affecting only local activity. Yet another difference between some embodiment of the present invention and defibrillation is in the energy applied to the heart muscle. In defibrillation, a typical electric field strength is 0.5 Joule (which is believed to be strong enough to excite refractory tissue, "Optical Recordings . . . ", cited above), while in various embodiment of the invention, the applied field strength is between 50 and 500 micro joules, a field strength which is believed to not cause action potentials in refractory tissue.

It is a further object of some aspects of the present invention to provide a complete control system for the heart which includes, inter alia, controlling the pacing rate, refractory period, conduction velocity and mechanical force of the heart. Except for heart rate, each of these parameters may be locally controlled, i.e., each parameter will be controlled in only a segment of cardiac muscle. It should be noted that heart rate may also be locally controlled, especially with the use of fences which isolate various heart segments from one another, however, in most cases this is detrimental to the heart's pumping efficiency.

In one preferred embodiment of the present invention, electrical and/or mechanical activity of a segment of cardiac muscle is controlled by applying a non-exciting field (voltage) or current across the segment. A non-exciting signal may cause an existing action potential to change, but it will not cause a propagating action potential, such as those induced by pacemakers. The changes in the action potential may include extension of the plateau duration, extension of the refractory period, shortening of the post-plateau repolarization and other changes in the morphology of the action potential. However, the non-exciting signal may affect a later action potential, for example, it may delay such a potential or may accelerate its onset. Another type of non-exciting signal is a voltage which does not cause a new contraction of the cardiac muscle cell to which the non-exciting signal is applied. Activation potential generation may be averted either by applying voltage of the wrong polarity; the voltage being applied when the cell and/or the surrounding cells are not sensitive to it or by the amplitude of the voltage being too small to depolarize the cell to the extent that a new action potential will be generated during that period.

Optionally, this control is exerted in combination with a pacemaker which applies an exciting signal to the heart. In a preferred embodiment of the invention, a pacemaker (or a defibrillator) incorporates a controller, operating in accordance with at least one embodiment of the invention. A pacemaker and a controller may share a battery, a micro-controller, sensors and possibly electrodes.

In another preferred embodiment of the present invention, arrhythmias and fibrillation are treated using fences. Fences are segments of cardiac muscle which are temporarily inactivated using electrical fields. In one example, atrial fibrillation is treated by channeling the activation signal from an SA node to an AV node by fencing it in. In another example, fibrillations are damped by fencing in the multitude of incorrect activation signals, so that only one path of activation is conducting. In still another example, ventricular tachycardia or fibrillation is treated by dividing the heart into insulated segments, using electrical fields and deactivating the fences in sequence with a normal activation sequence of the heart, so that at most only one segment of the heart will be prematurely activated.

In still another preferred embodiment of the invention, the muscle mass of the heart is redistributed using electrical fields. In general, changing the workload on a segment of cardiac muscle activates adaptation mechanisms which tend to change the muscle mass of the segment with time. Changing the workload may be achieved, in accordance with a preferred embodiment of the invention, by increasing or decreasing the action potential plateau duration of the segment, using applied electrical fields. Alternatively or additionally, the workload may be changed indirectly, in accordance with a preferred embodiment of the invention, by changing the activation time of the segment of the heart and/or its activation sequence. Further additionally of alternatively, the workload may be changed by directly controlling the contractility of a segment of the heart.

In yet another preferred embodiment of the invention, the operation of the cardiac pump is optimized by changing the activation sequence of the heart and/or by changing plateau duration at segments of the heart and/or by changing the contractility thereat.

In still another preferred embodiment of the invention, the cardiac output is modified, preferably increased, by applying a non-excitatory electric field to a segment of the heart, preferably the left ventricle. Preferably, the extent of increase in cardiac output, especially the left ventricular output, is controlled by varying the size of the segment of the heart to which such a field is applied. Alternatively or additionally, the strength of the electric field is changed. Alternatively or additionally, the timing of the pulse is changed. Alternatively or additionally, the duration, shape or frequency of the pulse is changed. The increase in output may include an increase in peak flow rate, in flow volume, in average flow rate, or it may include a change in the flow profile, such as a shift in the development of the peak flow, which improves overall availability of blood to body organs.

In still another preferred embodiment of the invention, the developed ventricular pressure is modified, preferably increased, by applying a non-excitatory electric field to a segment of the heart, preferably the left ventricle. Preferably, the extent of increase in cardiac output is controlled by varying the size of the segment of the heart to which such a field is applied. Alternatively or additionally, the strength of the electric field is changed. Alternatively or additionally, the timing of the pulse is changed. Alternatively or additionally, the duration of the pulse is changed. Alternatively or additionally, the waveform of the pulse is changed. Alternatively or additionally, the frequency of the pulse is changed. The increase in pressure may include an increase in peak pressure, average pressure or it may include a change in the pressure profile, such as a shift in the development of the peak pressure, which improves the contractility.

In accordance with yet another preferred embodiment of the invention, the afterload of the heart is increased by applying non-excitatory electric fields to at least a segment of the heart, whereby the flow in the coronary arteries is improved.

In accordance with another preferred embodiment of the invention various cardiac parameters are controlled via inherent cardiac feedback mechanisms. In one example, the heart rate is controlled by applying a non-exciting voltage to pacemaker cells of the heart, at or near the SA node of the heart. Preferably, the heart rate is increased by applying the non-excitatory field.

In a preferred embodiment of the invention, a single field is applied to a large segment of the heart. Preferably, the field is applied at a time delay after the beginning of the systole. Preferably, the non-exciting field is stopped before half of the systole is over, to reduce the chances of fibrillation.

In another preferred embodiment of the invention, a plurality of segments of the heart are controlled, each with a different non-excitatory electric field. Preferably, each electric field is synchronized to the local activation or other local parameters, such as initiation of contraction. A further preferred embodiment of the invention takes into account the structure of the heart. The heart muscle is usually disposed in layers, with each layer having a (different) muscle fiber orientation. In this embodiment of the invention, a different field orientation and/or polarity is preferably applied for different orientations of muscle fibers.

In one preferred embodiment of the invention, this technique, which takes the muscle fiber orientation into account, may be applied to local defibrillation-causing electric fields the purpose of which fields may be to delay the repolarization of a certain, limited segment of the heart, thereby creating a fence.

There is therefore provided in accordance with a preferred embodiment of the invention, a method of modifying the force of contraction of at least a portion of a heart chamber, comprising:

providing a subject having a heart, comprising at least a portion having an activation; and applying a non-excitatory electric field having a given duration, at a delay after the activation, to the portion, which causes the force of contraction to be increased by at least 5%.

Preferably, the force is increased by a greater percentage such as at least 10%, 30% or 50%

There is further provided, in accordance with a preferred embodiment of the invention a method of modifying a force of contraction of at least a portion of a heart chamber, comprising:

providing a subject having a heart, comprising at least a portion having an activation; and applying a non-excitatory electric field having a given duration, to the portion at a delay of less than 70 msec after the activation.

There is further provided, in accordance with a preferred embodiment of the invention a method of modifying the force of contraction of at least a portion of a heart chamber, comprising:

providing a subject having a heart, comprising at least a portion having an activation; and applying a non-excitatory electric field having a given duration, at a delay after the activation, to the portion, which causes the pressure in the chamber to be increased by at least 2%.

Preferably the pressure is increased by a greater amount such as at least 10% or 20%.

There is further provided, in accordance with a preferred embodiment of the invention a method of modifying the force of contraction of at least a portion of a heart chamber, comprising:

providing a subject having a heart, comprising at least a portion having an activation; and applying a non-excitatory electric field having a given duration, at a delay after the activation, to the portion, wherein the chamber has a flow volume and wherein the flow volume is increased by at least 5%.

Preferably, the flow volume is increased by a greater amount such as at least 10% or 20%.

There is further provided, in accordance with a preferred embodiment of the invention a method of modifying the force of contraction of at least a portion of a heart chamber comprising:

providing a subject having a heart, comprising at least a portion having an activation; and applying a non-excitatory electric field having a given duration, at a delay after the activation, to the portion, wherein the chamber has a flow rate such that the flow rate is increased by at least 5%.

Preferably, the flow rate is increased by a greater amount such as at least 10% or 20%.

There is further provided, in accordance with a preferred embodiment of the invention a method of modifying the force of contraction of at least a portion of a heart chamber, comprising:

providing a subject having a heart, comprising at least a portion having an activation; and applying a non-excitatory electric field to the portion at a delay after the activation, the field having a given duration of at least 101 msec and not lasting longer than the cycle length. Preferably the duration is longer, such as at least 120 msec or 150 msec.

There is further provided, in accordance with a preferred embodiment of the invention a method of modifying a force of contraction of at least a portion of a heart chamber, comprising:

providing a subject having a heart, comprising at least a portion having an activation; and applying a non-excitatory electric field having a given duration, at a delay after the activation, to the portion, wherein the portion of the chamber has an inner surface and an outer surface and wherein the field is applied between the inner surface and the outer surface.

There is further provided, in accordance with a preferred embodiment of the invention a method of modifying a force of contraction of at least a portion of a heart chamber, comprising:

providing a subject having a heart, comprising at least a portion having an activation; and applying a non-excitatory electric field having a given duration, at a delay after the activation, to the portion, wherein the portion of the chamber has an inner surface and an outer surface and wherein the field is applied along the outer surface.

There is further provided, in accordance with a preferred embodiment of the invention a method of modifying a force of contraction of at least a portion of a heart chamber comprising:

providing a subject having a heart, comprising at least a portion having an activation; and applying a non-excitatory electric field having a given duration, at a delay after the activation, to the portion, wherein the portion of the chamber has an inside surface, an outside surface and an intra-muscle portion and wherein the field is applied between the intra-muscle portion and at least one of the surfaces.

There is further provided, in accordance with a preferred embodiment of the invention a method of modifying a force of contraction of at least a portion of a heart chamber, comprising:

providing a subject having a heart, comprising at least a portion having an activation; and applying a non-excitatory electric field having a given duration, at a delay after the activation, to the portion, wherein the field is applied between a single electrode and a casing of an implanted device.

There is further provided, in accordance with a preferred embodiment of the invention a method of modifying a force of contraction of at least a portion of a heart chamber, comprising:

providing a subject having a heart, comprising at least a portion having an activation; and applying a non-excitatory electric field having a given duration, at a delay after the activation, to the portion, using an electrode floating inside the heart.

There is further provided, in accordance with a preferred embodiment of the invention a method of modifying a force of contraction of at least a portion of a heart chamber, comprising:

providing a subject having a heart, comprising at least a portion having an activation; and applying a non-excitatory electric field having a given duration, at a delay after the activation, to the portion, wherein the field is applied using at least two electrodes and wherein the at least two electrodes are at least 2 cm apart.

In preferred embodiments of the invention the electrodes are at least 4 or 9 cm apart.

There is further provided, in accordance with a preferred embodiment of the invention a method of modifying a force of contraction of at least a portion of a heart chamber, comprising:

providing a subject having a heart, comprising at least a portion having an activation; and applying a non-excitatory electric field having a given duration, at a delay after the activation, to the portion, wherein the field is applied using at least two electrodes and wherein one electrode of the at least two electrodes is at a base of a chamber of the heart and one electrode is at an apex of a chamber of the heart.

There is further provided, in accordance with a preferred embodiment of the invention a method of modifying a force of contraction of at least a portion of a heart chamber, comprising:

providing a subject having a heart, comprising at least a portion having an activation; and applying a non-excitatory electric field having a given duration, at a delay after the activation, to the portion, wherein the field is applied using at least three electrodes and wherein applying a non-excitatory field comprises:

electrifying a first pair of the at least three electrodes; and subsequently electrifying a second pair of the at least three electrodes.

There is further provided, in accordance with a preferred embodiment of the invention a method of modifying a force of contraction of at least a portion of a heart chamber, comprising:

providing a subject having a heart, comprising at least a portion having an activation; and applying a non-excitatory electric field having a given duration, at a delay after the activation, to the portion, wherein the field is applied using at least two electrodes placed externally to the subject.

There is further provided, in accordance with a preferred embodiment of the invention a method of modifying a force of contraction of at least a portion of a heart chamber, comprising:

providing a subject having a heart, comprising at least a portion having an activation; and applying a non-excitatory electric field having a given duration, at a delay after the activation, to the portion, wherein the electric field at least partially cancels electrotonic currents in at least the portion of the heart chamber.

There is further provided, in accordance with a preferred embodiment of the invention a method of modifying a force of contraction of at least a portion of a heart chamber, comprising:

providing a subject having a heart, comprising at least a portion having an activation;

applying a non-excitatory electric field having a given duration, at a delay after the activation, to the portion between two positions; and sensing an activation at a site between the two positions.

There is further provided, in accordance with a preferred embodiment of the invention a method of modifying a force of contraction of at least a portion of a heart chamber, comprising:

providing a subject having a heart, comprising at least a portion having an activation;

applying a non-excitatory electric field having a given duration, at a delay after the activation, to the portion between two positions; and sensing an activation at a site coinciding with one of the two positions.

There is further provided, in accordance with a preferred embodiment of the invention a method of modifying a force of contraction of at least a portion of a heart chamber, comprising:

providing a subject having a heart, comprising at least a portion having an activation;

applying a non-excitatory electric field having a given duration, at a delay after the to activation, to the portion between two positions;

sensing an activation at a site; and estimating the activation of the portion from the sensed activation.

Preferably sensing comprises sensing a value of a parameter of an ECG and wherein estimating comprises estimating the delay based on a delay value associated with the value of the parameter.

Preferably, the site is at a different chamber of the heart than the chamber at which the field is applied.

Preferably, the site is substantially the earliest activated site in the chamber of the portion.

There is further provided, in accordance with a preferred embodiment of the invention a method of modifying a force of contraction of at least a portion of a heart chamber, comprising:

providing a subject having a heart, comprising at least a portion having an activation;

applying a non-excitatory electric field having a given duration, at a delay after the activation, to the portion; and applying a second non-excitatory electric field to a second portion of the chamber.

There is further provided, in accordance with a preferred embodiment of the invention a method according to claim 36, wherein the second field is applied in the same cardiac cycle as the non-excitatory field.

Preferably, each portion has an individual activation to which the applications of the field thereat are synchronized.

Preferably, the second field has a different effect on the heart than the non-excitatory field.

Preferably, only the second non-excitatory field is applied during a different cardiac cycle.

There is further provided, in accordance with a preferred embodiment of the invention a method of modifying a force of contraction of at least a portion of a heart chamber, comprising:

providing a subject having a heart, comprising at least a portion having an activation;

estimating the activation at the portion; and applying a non-excitatory electric field having a given duration, at a delay after the estimated activation, to the portion.

There is further provided, in accordance with a preferred embodiment of the invention a method of modifying a force of contraction of at least a portion of a heart chamber, comprising:

providing a subject having a heart, comprising at least a portion having an activation;

applying a non-excitatory electric field having a given duration, at a delay after the activation, to the portion; and repeating application of the non-excitatory field, during a plurality of later heart beats, at least some of which are not consecutive.

Preferably, the method comprises gradually reducing the frequency at which beats are skipped during the repeated application.

There is further provided, in accordance with a preferred embodiment of the invention a method of modifying a force of contraction of at least a portion of a heart chamber, comprising:

providing a subject having a heart, comprising at least a portion having an activation;

applying a non-excitatory electric field having a given duration, at a delay after the activation, to the portion, wherein the portion has an extent; and changing the extent of the portion to which the field is applied, between beats.

There is further provided, in accordance with a preferred embodiment of the invention a method of modifying a force of contraction of at least a portion of a heart chamber, comprising:

providing a subject having a heart, comprising at least a portion having an activation;

irradiating the portion with light synched to the activation; and repeating irradiating at least 100 cardiac cycles, during a period of less than 1000 cardiac cycles.

There is further provided, in accordance with a preferred embodiment of the invention a method of modifying a force of contraction of at least a portion of a heart chamber, comprising:

providing a subject having a heart, comprising at least a portion having an activation;

irradiating the portion with radio frequency radiation synched to the activation; and repeating irradiating at least 100 cardiac cycles, during a period of less than 1000 cardiac cycles.

There is further provided, in accordance with a preferred embodiment of the invention a method of modifying a force of contraction of at least a portion of a heart chamber, comprising:

providing a subject having a heart, comprising at least a portion having an activation; and modifying the availability of calcium ions inside muscle fibers of the portion, during a period of time including a time less than 70 msec after the activation, in response to the activation.

There is further provided, in accordance with a preferred embodiment of the invention a method of modifying a force of contraction of at least a portion of a heart chamber, comprising:

providing a subject having a heart, comprising at least a portion having an activation; and modifying the transport rate of calcium ions inside muscle fibers of the portion, during a period of time less than 70 msec after the activation, in response to the activation.

There is further provided, in accordance with a preferred embodiment of the invention a method of modifying a force of contraction of at least a portion of a heart chamber, comprising:

providing a subject having a heart, comprising at least a portion having an activation; and modifying the availability of catecholamines at the portion in synchrony with the activation.

There is further provided, in accordance with a preferred embodiment of the invention a method of modifying the activation profile of at least a portion of a heart, comprising, mapping the activation profile of the portion;

determining a desired change in the activation profile; and modifying, using a non-excitatory electric field, the conduction velocity in a non-arrhythmic segment of the portion, to achieve the desired change.

In a preferred embodiment of the invention, wherein the desired change is an AV interval and wherein modifying comprises modifying the conduction velocities of purkinje fibers between an AV node and at least one of the ventricles in the heart.

In a preferred embodiment of the invention, the activation comprises an average activation of the portion.

In a preferred embodiment of the invention, the activation comprises an earliest activation.

In a preferred embodiment of the invention, the activation comprises a mechanical activation.

In a preferred embodiment of the invention, wherein the activation comprises an electrical activation.

In a preferred embodiment of the invention, wherein the portion comprises a plurality of subportions, each having an individual activation and wherein applying a field comprises applying a field to each subportion at a delay relative to the individual activation of the subportion.

In a preferred embodiment of the invention, applying a non-excitatory electric field comprises driving an electric current through the segment. Preferably, the current is less than 20 mA. In some embodiments of the invention the current is less than 8 mA, 5 mA, 3 mA. Preferably, the current is at least 0.5 mA. In some embodiments it is at least 1 or 3 mA.

In a preferred embodiment of the invention, the field is applied for a duration of between 10 and 140 msec. In other preferred embodiments it is applied for between 20 and 100 msec, or 60 and 90 msec.

In a preferred embodiment of the invention, the delay is less than 70 msec. In other preferred embodiments it is less than 40, 20, 5 or 1 msec. In some embodiments the delay is substantially equal to zero.

In a preferred embodiment of the invention, the delay is at least 1 msec. In other preferred embodiments it may be more than 3, 7, 15 or 30 msec.

In a preferred embodiment of the invention, the electric field has an exponential temporal envelope. In others it has a square, triangular, ramped or biphasic temporal envelope. Preferably the electric field comprises an AC electric field, preferably having a sinusoidal, saw tooth or square wave temporal envelope.

In a preferred embodiment of the invention, wherein the portion of the chamber has an inside surface and an outside surface, wherein the field is applied along the inner surface.

In a preferred embodiment of the invention, wherein the portion of the chamber has a normal conduction direction, wherein the field is applied along the normal conduction direction.

In a preferred embodiment of the invention, wherein the portion of the chamber has a normal conduction direction, wherein the field is applied perpendicular to the normal conduction direction.

In a preferred embodiment of the invention, the field is applied between at least two electrodes. Preferably, the electrodes are at least 2 cm apart. In some preferred embodiments the electrodes are at least 4 or 9 cm apart.

The chamber may be any of the left ventricle, the left atrium, the right ventricle or the right atrium.

A preferred embodiment of the invention includes pacing the heart. Preferably, applying the electric field is synchronized with the pacing.

In a preferred embodiment of the invention, the method includes calculating the delay based on the pacing.

In a preferred embodiment of the invention, the method includes sensing a specific activation at a site.

There is further provided, in accordance with a preferred embodiment of the invention, a method of modifying the activation profile of at least a portion of a heart, comprising, mapping the activation profile of the portion;

determining a desired change in the activation profile; and blocking the activation of at least a segment of the portion, to achieve the desired change, wherein the segment is not part of a reentry circuit or an arrhythmia foci in the heart.

In a preferred embodiment of the invention, the blocked segment is an ischemic segment.

There is further provided, in accordance with a preferred embodiment of the invention a method of modifying the activation profile of at least a portion of a heart, comprising, mapping the activation profile of the portion;

determining a desired change in the activation profile; and changing the refractory period of at least a segment of the portion, to achieve the desired change, wherein the segment is not part of a reentry circuit or an arrhythmia foci in the heart.

There is further provided, in accordance with a preferred embodiment of the invention a method of modifying the heart rate of a heart, comprising:

providing a subject having a heart with an active natural pacemaker region; and applying a non-excitatory electric field to the region.

Preferably, the electric field extends a duration of an action potential of the region.

Preferably the method comprises extending the refractory period of a significant portion of the right atrium.

There is further provided, in accordance with a preferred embodiment of the invention a method of reducing an output of a chamber of a heart, comprising:

determining the earliest activation of at least a portion of the chamber, which portion is not part of an abnormal conduction pathway in the heart; and applying a non-excitatory electric field to the portion.

Preferably, the field is applied prior to activation of the portion.

Preferably, the field reduces the reactivity of the portion to an activation signal.

Preferably, the field reduces the sensitivity of the portion to an activation signal.

There is further provided, in accordance with a preferred embodiment of the invention a method of reducing an output of a chamber of a heart, comprising:

determining an activation of and conduction pathways to at least a portion of the chamber; and reversibly blocking the conduction pathways, using a locally applied non-excitatory electric field.

There is further provided, in accordance with a preferred embodiment of the invention a method of reducing an output of a chamber of a heart, comprising:

determining an activation of and a conduction pathway to at least a portion of the chamber, which portion is not part of an abnormal conduction pathway in the heart; and reversibly reducing the conduction velocity in the conduction pathway, using a locally applied electric field.

There is further provided, in accordance with a preferred embodiment of the invention a method of performing cardiac surgery, comprising:

blocking the electrical activity to at least a portion of the heart using a non-excitatory electric field; and performing a surgical procedure on the portion.

There is further provided, in accordance with a preferred embodiment of the invention a method of performing cardiac surgery, comprising:

reducing the sensitivity to an activation signal of at least a portion of the heart using a non-excitatory electric field; and performing a surgical procedure on the portion.

There is further provided, in accordance with a preferred embodiment of the invention to a method of controlling the heart, comprising, providing a subject having a heart with a left ventricle and a right ventricle;

selectively reversibly increasing the contractility of one of the ventricles relative to the other ventricle.

Preferably, selectively reversibly increasing comprises applying a non-excitatory electric field to at least a portion of the one ventricle.

There is further provided, in accordance with a preferred embodiment of the invention a method of controlling the heart, comprising, providing a subject having a heart with a left ventricle and a right ventricle;

selectively reversibly reducing the contractility of one of the ventricles, relative to the other ventricle.

Preferably, selectively reversibly reducing comprises applying a non-excitatory electric field to at least a portion of the one ventricle.

There is further provided, in accordance with a preferred embodiment of the invention a method of treating a segment of a heart which is induces arrhythmias due to an abnormally low excitation threshold, comprising:

identifying the segment; and applying a desensitizing electric field to the segment, such that the excitation threshold is increased to a normal range of values.

There is further provided, in accordance with a preferred embodiment of the invention a method of modifying an activation profile of at least a portion of a heart, comprising:

determining a desired change in the activation profile; and reversibly blocking the conduction of activation signals across a plurality of elongated fence portions of the heart to achieve the desired change.

Preferably, blocking the conduction creates a plurality of segments, isolated from external activation, in the portion of the heart. Preferably, at least one of the isolated segments contains an arrhythmia foci. Preferably, at least one of the isolated segments does not contain an arrhythmia foci.

Preferably, the method includes individually pacing each of at least two of the plurality of isolated segments.

Preferably, blocking the conduction limits an activation front from traveling along abnormal pathways.

Preferably, reversibly blocking comprises reversibly blocking conduction of activation signals, synchronized with a cardiac cycle, to block abnormal activation signals.

In a preferred embodiment of the invention reversibly blocking comprises reversibly blocking conduction of activation signals, synchronized with a cardiac cycle, to pass normal activation signals.

There is further provided, in accordance with a preferred embodiment of the invention a method of treating abnormal activation of the heart, comprising:

detecting an abnormal activation state; and modifying the activation of the heart in accordance with the above described method to stop the abnormal activation condition.

In a preferred embodiment of the invention the abnormal condition is fibrillation.

There is further provided, in accordance with a preferred embodiment of the invention a method of controlling the heart comprising:

determining a desired range of values for at least one parameter of cardiac activity; and controlling at least a local force of contraction in the heart to maintain the parameter within the desired range.

Preferably, controlling includes controlling the heart rate.

Preferably, controlling includes controlling a local conduction velocity.

Preferably, the parameter responds to the control with a time constant of less than 10 minutes. Alternatively it responds with a time constant of more than a day.

There is further provided, in accordance with a preferred embodiment of the invention a method of controlling the heart, comprising:

determining a desired range of values for at least one parameter of cardiac activity;

controlling at least a portion of the heart using a non-excitatory electric field having at least one characteristic, to maintain the parameter within the desired range; and changing the at least one characteristic in response to a reduction in a reaction of the heart to the electric field.

Preferably, the characteristic is a strength of the electric field. Alternatively it comprises a duration of the electric field, a frequency of the field or a wave form of the field.

There is further provided, in accordance with a preferred embodiment of the invention a method of treating a patient having a heart with an unhealed infarct, comprising, applying any of the above methods, until the infarct is healed.

There is further provided, in accordance with a preferred embodiment of the invention a method of treating a patient having a heart, comprising, providing a patient, having an unhealed infarct in the heart; and applying one of the above methods until the heart is stabilized.

In a preferred embodiment of the invention applying a non-excitatory field comprises applying a non-excitatory field for between 3 and 5000 heart beats.

There is further provided, in accordance with a preferred embodiment of the invention apparatus for controlling a heart comprising:

a plurality of electrodes adapted to apply an electric field across at least a portion of the heart; and a power supply which electrifies the electrodes with a non-excitatory electric field, for a given duration at least 100 times during a period of less than 50,000 cardiac cycles.

Preferably, are electrified at least 1000 times during a period of less than 50,000 cardiac cycles. They may also be electrified at least 1000 times during a period of less than 20,000 cardiac cycles or at least 1000 times during a period of less than 5,000 cardiac cycles.

Preferably, the field is applied less than 10 times in one second.

In a preferred embodiment of the invention, the power supply electrifies the electrodes at least 2000 times over the period. In preferred embodiments the power supply electrifies the electrodes at least 4000 times over the period.

There is further provided, in accordance with a preferred embodiment of the invention apparatus for controlling a heart comprising:

a plurality of electrodes adapted to apply an electric field across at least a portion of the heart; and a power supply which electrifies the electrodes with a non-excitatory electric field, for a given duration, wherein at least one of the electrodes is adapted to cover an area of the heart larger than 2 cm$^2$.

Preferably at least one of the electrodes is adapted to cover an area of the heart larger than 6 or 9 cm$^2$.

There is further provided, in accordance with a preferred embodiment of the invention apparatus for controlling a heart comprising:

at least one unipolar electrode adapted to apply an electric field to at least a portion of the heart; and a power supply which electrifies the electrodes with a non-excitatory electric field.

Preferably the apparatus comprises a housing, which is electrified as a second electrode.

There is further provided, in accordance with a preferred embodiment of the invention apparatus for controlling a heart comprising:

a plurality of electrodes adapted to apply an electric field across at least a portion of the heart; and a power supply which electrifies the electrodes with a non-excitatory electric field, for a given duration, wherein the distance between the electrodes is at least 2 cm.

In preferred embodiments of the invention the distance is at least 4 or 9 cm.

There is further provided, in accordance with a preferred embodiment of the invention apparatus for controlling a heart comprising:

at least three electrodes adapted to apply an electric field across at least a portion of the heart; and a power supply which electrifies the electrodes with a non-excitatory electric field, for a given duration, wherein the electrodes are selectively electrifiable in at least a first configuration where two electrodes are electrified and in a second configuration where two electrodes, not both identical with the first configuration electrodes, are electrified.

There is further provided, in accordance with a preferred embodiment of the invention apparatus for controlling a heart comprising:

a plurality of electrodes adapted to apply an electric field across at least a portion of the heart;

a sensor which senses a local activation; and a power supply which electrifies the electrodes with a non-excitatory electric field, for a given duration, responsive to the sensed local activation.

Preferably the sensor senses a mechanical activity of the portion.

Preferably, the sensor is adapted to sense the activation at least one of the electrodes.

Preferably, the sensor is adapted to sense the activation in the right atrium.

Preferably, the sensor is adapted to sense the activation between the electrodes.

Preferably, the sensor senses an earliest activation in a chamber of the heart including the portion and wherein the power supply times the electrification responsive to the earliest activation.

There is further provided, in accordance with a preferred embodiment of the invention apparatus for controlling a heart comprising:

electrodes adapted to apply an electric field across elongate segments of at least a portion of the heart; and a power supply which electrifies the electrodes with a non-excitatory electric field.

Preferably, the electrodes are elongate electrodes at least one cm long. In other embodiments they are at least 2 or 4 cm long. Preferably the segments are less than 0.3 cm wide. In some embodiments they are less than 0.5, 1 or 2 cm wide.

Preferably, the power supply electrifies the electrodes for a given duration of at least 20 msec, at least 1000 times over a period of less than 5000 cardiac cycles.

In preferred embodiments of the invention, the elongate segments divide the heart into at least two electrically isolated segments in the heart.

There is further provided, in accordance with a preferred embodiment of the invention apparatus for controlling a heart comprising:

a plurality of electrodes adapted to apply an electric field across at least a portion of the heart;

a power supply which electrifies the electrodes with a non-excitatory electric field, for a given duration; and a circuit for determining an activation at a site in the portion, wherein the power supply electrifies the electrodes responsive to the determined activation.

Preferably, the electric field is applied at a given delay, preferably less than 70 msec, after an activation at one of the electrodes.

In a preferred embodiment of the invention the electric field is applied before an activation at one of the electrodes. In various preferred embodiments of the invention the field is applied more than 30, 50 or 80 msec before the activation.

Preferably, the circuit comprises an activation sensor which senses the activation.

Alternatively or additionally the activation is calculated, preferably based on an activation in a chamber of the heart different from a chamber including the portion.

Preferably the apparatus includes a memory which stores values used to calculate a delay time, associated with a value of at least a parameter of a sensed ECG. Preferably, the parameter is a heart rate.

There is further provided, in accordance with a preferred embodiment of the invention apparatus for controlling a heart comprising:

a plurality of electrodes adapted to apply an electric field across at least a portion of the heart;

a power supply which electrifies the electrodes with a non-excitatory electric field, for a given duration;

a sensor which measures a parameter of cardiac activity; and a controller which controls the electrification of the electrodes to maintain the parameter within a range of values.

The apparatus preferably comprises a memory which stores a map of electrical activity in the heart, wherein the controller uses the map to determine a desired electrification.

The apparatus preferably comprises a memory which stores a model of electrical activity in the heart, wherein the controller uses the model to determine a desired electrification.

There is further provided, in accordance with a preferred embodiment of the invention apparatus for controlling a heart comprising:

a plurality of electrodes adapted to apply an electric field across at least a portion of the heart;

a power supply which electrifies the electrodes with a non-excitatory electric field, for a given duration; and a controller which measures a reaction of the heart to the electrification of the electrodes.

Preferably, the controller changes the electrification based on the measured reaction.

Preferably, the apparatus includes a memory which stores the measured reaction.

There is further provided, in accordance with a preferred embodiment of the invention apparatus for controlling a heart comprising:

a plurality of electrodes adapted to apply an electric field across at least a portion of the heart;

a power supply which electrifies the electrodes with a non-excitatory electric field, for a given duration; and a pacemaker which paces the heart.

Preferably, the pacemaker and the remainder of the apparatus are contained in a common housing.

Preferably, the pacemaker and the remainder of the apparatus utilize common excitation electrodes. Preferably, the pacemaker and the remainder of the apparatus utilize a common power supply.

Preferably, the non-excitatory field is synchronized to the pacemaker.

Preferably, the electrodes are electrified using a single pulse which combines a pacing electric field and a non-excitatory electric field.

There is further provided, in accordance with a preferred embodiment of the invention apparatus for controlling a heart comprising:

a plurality of electrodes adapted to apply an electric field across at least a portion of the heart; and a power supply which electrifies the electrodes with a non-excitatory electric field, for a given duration, wherein at least one of the electrodes is mounted on a catheter.

There is further provided, in accordance with a preferred embodiment of the invention apparatus for controlling a heart comprising:

a plurality of electrodes adapted to apply an electric field across at least a portion of the heart; and a power supply which electrifies the electrodes with a non-excitatory electric field, for a given duration, wherein the electrodes are adapted to be applied externally to the body.

Preferably, the apparatus includes an external pacemaker.

Preferably, the apparatus comprises an ECG sensor, to which electrification of the electrodes is synchronized.

In a preferred embodiment of the invention the duration of the field is at least 20 msec.

In other preferred embodiments the duration is at least 40, 80 or 120.

In a preferred embodiment of the invention a current is forced through the portion between the electrodes.

Preferably, the apparatus includes at least another two electrodes, electrified by the power supply and adapted to apply a non-excitatory electric field across a second portion of the heart. Preferably, the apparatus comprises a controller which coordinates the electrification of all the electrodes in the apparatus.

Preferably, a peak current through the electrodes is less than 20 mA. In some preferred embodiments it is less than 10, 5 or 2 mA.

In preferred embodiments of the invention the electrodes are adapted to be substantially in contact with the heart.

Preferably the electric field has an exponential, triangular or square wave shape. The field may be unipolar or bipolar. The field may have a constant strength.

There is further provided, in accordance with a preferred embodiment of the invention apparatus for optical control of a heart, comprising:

at least one implantable light source which generates pulses of light, for at least 1000 cardiac cycles, over a period of less than 5000 cycles, and at least one wave guide for providing non-damaging intensities of light from the light source to at least one site on the heart.

Preferably, the at least one light source comprises a plurality of light sources, each attached to a different site on the heart.

Preferably, the wave guide is an optical fiber.

Preferably, the light source comprises a monochrome light source.

In a preferred embodiment of the invention the apparatus comprises a sensor, which measures an activation of at least portion of the heart, wherein the light source provides pulsed light in synchrony with the measured activation.

There is further provided, in accordance with a preferred embodiment of the invention a method of programming a programmable controller for a subject having a heart, comprising:

determining pulse parameters suitable for controlling the heart using non-excitatory electric fields; and programming the controller with the pulse parameters.

Preferably, determining pulse parameters comprises determining a timing of the pulse relative to a cardiac activity.

Preferably, the cardiac activity is a local activation.

Preferably, determining a timing comprises determining timing which does not induce fibrillation in the heart.

Preferably, determining a timing comprises determining a timing which does not induce an arrhythmia in the heart.

Preferably, determining a timing comprises determining the timing based on a map of an activation profile of the heart.

Preferably, determining a timing comprises calculating a delay time relative to a sensed activation.

Preferably, controlling the heart comprises modifying the contractility of the heart.

There is further provided, in accordance with a preferred embodiment of the invention a method of determining an optimal placement of at least two individual electrodes for controlling a heart using non-excitatory electric fields, comprising:

determining an activation profile of at least a portion of the heart; and determining an optimal placement of the electrodes in the portion based on the activation profile.

Preferably the method includes determining an optimal location for an activation sensor, relative to the placement of the electrodes.

Preferably, controlling comprises modifying the contractility.

Preferably, controlling comprises creating elongate non-conducting segments in the heart.

There is further provided, in accordance with a preferred embodiment of the invention a method of determining a timing parameter for a non-excitatory, repeatably applied pulse for a heart, comprising:

applying a non-excitatory pulse using a first delay;

determining if the pulse induces an abnormal activation profile in the heart; and repeating applying a non-excitatory pulse using a second delay, shorter than the first, if the pulse did not induce abnormal activation in the heart.

There is further provided, in accordance with a preferred embodiment of the invention a method of determining a timing parameter for a non-excitatory, repeatably applied pulse for a heart, comprising:

applying a non-excitatory pulse using a first delay;

determining if the pulse induces an abnormal activation profile in the heart; and repeating applying a non-excitatory pulse using a second delay, longer than the first, if the pulse did not induce abnormal activation in the heart.

There is further provided, in accordance with a preferred embodiment of the invention a method of programming a programmable controller for a heart, comprising:

controlling the heart using plurality of non-excitatory electric field sequences;

determining a response of the heart to each of the sequences; and programming the controller responsive to the response of the heart to the non-excitatory sequences.

There is further provided, in accordance with a preferred embodiment of the invention a method of controlling an epileptic seizure, comprising:

detecting an epileptic seizure in brain tissue; and applying a non-excitatory electric field to the brain tissue to attenuate conduction of a signal in the tissue.

There is further provided, in accordance with a preferred embodiment of the invention a method of controlling nervous signals in periphery nerves, comprising, selecting a nerve; and applying a non-excitatory electric field to the nerve to attenuate conduction of nervous signals in the nerve.

There is further provided, in accordance with a preferred embodiment of the invention a method of controlling a heart having a chamber comprising:

applying a non-excitatory electric field to a first portion of a chamber, such that a force of contraction of the first portion is lessened; and applying a non-excitatory electric field to a second portion of a chamber, such that a force of contraction of the second portion is increased, heart beat. Alternatively or additionally, the delay is at least 0.5 or 1 msec, optionally, 3 msec, optionally 7 msec and also optionally 30 msec.

There is further provided in accordance with a preferred embodiment of the invention, a method of controlling the heart including determining a desired range of values for at least one parameter of cardiac activity and controlling at least a local contractility and a local conduction velocity in the heart to maintain the parameter within the desired range.

Preferably, the parameter responds to the control with a time constant of less than 10 minutes, alternatively, the parameter responds to the control with a time constant of between 10 minutes and 6 hours, alternatively, with a time constant of between 6 hours and a day, alternatively, with a time constant between a day and a week, alternatively, a time constant of between a week and month, alternatively, a time constant of over a month.

There is also provided in accordance with a preferred embodiment of the invention, a method of controlling the heart, including determining a desired range of values for at least one parameter of cardiac activity, controlling at least a portion of the heart using a non-excitatory electric field having at least one characteristic, to maintain the parameter within the desired range and changing the at least one characteristic in response to a reduction in a reaction of the heart to the electric field. Preferably, the characteristic is the strength of the electric field. Alternatively or additionally, the characteristic is one or more of the duration of the electric field, its timing, wave form, and frequency.

In another preferred embodiment of the invention, the apparatus includes a sensor which measures a parameter of cardiac activity and a controller which controls the electrification of the electrodes to maintain the parameter within a range of values. Preferably, the apparatus includes a memory which stores a map of electrical activity in the heart, wherein the controller uses the map to determine a desired electrification. Alternatively or additionally, the apparatus includes a memory which stores a model of electrical activity in the heart, wherein the controller uses the model to determine a desired electrification.

There is also provided in accordance with a preferred embodiment of the invention, a method of controlling an epileptic seizure, including detecting an epileptic seizure in brain tissue and applying a non-excitatory electric field to the brain tissue to attenuate conduction of a signal in the tissue.

It is an object of some aspects of the present invention to provide methods and devices for pacing the heart with enhanced contractility of the heart muscle.

It is another object of some aspects of the present invention to provide methods and devices for pacing the heart with modification of pulsatile blood flow dynamics.

It is yet another object of some aspects of the present invention to provide methods and devices for pacing the heart with modulation of action potentials in the myocardium.

It is a further object of some aspects of the present invention to provide methods and devices for pacing the heart with increased cardiac output and/or modification of other cardiac performance parameters such as peak-systolic and end-diastolic pressure, afterload and blood perfusion profile.

In some aspects of the present invention, the enhancement of contractility or increased cardiac output may be alternately activated and de-activated while pacing pulses are applied to the heart.

In preferred embodiments of the present invention, an improved cardiac pacemaker applies an extended pacing signal to the heart, the signal comprising a pacing pulse or a periodic waveform, preferably a train of pulses, having an overall duration substantially longer than a pulse duration required for pacing the heart. Preferably, the overall duration is at least three times the chronaxie time. Further preferably, the overall duration is greater than 8 ms, more preferably, greater than 10 ms, and most preferably, greater than 20 ms. The pulse shape and duration are controlled, however, as described hereinbelow, so as to reduce the risk of arrhythmia that could arise from the long duration of the extended waveform.

Preferably, the electrical current applied in each pulse is substantially greater than twice the threshold required for pacing, and more preferably, greater than three times the threshold, although still substantially less than a level that would be required for cardioversion or defibrillation.

In those preferred embodiments of the present invention wherein the extended pacing signal comprises a periodic waveform, the waveform preferably has a period of at least 2 ms (i.e., repetition frequency of 500 s$^{-1}$), more preferably at least 10 ms, and most preferably at least 20 ms. The extended pacing waveform preferably comprises a pulse train, which is preferably superimposed on a DC offset. Each of the pulses in the train preferably has a duration of at least 1 ms. In some preferred embodiments, the period of the waveform varies over the duration of the signal, preferably increasing towards the end of the signal. Such an increase is believed to be effective in reducing the likelihood of inducing arrhythmias due to the extended overall duration of the signal.

The inventors have found that application of extended pacing signals in accordance with the principles of the present invention engenders a modulation of the action potential, leading to improvement of one or more cardiac performance parameters, particularly in connection with pulsatile blood flow from the heart. Such improvements may include enhanced contraction force of the heart muscle, increased cardiac output (i.e., increased stroke volume), decreased end-diastolic pressure, increased peak-systolic pressure, improved rate of pressure increase (dp/dt), increased afterload, improved cardiac efficacy and flow dynamics profile and improved cardiac index by comparison with pacing waveforms known in the art.

The present invention thus addresses the issue of the hemodynamic effect of the pacemaker in a novel manner. The stimulating signals it applies to the heart not only control the heart rate but also control the heart's contractility and therefore improve the hemodynamics based on a mechanism that has not been used in the art of pacing before and stands in contrast to the negative hemodynamic effects of pacemakers known in the art. Due to the major improvement in hemodynamic function consequent to the use of the present invention, it may benefit not only patients requiring pacemakers for rate control, but also patients who suffer from deteriorating functioning of the heart not necessarily related to the heart rhythm, such as patients who suffer from congestive heart failure (CHF). The extended pacing signals are preferably applied by a pacemaker, but may also be applied by a defibrillator device having a pacemaker backup.

It is believed that the enhancement of contractility in response to the extended pacing signals is due to a mechanism occurring at the individual myocyte level, probably a modification of the action potential due to an increased availability of calcium in heart cell membranes resulting from the pulses. In any case, the operation of the present invention is supported by experimental observation, on both individual muscle fibers and on complete, isolated hearts, as well as in vivo in large animal models, and is not dependent on any particular hypothesis.

It is further noted that the enhancement of cardiac function obtained by application of extended pacing signals in accordance with the principles of the present invention cannot be attributed to any mechanism disclosed in the prior art, such as those described in the above-mentioned article by Thakor et al. Thakor reported a slight improvement in dp/dt in an isolated heart muscle fiber, based on a mechanism of increased propagation speed, while applying pacing pulses and waveforms of substantially shorter duration and lower energy than in the present invention. By applying novel extended pacing signals, however, the present inventors, however, have demonstrated enhancement and control of the heart's pulsatile flow, as well as modulation of action potentials in the heart muscle, which were not observed by Thakor (or reported in the context of pacing by any other prior investigators) and would not have been possible under the experimental conditions described by Thakor.

Applying long-duration signals to the heart muscle may increase the risk of cardiac arrhythmia if some part of the signals extends beyond the absolute refractory period. Under these conditions, any rapid change in voltage applied to the heart can cause an additional, undesired excitation, which can be dangerous or even fatal to the patient, since it may lead to induction of ventricular tachycardia or fibrillation. Therefore, in some preferred embodiments of the present invention, the extended pacing signal has a slowly decaying trailing edge or waveform envelope, rather than terminating sharply as is known in the art. In some of these preferred embodiments, the trailing edge or envelope decays generally linearly or exponentially. In other preferred embodiments of the present invention, wherein the signal comprises a periodic waveform, the period increases over the duration of the signal; thus, when the signal comprises a pulse train, a later pulse or pulses in the train are longer than an earlier pulse or pulses.

Additionally or alternatively, when extended pacing signals are applied at multiple sites in the heart, as described further hereinbelow, the signals are preferably mutually timed responsive to the respective refractory periods at the sites so as reduce or eliminate the possibility of undesired (and possibly fatal) additional excitations. In other words, at each of the sites, the signal is terminated before the end of the respective refractory period. Properly synchronized multi-site application of the signals both increases the safety of the pacemaker and aids in synchronizing the contraction of two or more of the heart chambers.

In some preferred embodiments of the present invention, the pacemaker receives signals indicative of physiological parameters related to cardiac function, such as heart rate, cardiac output, LVP, ECG, or dp/dt of the left or right ventricle, and controls the application of the extended pacing signals responsive to the received cardiac function signals. In one such preferred embodiment, the pacemaker applies the extended pacing signals when the parameters are outside a predetermined range of desired values, for example, when the cardiac output is low. Alternatively or additionally, the pacemaker receives electrophysiological signals indicative of the propagation of action potentials in the heart. The signals are analyzed to detect the possible presence of abnormal activation in the heart. When the possibility of abnormal activation is detected, the pacemaker preferably modifies the extended pacing signals, for example, by reducing their duration and/or amplitude and/or the number of pulses in the train.

In one of these preferred embodiments, the electrophysiological signals comprise Monophasic Action Potentials (MAP), as are known in the art, which are preferably used to determine the duration of the refractory period and/or to detect abnormal local electrical activity at or adjacent to a pacing site in the heart. Principles and techniques of MAP measurement are described, for example, by M. R. Franz in "Method and Theory of Monophasic Action Potential Recording," *Prog Cardiovasc Dis* 33(6) (May-June, 1991), pp. 347-368, and in "Bridging the Gap between Basic and Clinical Electrophysiology: What Can Be Learned from Monophasic Action Potential Recordings?" in *Cardiovasc Electrophysiol* 5(8) (August, 1994), pp. 699-710, which are incorporated herein by reference. The pacemaker preferably controls the extended pacing signal so that the pacing signal duration does not exceed that of the refractory period.

In another preferred embodiment, the electrophysiological signals are captured using close bipolar sensing, wherein local electrical activity of the heart tissue is measured using two small electrodes a short distance apart. A differential signal measured between the two electrodes reflects propagation of the action potentials in a small area, having dimensions on the order of the distance between the electrodes. The differential signal is thus used to determine the time of onset and the duration of the local action potential at the location of the electrode and to accurately observe changes in the action potential due to application of the extended pacing signals. As described above, the pacemaker preferably controls the extended pacing signal so that the pacing signal duration does not exceed that of the refractory period and/or to discontinue the extended pacing signals if abnormal local electrical activity is observed to result from the pacing.

Further alternatively or additionally, cardiac electrophysiological activity is mapped prior to application of the pacing electrodes. The map thus generated is used in determining where the pacing electrode or electrodes should be positioned and/or in programming and controlling the extended pacing waveform.

In some preferred embodiments of the present invention, the extended pacing signal comprises a train of biphasic pulses. The inventors have observed that application of a train of two or more biphasic pulses, each pulse preferably having a duration of at least 5 ms, and more preferably at least 8-10 ms, substantially enhances the effect of increased contractility and cardiac output.

In some preferred embodiments of the present invention, the extended pacing signals are applied using one or more intracardiac electrodes, applied to the endocardium, and operating in either a unipolar or, more preferably, a bipolar configuration. The electrodes are preferably made of highly conductive material with a large effective surface area. When multiple electrodes are used, different ones of the electrodes may have different surface areas or different shapes, for example, elongated or patch shapes.

In some of these preferred embodiments, pacing signals are applied using multiple electrodes at different, respective sites in the heart, in one or more of the heart's chambers. In such embodiments, the signals are preferably applied to the different sites in sequence, timed and programmed so as to maximize a desired enhancement of cardiac function. In one such preferred embodiment, one of the multiple electrodes, which is preferably positioned in one of the atria of the heart, applies conventional pacing pulses, while another of the electrodes, preferably in one of the ventricles, applies the extended pacing signals. Other combinations and configurations are also possible and are within the scope of the present invention; and the application of the extended pacing signals can be incorporated into substantially any mode of pacing known in the art, including (but not limited to) VOO, VVI, OVO, VVT, VVIR, VDT, AOO, AAIR, ADI, VDD, DDD and DDTv pacing. Preferably, the electrodes are positioned and the pacing signals are programmed and controlled responsive to a map of cardiac electrical activity, as described hereinabove.

In other preferred embodiments of the present invention, the extended pacing pulses are applied using epicardial, transmyocardial or transvenous electrodes or a combination of such electrodes.

In some preferred embodiments of the present invention, the extended pacing signals are applied only when hemodynamic enhancement is desired, as described hereinabove, so as to conserve energy and extend the lifetime of a battery that powers the pacemakers. Preferably, when the extended pacing signal is not applied, the pacemaker applies conventional pacing pulses, as are known in the art, to pace the heart, or applies no pulses at all. Further preferably, both the extended pacing waveforms and the conventional pacing pulses are applied and modified responsive to signals indicative of cardiac function, as described above.

PCT patent application PCT/IL97/00236, published as WO1998/010832, assigned to the assignee of the present patent application and is incorporated herein by reference, also describes a pacemaker that gives cardiac output enhancement. This pacemaker applies both excitatory (pacing) and non-excitatory electrical stimulation pulses to the heart. By applying non-excitatory pulses of suitable strength, appropriately timed with respect to the heart's electrical activation, the contraction of selected segments of the heart muscle can be increased or decreased, thus increasing or decreasing the stroke volume of the heart.

Concepts of cardiac muscle stimulation are also described in the above-mentioned PCT patent application PCT/IL97/00012, published as WO1997/025098. This application describes the use of non-excitatory electric fields, applied via electrodes to selected areas of the heart muscle, to modify the muscular function and, inter alia, to strengthen a portion of the muscle and engender redistribution of cardiac muscle mass. Similarly, in a preferred embodiment of the present invention, extended pacing signals are applied to one or more selected areas of the heart in such a manner as to engender muscle mass redistribution. Such redistribution can have the effect not only of locally strengthening the heart muscle, but also improving the muscular performance and efficiency of the entire heart.

Although preferred embodiments are described herein with reference to pacing of the heart, it will be appreciated that the principles of the present invention may similarly be applied to pacing of other muscles, particularly smooth muscles, such as the larynx, esophagus, uterus, intestines or bladder, or of other excitable tissue, such as hormonal glands.

There is therefore provided, in accordance with a preferred embodiment of the present invention, apparatus for heart pacing with hemodynamic improvement, including:

one or more electrodes, which convey electrical signals to respective cardiac muscle segments; and signal generation circuitry, which applies an extended pacing signal, having an overall duration greater than three times a chronaxie time, to the one or more electrodes so as to pace the heart.

There is also provided, in accordance with a preferred embodiment of the present invention, a method for heart pacing with enhancement of cardiac contraction, including:

applying one or more electrodes to a subject's heart; and conveying an extended pacing signal, having an overall duration of at three times a chronaxie time, to the one or more electrodes so as to pace the heart.

Preferably, the overall duration is at least 10 ms, and more preferably at least 20 ms, but less than approximately 100 ms.

Preferably, the cardiac muscle segments to which the one or more electrodes are applied are characterized by a refractory period, and the overall duration of the signal is such that the signal terminates during the refractory period.

In a preferred embodiment, the signal has a leading edge and a trailing edge, and wherein the trailing edge is characterized by an absolute rate of voltage change substantially smaller than that of the leading edge. Preferably, the absolute rate of the voltage change is less than a minimum rate of change necessary to generate an action potential in the cardiac muscle segments.

Preferably, the signal has an amplitude at least three times as great as a threshold for pacing the heart, but not sufficient for cardioversion and, further preferably, a duration at least three times a threshold duration for pacing the heart at the amplitude of the signal.

There is further provided, in accordance with a preferred embodiment of the present invention, apparatus for heart pacing with hemodynamic improvement, including:
one or more electrodes, which convey electrical signals to respective cardiac muscle segments; and
signal generation circuitry, which applies an extended pacing signal, including a train of a plurality of biphasic pulses, to the one or more electrodes so as to pace the heart.

There is additionally provided, in accordance with a preferred embodiment of the present invention, a method for heart pacing with hemodynamic enhancement, including:
applying one or more electrodes to the heart; and
conveying an extended pacing signal, including a train of a plurality of biphasic pulses, to the one or more electrodes so as to pace the heart.

Preferably, each of the pulses in the train preferably has a pulse duration of at least 1 ms, and wherein the pulse train has a period of at least 5 ms, and more preferably of at least 20 ms. Preferably, the train of pulses includes a plurality of biphasic pulses. Further preferably, the train of pulses has a duty cycle between about 10% and 50%.

Preferably, the train of pulses includes square wave pulses or, alternatively, sinusoidal pulses.

There is moreover provided, in accordance with a preferred embodiment of the present invention, apparatus for heart pacing with hemodynamic enhancement, including:
one or more electrodes, which convey electrical signals to respective cardiac muscle segments; and
signal generation circuitry, which applies an extended pacing signal to the one or more electrodes so as to pace the heart, the signal having an amplitude at least three times as great as a threshold for pacing the heart, but not sufficient for cardioversion.

There is also provided, in accordance with a preferred embodiment of the present invention, a method for heart pacing with hemodynamic enhancement, including:
applying one or more electrodes to the heart; and
conveying an extended pacing signal to the one or more electrodes so as to pace the heart, the signal having an amplitude at least three times as great as a threshold for pacing the heart, but not sufficient for cardioversion.

Preferably, the signal has a duration at least three times a threshold duration for pacing the heart at the amplitude of the signal.

Preferably, application of the extended pacing signal modifies a characteristic of pulsatile flow of blood in the heart.

In a preferred embodiment, application of the extended pacing signal increases a stroke volume of the heart by at least 5%, and preferably by at least 10%, relative to the stroke volume when the heart is paced with pulses less than 2 ms in duration.

In another preferred embodiment, application of the extended pacing signal modifies a cardiac output of the heart by at least 5% relative to the cardiac output when the heart is paced with pulses less than 2 ms in duration at a pacing rate equal to that of the extended pacing signal.

In yet another preferred embodiment, application of the extended pacing signal increases a contractility of at least a portion of the heart by at least 10% relative to the contractility thereof when the heart is paced with pulses less than 2 ms in duration. Alternatively, application of the extended pacing signal decreases a contractility of at least a portion of the heart by at least 10% relative to the contractility thereof when the heart is paced with pulses less than 2 ms in duration.

In a preferred embodiment, application of the extended pacing signal modifies a muscular tension in the heart by at least 10% relative to the tension when the heart is paced with pulses less than 2 ms in duration.

Preferably, application of the extended pacing signal modifies the duration of an action potential in the respective cardiac muscle segments by at least 10% relative to the duration when the heart is paced with pulses less than 2 ms in duration.

Preferably, the signal generation circuitry includes a pulse generator and a DC offset generator, whose outputs are summed to provide the extended pacing signal.

In a preferred embodiment, the one or more electrodes include a plurality of electrodes, which are positioned in different chambers of the heart. Preferably, the signal includes a plurality of waveforms, which are applied respectively to the electrodes in the different chambers according to a predetermined time sequence. Further preferably, a pacing pulse having a duration less than 8 ms is applied to one or more of the electrodes positioned in a first one of the different chambers, and the extended pacing signal is applied to another one or more of the electrodes positioned in a second one of the different chambers.

In a preferred embodiment, the signal generation circuitry applies the extended pacing signal to the one or more electrodes in response to a demand for an enhancement of hemodynamic performance of the heart, wherein the enhancement of hemodynamic performance preferably includes an increase in cardiac output. Preferably, the apparatus includes a sensor which generates an output responsive to a physiological parameter indicative of the demand for the enhancement, wherein the signal generation circuitry applies the extended pacing signal responsive to the output from the sensor. Alternatively or additionally, in the absence of the demand for the enhancement, the signal generation circuitry applies pacing pulses to the electrodes of substantially lower energy than the extended pacing signal.

Preferably, the one or more electrodes include endocardial electrodes. Alternatively or additionally, the one or more electrodes include epicardial electrodes, transmyocardial electrodes or transvenous electrodes.

In a preferred embodiment, the apparatus includes a sensor, preferably an electrode, coupled to generate a signal responsive to activity of the heart, wherein the signal generation circuitry receives the signal from the sensor and modifies the extended pacing signal responsive thereto.

In a preferred embodiment, the electrode senses a Monophasic Action Potential signal.

In another preferred embodiment, the sensor includes a pair of closely-spaced bipolar electrodes, which sense a local endocardial action potential.

Preferably, the signal generation circuitry detects a possible arrhythmic stimulation of the heart and modifies the extended pacing signal so as to prevent the arrhythmic stimulation.

In a preferred embodiment, the one or more electrodes are applied such that conveying the extended pacing signal engenders a redistribution of cardiac muscle mass.

The present invention will be more fully understood from the following detailed description of the preferred embodiments thereof, taken together with the drawings in which:

BRIEF DESCRIPTION OF THE DRAWINGS

FIGS. 6A-6C are graphs showing the results of various experiments, in accordance with an embodiment of the present invention;

FIG. 8B is a series of graphs showing the repeatability of increasing contractility in various types of cardiac muscles, in accordance with a preferred embodiment of the invention;

FIGS. 9-18B are each a series of graphs showing experimental results from experiments in which an isolated rabbit heart was controlled in accordance with an embodiment of the present invention;

FIG. 26A is a schematic timing diagram illustrating a signal applied by the generator of FIG. 25, in accordance with a preferred embodiment of the present invention;

FIG. 26B is a schematic timing diagram illustrating a signal applied by the generator of FIG. 25, in accordance with an alternative preferred embodiment of the present invention;

FIG. 33 is a schematic block diagram illustrating a pacemaker for applying extended pacing signals, in accordance with a preferred embodiment of the present invention.

DETAILED DESCRIPTION OF PREFERRED EMBODIMENTS

One aspect of the present invention relates to controlling and/or modulating the contractility of a cardiac muscle segment and/or the plateau duration of an action potential of the cardiac muscle segment, by applying an electric field or current across the segment. As used herein, the terms, voltage, electric field and current are used interchangeably to refer to the act of supplying a non-excitatory signal to control cardiac activity. The actual method of applying the signal is described in more detail below.

Figure 1A:
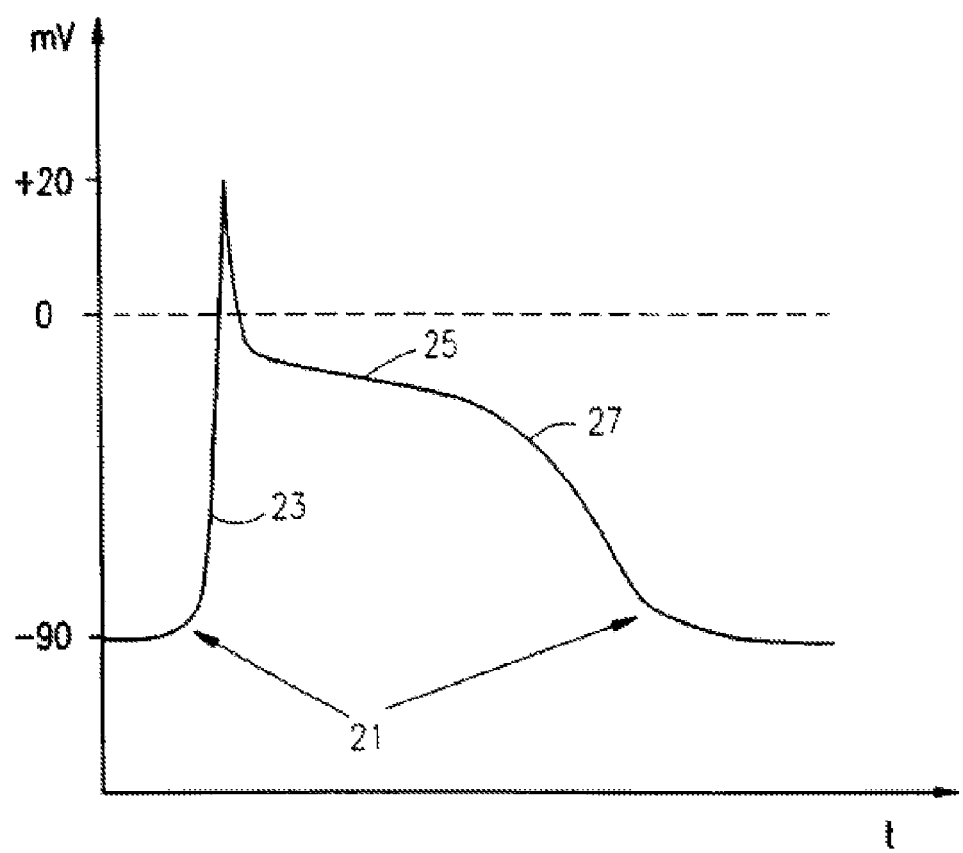
FIG. 1A is a schematic graph of a typical cardiac muscle action potential, in accordance with an embodiment of the present invention.
Figure 1B:
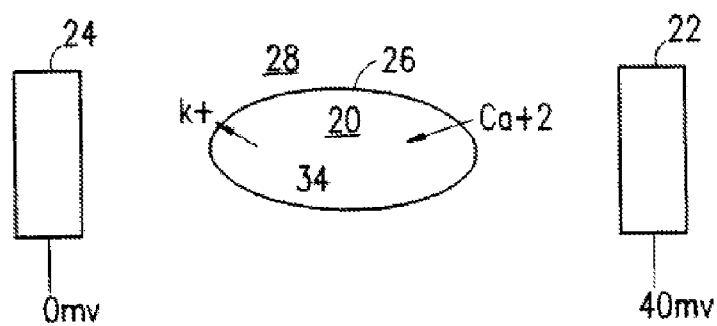
FIG. 1B is a schematic model of a cardiac muscle cell in an electrical field, in accordance with an embodiment of the present invention.

FIG. 1B shows a schematic model illustrating one possible explanation for the relation between an applied voltage and a resulting plateau duration, in accordance with an embodiment of the present invention. A cell 20, having a membrane 26, surrounded by extra-cellular fluid 28, is located in an electrical field generated by an electrode 22 and an electrode 24. Cell 20 has a −40 mV internal potential across membrane 26, electrode 22 has a potential of 40 mV and electrode 24 is grounded (to the rest of the body). During the action potential plateau, calcium ions enter the cell and potassium ions leave the cell through different membrane proteins. In this model, the external electric field caused by the voltage on the electrodes increases the potential of extra-cellular fluid 28. This reduces the outward movement of potassium ions from inside cell 20 and/or forces calcium ions into cell 20, either by changing the membrane potential, thus changing the electrochemical driving force of ions from both sides of the membrane or by changing the number of ionic channels being opened or closed.

In an additional or alternative model, the electric field generated by electrodes 22 and 24 causes an ionic flow between them. This flow is carried mainly by chlorine and potassium ions, since these are the ions to which membrane 26 is permeable, however, calcium ions may also be affected. In this model, calcium ions are drawn into cell 20 by the current while potassium ions are removed. Alternatively or additionally, sodium ions are removed instead of potassium ions. In any case, the additional calcium ions in the cell increase the contractility of cell 20 and are believed to extend the plateau duration.

Another additional or alternative model is that the electric field and/or the ionic current affect the opening and closing of voltage-gated channels (sodium, potassium and sodium-calcium). Further, the field may affect the operation of ionic pumps. One possible mechanism for this effect is that the applied electric field generates local "hot spots" of high electrical fields in the cell membrane, which hot spots can affect the opening and closing of ionic channels and/or pumps. Since creation of the hot spots is generally asymmetric with respect to the cell and since the channels themselves have an asymmetric behavior with respect to applied fields, more channels may be opened at one end of the cell than at the other. If, for example, more channels open at the negative end of the cell than at the positive end of the cell, the inflow of calcium ions will be greater than the outflow of these ions.

In accordance with yet another model, the controlling electric field increases the concentration of calcium in intracellular stores, which increased concentration may cause increased and/or faster supply of calcium during contraction, increasing the contractile force. Alternatively or additionally, the controlling electric field may directly affect the rate at which calcium is made available from the intracellular store, during contraction of the cell. Also, it may be that the controlling electric field directly increases the efficiency of the inflow of calcium, which causes an increase in the availability of calcium from the intracellular stores. It should be noted that in some physiological models of myocyte contraction, it is the rate of calcium flow which determines the contractility, rather than the total amount of calcium.

Different types of ionic channels and pumps have different operating characteristics. These characteristics include rates of flow, opening and closing rates, triggering voltage levels, priming and dependency on other ions for operating. It is thus possible to select a particular type of ionic channel by applying a particular strength of electric field, which strength also depends on whether the channels are open or closed at that moment, i.e., on the depolarization/repolarization phase of the cell. Different attributes of cellular activity may be controlled by controlling the ionic channels in this manner, since the activity of excitable tissues are well determined by their transmembrane potential and the concentrations of various types of ions inside and outside the cell.

Another model is that applying a non-excitatory electric fields induces the release of catecholamines (from nerve endings) at the treated portion of the heart. Another possibility is that the applied field facilitates the absorption of existing catecholamines by the cell.

Another, "recruitment", model, hypothesizes that the non-excitatory pulse recruits cardiac muscle fibers which are otherwise not stimulated by the activation signal. The non-excitatory pulse may work by lowering their depolarization threshold or by supplying a higher strength activation signal than is normal. However, it is generally accepted that cardiac muscle fibers function as a syncytium such that each cell contracts at each beat (described in an article entitled "Excitation Contraction Coupling and Cardiac Contractile Force", by Donald M. Bers, Chapter 2, page 17, Kluwer Academic, 1991, which is incorporated herein by reference).

Most probably, one or more of these models may be used to explain the activity of cell during different parts of the activation cycle. However, several major effects, including, increasing contractility, changing the self-activation rate, rescheduling of the repolarization, extension of plateau duration, hyperpolarization of cells, changing of membrane potential, changing of conduction velocity and inactivation of cells using electric fields, can be effected without knowing which model, if any, is correct.

As can be appreciated, the direction of the electric field may be important. First, conduction in cardiac cells is very anisotropic. Second, the distribution of local irregularities in the cell membrane is not equal, rather, irregularities are more common at ends of the cell; in addition, one cell end is usually more irregular than the other cell end. These irregularities may govern the creation of local high electric fields which might affect ionic channels. Third, some cardiac structures, such as papillary muscles, are better adapted to conduct an activation signal in one direction than in an opposite direction. Fourth, there exist rhythmic depolarization signals originating in the natural conductive system of the heart which are caused by the depolarization and repolarization of the heart muscle tissue itself. These signals may interfere with an externally applied electric field.

In one preferred embodiment of the invention, the purpose of a particular electric field is to induce an ionic current which is opposite to an ionic current induced by the voltage potential caused by the rhythmic depolarization of the heart. For example, the action potential plateau duration in cardiac muscle cells further from the earliest activation location is typically shorter than the duration of those cells nearer the earliest activation location. This shortening may result from different local ionic currents caused by the depolarization and repolarization of the heart and/or by different ionic current kinetics behavior at these locations. These ionic currents can be negated by applying an electric field of an equal magnitude and opposite direction to the field generated by the rhythmic depolarization.

Figure 2:
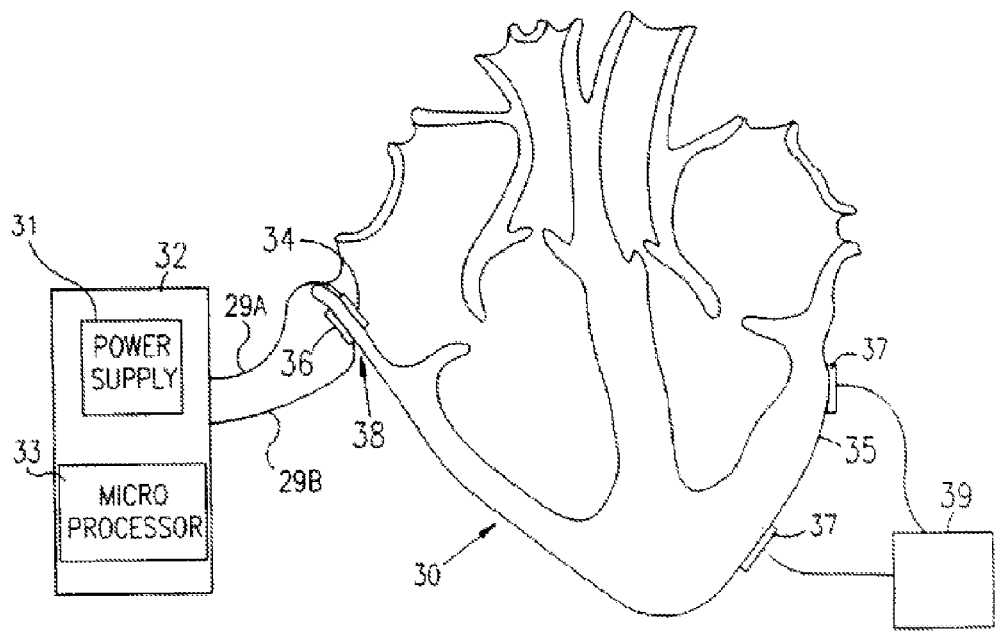
FIG. 2 is a schematic diagram of a heart having segments controlled in accordance with embodiments of the present invention, in accordance with an embodiment of the present invention.

FIG. 2 shows a heart 30 which is controlled using an electrical controller 32, in accordance with an embodiment of the present invention. A segment 38 of the right atrium is a controlled segment. In one preferred embodiment of the invention, the casing of controller 32 is one electrode and an electrode 36 is a second electrode for applying an electric field to segment 38. In another preferred embodiment of the invention, a second electrode 34 is used instead of the casing of controller 32. In a further preferred embodiment of the invention, the body of controller 32 is a ground, so that both electrode 34 and electrode 36 can be positive or negative relative to the rest of the heart. In another embodiment, electrode 34 is not directly connected to heart 30, rather, electrode 34 is floating inside the heart. In this embodiment, electrode 34 is preferably the current drain electrode. For illustrative purposes, controller 32 is shown including a power supply 31, leads 29A and 29B connecting the controller to the electrodes and a microprocessor 33 which controls the electrification of the electrodes.

In an alternative embodiment, also shown in FIG. 2, the electric field is applied along the heart wall, rather than across it. A segment 35 of the left ventricle is shown to be controlled by two electrodes 37 operated by a controller 39. Electrodes 37 may be placed on the surface of heart 30, alternatively, electrodes 37 may be inserted into the heart muscle. Further alternatively, the electrodes may be placed in blood vessels or in other body tissues which are outside of the heart, providing that electrifying the electrodes will provide a field or current to at least a portion of the heart. It should be noted that, since the control is synchronized to the cardiac cycle, even if the electrodes are outside the heart, there is substantially no change in position of the heart between sequential heart beats, so substantially the same portion of the heart will be affected each cardiac cycle, even if the electrodes are not mechanically coupled to the heart.

It another alternative embodiment of the invention, more than one pair of electrodes is used to control segment 35. In such an embodiment, each pair of electrodes may be located differently with respect to segment 35, for example, one pair of electrodes may be placed on the epicardium and a second pair placed inside the myocardium.

It should be appreciated that a current induced between the electrodes may cause electrolytic deposition on the electrodes over a period of time and/or may cause adverse physiological reactions in the tissue. To counteract this effect, in a preferred embodiment of the invention, the electric field is an AC electric field. In one preferred embodiment, the direction of the field is switched at a relatively low frequency, equal to or lower than the cardiac cycle rate. Preferably, the phase is inverted during a particular phase of the cardiac cycle for example, during diastole. In another preferred embodiment of the invention, the electric field has a frequency which is significantly higher than the cardiac cycle frequency.

Fast sodium channels, once inactivated require a certain amount of time at a negative potential to become ready for activation. As described, for example, in "Ionic Channels of Excitable Membranes", Bertil Hille, chapter 2, pp. 40 45, Sinaur Associates Inc., the disclosure of which is incorporated herein by reference. Since most sodium channels are not activated immediately at the onset of depolarization, applying a voltage at a high enough frequency can open the few channels that do react quickly to potential changes, while most of the channels will become inactivated and will not leave the inactivation stage. Thus, if the frequency of the field is high enough, certain ionic channels can be kept closed even though the average voltage is zero, with the result that the stimulated tissue is non-excitatory.

In accordance with another preferred embodiment of the invention, an AC field is overlaid on a DC field for controlling the heart. For example, an AC field having a amplitude of 20% that of the DC field and a frequency of 1 kHz may be used. Such an AC/DC controlling field has the advantage that the change in the applied field is higher, so that any reactions (on the part of the muscle cell) to changes in the field are facilitated, as are any reactions to the intensity of the field. The AC field in a combined AC/DC field or in a pure AC type field may have a temporal form of a sawtooth, a sinusoid or another form, such as an exponential or square wave pulse form.

In a DC type field, the temporal form of the field is preferably that of a constant amplitude pulse. However, in other embodiments of the invention, a triangular pulse, an exponential pulse, a ramp shaped pulse (increasing or decreasing), and/or a biphasic pulse form may be used.

Both AC and DC fields may be unipolar or bipolar. The terms AC and DC, as used herein to describe the electric field, relate to the number of cycles in a pulse. A DC field has at most one cycle, while an AC field may comprise many cycles. In other preferred embodiments of the invention, a train pulses may be applied, each train being of an AC or of a DC type.

Various types of ionic electrodes, such as Ag—AgCl electrodes, play electrodes, titanium electrodes with coatings such as nitrides and carbides, coated tantalum electrodes, pyrocarbon electrodes or carbon electrodes may be used. These electrodes generally reduce the amount of electrodeposition. The electrodes may be square, rectangular, or of any other suitable shape and may be attached by screwing the electrode into the myocardium or by clamping or by other attachment methods.

There are two preferred methods of delivering an electric field to a segment of the heart. In a first method, a current is forced through the segment of the heart which is to be controlled. Preferably, the current is a constant DC current. However, an AC current, as described above may also be used. In a second method, an electric field is applied across the heart (and maintained at a constant strength relative to the signal from). Generally, applying an electric field is easier and requires less power than inducing a current.

The timing of the application of the electric field (or current) relative to the local activity at segment 38 and relative to the entire cardiac cycle is important. In general, the application of the field may be synchronized to the local activation time if a local effect is desired, such as increasing the local contractility and/or plateau duration. The application of the field may be synchronized to the cardiac cycle in cases where a global effect is desired. For example, by hyperpolarizing cells in synchrony with the cardiac cycle it is possible to time their excitability window such that certain arrhythmias are prevented, as described in greater detail below. The application of the field may also be synchronized in accordance with a model of how the heart should be activated, in order to change the activation profile of the heart. For example, to increase the output of the heart, conduction velocities and/or conduction pathways may be controlled so that the heart contracts in a sequence deemed to be more optimal than a natural sequence. In particular, by controlling the conduction velocity at the AV node and/or at the left and right branches the AV interval may be increased or reduced. It should however be appreciated that the difference in activation times between different parts of the heart, especially in the same chamber of the heart, is usually quite small. For example, the propagation time of an activation signal in the left ventricle is approximately between 15 and 50 msec. If the control function may be achieved even if the timing of the application of the controlling field is locally off by 5 or 10 msec, then the control function can be achieved using a single pair of controlling electrodes.

Although, it is usually simplest to determine the local activation using a measured electrical activation time, it should be appreciated that the local activation of a tissue segment may be determined based on changes in mechanical activity, changes in position, velocity of motion, acceleration and even transmembrane potentials. Further, since in diseased tissue the delay between electrical activation and mechanical activation may be longer than in healthy tissue, the timing of the application of the field is preferably relative to the mechanical activation of the muscle.

In a preferred embodiment of the invention, the timing of the field is relative to the actual transmembrane potentials in the segments, not those which may be estimated from the electrogram and/or the mechanical. Thus, initiation of the field may be timed to the onset of the plateau to increase contractility. Alternatively, application of the field may be timed to specific transmembrane voltage levels. Further preferably, the strength and/or other parameters of the field, may be determined responsive to the actual transmembrane potentials and ionic concentrations achieved in cells of the segment. One way of determining the actual voltage levels is to inject a voltage sensitive dye into the cell and monitor it using an optical sensor, such as known in the art in experimental settings. One way of monitoring ionic concentrations, both intracellular and extracellular is by using concentration sensitive dyes.

If an electric field is applied before the activation signal reaches segment 38, the electric field can be used to reduce the sensitivity of segment 38 to the activation signal. One method of producing this effect is to apply a large electric field opposite to the direction of the activation signal and synchronized to it. This field will reduce the amplitude of the activation signal, so that it cannot excite cardiac tissue. Another method is to apply a strong positive potential on segment 38 before an activation signal reaches it, so that segment 38 is hyperpolarized and not sensitive to the activation signal. Removing the electric field does not immediately reverse this effect. Segment 38 stays insensitive for a short period of time and for a further period of time, the conduction velocity in segment 38 is reduced. In some cases however, removing the electric field will cause an action potential to occur. This action potential can be timed so that it occurs during a safe period with respect to the activation profile of the heart, so that if the segment generates an activation signal, this signal will not be to propagated to other parts of the heart. In some cases, the application of the field may affect the reactivity of the cells to the electrical potential rather and, in others, it may extend the refractory period. It should be noted that an electric field applied shortly after activation may also extend the refractory period, in addition to increasing the force of contraction.

It should be noted that, since the cardiac cycle is substantially reported, a delay before the activation time and a delay after the activation time may both be embodied using a system which delays after the activation time. For example, a field which should be applied 20 msec before the activation time, may be applied instead 680 msec after (assuming the cycle length is 700 msec).

Other applications of electric fields can increase the conduction velocity, especially where the conduction velocity is low as a result of tissue damage. Another method of controlling conduction is to apply an electric field similar to that used for defibrillation. When applied during the repolarization period of these cells, this type of electric field delays the repolarization. During this delayed/extended repolarization the cells are non-excitable. It should be appreciated that if this "defibrillation field" is applied using the techniques described herein (small, local and synchronized to a local activation time) the heart itself will not be defibrillated by the electric field. In one preferred embodiment of the invention, a locally defibrillated portion of the heart is isolated, by fences, from the rest of the heart.

Figure 3:
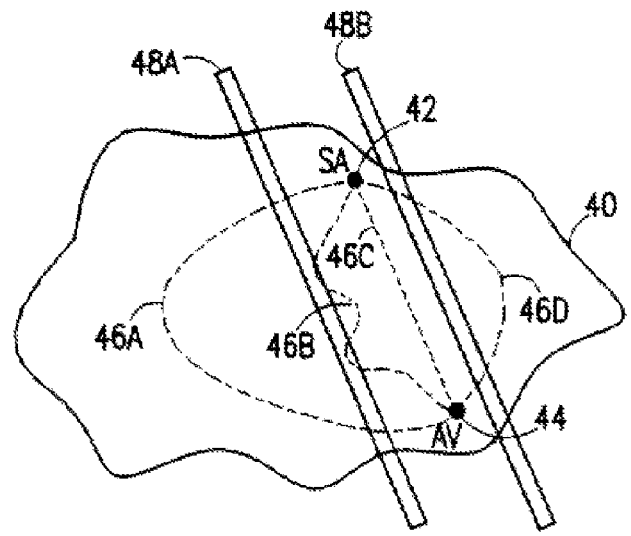
FIG. 3 is a schematic diagram of a segment of right atrial tissue with a plurality of conduction pathways, illustrating the use of fences, in accordance with a preferred embodiment of the present invention.

FIG. 3 illustrates one use of extending the refractory periods of cardiac tissue, in accordance with an embodiment of the present invention. Segment 40 is a portion of a right atrium. An activation signal normally propagates from an SA node 42 to an AV node 44. Several competing pathways, marked 46A 46D, may exist between SA node 42 and AV node 44, however, in healthy tissue, only one signal reaches AV node 44 within its excitability window. In diseased tissue, several signals which have traveled in different paths may serially excite AV node 44 even though they originated from the same action potential in the SA node. Further, in atrial fibrillation, the entire right atrium may have random signals running through it. In a preferred embodiment of the invention, electric fields are applied to a plurality of regions which act as "fences" 48A and 48B. These fences are non-conducting to activation signals during a particular, predetermined critical time, depending on the activation time of the electric fields. Thus, the activation signal is fenced in between SA node 42 and AV node 44. It is known to perform a surgical procedure with a similar effect (the "maze" procedure), however, in the surgical procedure, many portions of the right atrium need to be ablated to produce permanent insulating regions (fences). In the present embodiment of the invention, at least portions of fences 48A and 48B may be deactivated after the activation signal has passed, so that the atrium can contract properly.

In a preferred embodiment of the invention, a fence is applied using a linear array of bipolar electrodes. In another preferred embodiment of the invention, a fence is applied using two (slightly) spaced apart elongate wire electrodes of opposite polarity. Preferably, portions of the wire electrodes are isolated, such as segments 0.5 cm long being isolated and segments 0.5 cm long being exposed.

Still another preferred embodiment of the invention relates to treating ventricular fibrillation (VF). In VF, a ventricle is activated by more than one activation signal, which do not activate the ventricle in an orderly fashion. Rather, each segment of the ventricle is randomly activated asynchronously with the other segments of the ventricle and asynchronously with the cardiac cycle. As a result, no pumping action is achieved. In a preferred embodiment of the invention, a plurality of electrical fences are applied in the affected ventricle to damp the fibrillations. In general, by changing the window during which segments of the ventricle are sensitive to activation, a fibrillation causing activation signal can be blocked, without affecting the natural contraction of the ventricle. In one embodiment of the invention, the fences are used to channel the activation signals along correct pathways, for example, only longitudinal pathways. Thus, activation signals cannot move in transverse direction and transverse activation signals will quickly fade away, harmlessly. Healthy activation signals from the AV node will not be adversely affected by the fences. Alternatively or additionally, fences are generated in synchrony with the activation signal from the AV node, so that fibrillation causing activation signals are blocked. Further alternatively, entire segments of the ventricle are desensitized to the activation signals by applying a positive potential to those segments deemed sensitive to fibrillation.

Dividing the heart into insulated segments using fences is useful for treating many types of arrhythmias. As used herein, the term insulated means that conduction of the activation signal is blocked or slowed down or otherwise greatly reduced by deactivating portions of the heart conduction system. For example, many types of ventricular tachycardia (VT) and premature beats in the heart are caused by local segments of tissue which generate a pacing signal. These segments can be insulated from other segments of the heart so that only a small, local segment is affected by the irregular pacing. Alternatively, these diseased segments can be desensitized using an electric field, so that they do not generate incorrect activation signals at all.

Premature beats are usually caused by an oversensitive segment of the heart. By applying a local electric field to the segment, the sensitivity of the segment can be controlled and brought to similar levels as the rest of the heart, solving the major cause of premature beats. This technique is also applicable to insensitive tissues, which are sensitized by the application of a local electric field so that they become as sensitive as surrounding tissues.

It should be appreciated that it is not necessary to know the exact geometrical origin of an arrhythmia to treat it using the above described methods. Rather, entire segments of the heart can be desensitized in synchrony with the cardiac cycle so that they do not react before the true activation signal reaches them. Further, the heart can be divided into isolated segments or fenced in without mapping the electrical system of the heart. For example, electrodes can be inserted in the coronary vessels to create fences in the heart. These fences can block most if not all of the irregular activation signals in the heart and still allow "correct" activation signals to propagate by synchronizing the generation of these fences to the "correct" cardiac activation profile. Alternatively or additionally, each isolated segment is paced with an individual electrode. Alternatively, an array of electrodes may be implanted surrounding the heart so that it is possible to individually control substantially any local portion thereof.

In an additional preferred embodiment of the present invention, segments of the heart are continuously controlled using an electric field, so that their membrane potential at rest is below −60 mV. Below this level, the voltage-gated sodium channels cannot be opened by an activation signal. It is not usually possible to clamp all of the cells in a tissue segment to this voltage, so some of the cells in the tissue will typically be excitable. However, it is known that hyperpolarization causes depletion of potassium ions in the extracellular spaces surrounding individual cardiac muscle cells, which will cause a general reduction in the excitability of all the cells which share the same extracellular spaces. As described, for example, in "K+ Fluctuations in the Extracellular Spaces of Cardiac Muscle: Evidence from the Voltage Clamp and Extracellular K+—Selective Microelectrodes", Cohen I and Kline R, Circulation Research, Vol. 50, No. 1, pp. 1 16, January 1982, the disclosure of which is incorporated herein by reference. Thus, the reaction of the segments of the heart to an activation signal is reduced, has a longer delay and the propagation velocity in those segments is significantly reduced. Other resting potentials may affect the opening of other voltage-gated channels in the cell.

Another preferred embodiment of the invention relates to cardiac surgery. In many instances it is desirable to stop the pumping action of the heart for a few seconds or minutes necessary to complete a suture or a cut or to operate on an aneurysm. Current practice is not very flexible. In one method, the heart is bypassed with a heart-lung machine and the heart itself is stopped for a long period of time. This process is not healthy for the patient as a whole or for the heart itself and, often, serious post-operative complications appear. In another method, the heart is cooled down to reduce its oxygen consumption and it is then stopped for a (non-extendible) period of a few minutes. The period is non-extendible in part since during the stoppage of the heart the entire body is deprived of oxygen. In these methods, the heart is usually stopped using a cardioplesic solution. In a third method fibrillation is induced in the heart. However, fibrillation is known to cause ischemia, due to the greatly increased oxygen demand during fibrillation and the blockage of blood flow in the coronary arteries by the contraction of the heart muscle. Ischemia can irreversibly damage the heart.

Cessation or reduction of the pumping activity of the heart may be achieved using methods described herein, for example, fencing. Thus, in a preferred embodiment of the invention, the pumping action of the heart is markedly reduced using techniques described herein, repeatedly and reversibly, for short periods of time. It should be appreciated that due to the simplicity of application and easy reversibility, stopping the heart using electrical control is more flexible than currently practiced methods. Electrical control is especially useful in conjunction with endoscopic heart surgery and endoscopic bypass surgery, where it is desirable to reduce the motion of small segments of the heart.

Another preferred embodiment of the present invention relates to treating ischemic portions of the heart. Ischemic portions, which may be automatically identified from their injury currents using locally implanted sensors or by other electro-physiological characterization, may be desensitized or blocked to the activation signal of the heart. Thus, the ischemic cells are not required to perform work and may be able to heal.

U.S. provisional application 60/009,769 entitled "Cardiac Electromechanics", filed on Jan. 11, 1996, by Shlomo Ben-Haim and Maier Fenster, and its corresponding Israeli patent application No. 116,699 titled "Cardiac Electromechanics", filed on Jan. 8, 1996 by applicant Biosense Ltd., the disclosures of which are incorporated herein by reference, describe methods of cardiac modeling and heart optimization. In cardiac modeling, the distribution of muscle mass in the heart is changed by changing the workload of segments of the heart or by changing the plateau duration of action potentials at segments of the heart. These changes may be achieved by changing the activation profile of the heart. Plateau duration can be readily controlled using methods as described hereinabove. Further, by controlling the conduction pathways in the heart, according to methods of the present invention, the entire activation profile of the heart can be affected. In cardiac optimization as described in these applications, the activation profile of the heart is changed so that global parameters of cardiac output are increased. Alternatively, local physiological values, such as stress, are redistributed to relieve high-stress locations in the heart. In a preferred embodiment of the present invention, the activation profile may be usefully changed using methods as described hereinabove.

In order to best implement many embodiments of the present invention, it is useful to first generate an electrical, geometrical or mechanical map of the heart. U.S. patent application Ser. No. 08/595,365, now U.S. Pat. No. 5,738,096, entitled "Cardiac Electromechanics", filed on Feb. 1, 1996, by Shlomo Ben-Haim, and two PCT applications filed in Israel, on Jan. 8, 1997 and entitled "Cardiac Electromechanics", published as WO 1997/024981, and "Mapping Catheter", published as WO1997/024983, the disclosures of which are incorporated herein by reference, describe maps and methods and means for generating such maps. One particular map which is of interest is a viability map, in which the viability of different segments of heart tissue is mapped so as to identify hibernating and/or ischemic tissue. U.S. Pat. No. 5,391,199, U.S. patent application Ser. No. 08/293,859, filed on Aug. 19, 1994, titled "Means and Method for Remote Object Position and Orientation Detection System" and PCT Patent application U.S. Ser. No. 95/01103, now published as WO96/05768 on Feb. 29, 1996, the disclosures of which are incorporated herein by reference, describe position sensing means suitable for mounting on a catheter which is especially useful for generating such maps. Such position sensing means may also be useful for correctly placing electrodes in the heart if the electrodes are implanted using minimally invasive techniques such as those using endoscopes, thoracoscopes and catheters.

In one preferred embodiment of the invention, a map of the heart is used to determine which portions of the heart are viable, and thus, can be controlled to increase the cardiac output. Preferably, the entire activation profile of the heart is taken into account when determining to which portions of the heart a controlling field should be applied, to maximize a parameter of cardiac output. The activation profile may also determine the timing of the application of the field. A perfusion map may be used to access the blood flow to various portions of the heart. It is to be expected that increasing the contractility of a segment of heart muscle also increases the oxygen demand of that segment. Therefore, it is desirable to increase is the contractility only of those segments which have a sufficient blood flow. Possibly, the oxygen demands of other segments of the heart is reduced by proper controlling of the activation sequence of the heart.

Alternatively or additionally to mapping the perfusion and/or viability of the heart, the onset of controlling the heart may be performed gradually. Thus, the cardiac blood supply has time to adapt to the increased demand (if any) and to changes in supply patterns. In addition, the increase in demand will not be acute, so no acute problems (such as a heart attack) are to be expected as a result of the controlling. In one embodiment, the controlling is applied, at first, only every few heart beats, and later, every heart beat. Additionally or alternatively, the duration of a controlling pulse is gradually increased over a long period of time, such as several weeks. Additionally or alternatively, different segments are controlled for different heart beats, to spread the increased demand over a larger portion of the heart.

In an alternative preferred embodiment of the invention, the contractility of the heart is controlled only during the day and not during the night, as the cardiac demand during the day time is typically greater than during the night. Alternatively or additionally, the controller is used for a short time, such as 15 minutes, in the morning, to aid the patient in getting up. Alternatively or additionally, a controlling electric field is applied only once every number of beats (day and/or night). Further alternatively, the heart is controlled for a short period of time following an acute ischemic event, until the heart recovers from the shock. One preferred controlling method which may be applied after a heart attack relates to preventing arrhythmias. Another preferred controlling is desensitizing infarcted tissue or reducing the contractility of such tissue or electrically isolating such tissue so as to reduce its oxygen demands and increase its chance of healing.

One benefit of many embodiments of the present invention, is that they can be implemented without making any structural or other permanent changes in the conduction system of the heart. Further, many embodiments may be used in conjunction with an existing pacemaker or in conjunction with drug therapy which affects the electrical conduction in the heart. In addition, different controlling schemes may be simultaneously practiced together, for example, controlling the heart rate and increasing contractility in the left ventricle.

It must be appreciated however, that, by changing the activation profile of the heart, some changes may be effected on the structure of the heart. For example, cardiac modeling, as described above, may result from activation profile changes; over time.

Figure 4A:
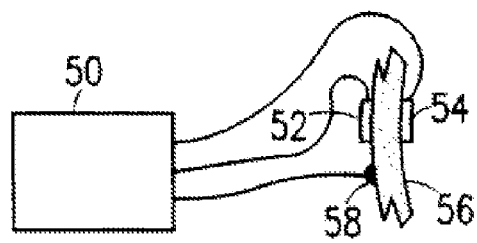
FIG. 4A is a schematic diagram of an electrical controller connected to a segment of cardiac muscle, in accordance with a preferred embodiment of the invention.

FIG. 4A is a schematic diagram of an electrical controller 50, in operation, in accordance with a preferred embodiment of the invention. A muscle segment 56, which is controlled by controller 50, is preferably electrified by at least one electrode 52 and preferably by a second electrode 54. Electrode 54 may be electrically floating. A sensor 58 may be used to determine the local activation time of segment 56, as an input to the controller, such as for timing the electrification of the electrodes. Other additional or alternative local and/or global cardiac parameters may also be used for determining the electrification of the electrodes. For example, the electrode(s) may be used to sense the local electrical activity, as well known in the art. Alternatively, sensor 58 is located near the SA node for determining the start of the cardiac rhythm. Alternatively, sensor 58 is used to sense the mechanical activity of segment 56, of other segments of the heart or for sensing the cardiac output. Cardiac output may be determined using a pressure sensor or a flow meter implanted in the aorta. In preferred embodiment of the invention, sensor 58 senses the electrical state of the heart, controller 50 determines a state of fibrillation and electrifies electrodes 52 and 54 accordingly.

Sensor 58 may be used for precise timing of the electrification of electrodes 52 and 54. One danger of incorrect electrification of the electrodes is that if the electrodes are electrified before an activation front reaches segment 56, the electrification may induce fibrillation. In a preferred embodiment of the invention, sensor 58 is placed between electrodes 52 and 54 so that an average activation time of tissue at the two electrodes is sensed. It should be appreciated that the precise timing of the electrification depends on the propagation direction of the activation front in the heart. Thus, if tissues at electrodes 52 and 54 are activated substantially simultaneously, the controlling field can be timed to be applied shortly thereafter. However, if tissue at one electrode is activated before tissue at the other electrode, the delay time in electrifying the electrodes must be longer. Thus, the optimal delay time in electrifying an electrode after the local activation time is dependent, among other things, on the orientation of the electrodes relative to the activation front. The conduction velocity of the activation front is affected in a substantial manner by the orientation of the cardiac muscle fibers. Thus, the orientation of the electrodes relative to the muscle fiber direction also has an effect on the optimal delay time.

In another preferred embodiment of the invention, local activation time (and electrification of electrodes 52 and 54) is estimated, based on a known propagation time of the activation signal. For example, if sensor 58 is placed in the right atrium, a delay of about 120 msec may be expected between the sensing of an activation signal at sensor 58 and the arrival of the activation signal at electrodes 52 and 54. Such delays can also be estimated. Within a single chamber, for example, it takes about 30 50 msec for the activation front to cover all the left ventricle. A sensor 58 may be placed at a location in the left ventricle which is excited relatively early by the activation signal. In a preferred embodiment of the invention, activation propagation times between implanted sensors and electrodes are measured in at least one heart activation profile (such as at a resting heart rate) and are used to estimate a desired delay in electrification of electrodes. It should be appreciated that, in diseased hearts, local conduction velocity may change substantially in time, thus, learning of and adaptation to the changes in local activation are a desirable characteristic of controller 50. In a preferred embodiment of the invention, a particular state of arrhythmia (or activation profile) is determined based on a parameter of the ECG, such as the morphology and/or the frequency spectrum of either an external or an internal ECG. Controller 50 determines the controlling profile based on the determined state. In particular, delay times, as described herein, may be associated with states, so that the exact delay time for the activation may be decided in real-time for each state of arrhythmia. Preferably, the delay times are precalculated and/or are determined during a learning state of controller 50, in which stage, an optimal delay time is determined for a particular activation state and stored in association therewith.

Sensor 58 may be placed on the epicardium, on the endocardium or, in a preferred embodiment of the invention, sensor 58 is inserted into the myocardium.

Figure 4B:
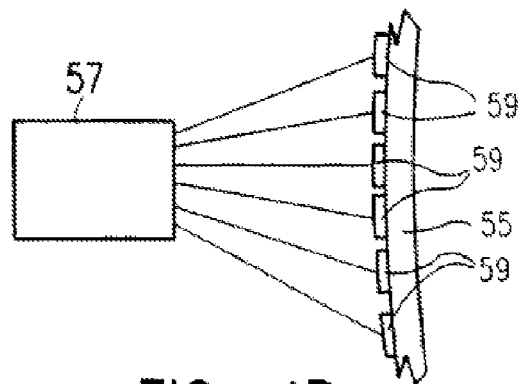
FIG. 4B is a schematic diagram of an electrical controller connected to a segment of cardiac muscle, in accordance with a preferred embodiment of the invention.

FIG. 4B shows an alternative embodiment of the invention, wherein a heart segment 55 is controlled by a plurality of electrodes 59 which are connected to a controller 57, in accordance with an embodiment of the present invention. The use of many electrodes enables greater control of both spatial and temporal characteristics of the applied electric field. In one example, each one of electrodes 59 is used to determine its local activation. Controller 57 individually electrifies electrodes 59 according to the determined activation. Preferably, the electrodes are activated in pairs, with current flowing between a pair of electrodes whose local activation time is known.

Different embodiments of the present invention will typically require different placement of the control electrodes. For example, some embodiments require a large area electrode, for applying an electric field to a large portion of the heart. In this case, a net type electrode may be suitable. Alternatively, a large flat electrode may be placed against the outside of the heart. Other embodiments require long electrodes, for example, for generating fences. In this case, wires are preferably implanted in the heart, parallel to the wall of the heart. Optionally, the electrodes may be placed in the coronary vessels outside the heart. In some aspects of the invention electrodes are placed so that the field generated between the electrodes is parallel to the direction in which activation fronts normally propagate in the heart, in others, the field is perpendicular to such pathways.

In one preferred embodiment of the invention, a pacemaker is provided which increases the cardiac output. A pacemaker activation pulse is usually a single pulse of a given duration, about 2 msec in an internal pacemaker and about 40 msec in an external pacemaker. In accordance with a preferred embodiment of the invention, a pacemaker generates a double pulse to excite the heart. A first portion of the pulse may be a stimulation pulse as known in the art, for example, 2 mA (milliamperes) constant current for 2 msec. A second portion of the pulse is a pulse as described herein, for example, several tens of msec long and at a short delay after the first portion of the pacemaker pulse. Alternatively, a very long stimulation pulse may be used. This type of pacemaker preferably uses two unipolar electrodes, one at the apex of the heart and one at the top of the left ventricle (or the right ventricle if it the right ventricular activity is to be increased).

In a preferred embodiment of the invention, a controller is implanted into a patient in which a pacemaker is already implanted. The controller is preferably synchronized to the pacemaker by connecting leads from the controller to the pacemaker, by sensors of the controller which sense the electrification of the pacemaker electrodes and/or by programming of the controller and/or the pacemaker.

In a preferred embodiment of the invention, the pacemaker adapts to the physiological state of the body in which it is installed by changing the heart's activity responsive to the physiological state. The pacemaker can sense the state of the body using one or more of a variety of physiological sensors which are known in the art, including, pH sensors, $pO_2$ sensors, $pCO_2$ sensors, blood-flow sensors, acceleration sensors, respiration sensors and pressure sensors. For example, the pacemaker can increase the flow from the heart in response to an increase in $pCO_2$. Since the control is usually applied in a discrete manner over a series of cardiac cycles, this control may be termed a control sequence. The modification in the heart's activity may be applied gradually or, preferably, in accordance with a predetermined control sequence.

In one aspect of the invention, target values are set for at least one of the measured physiological variables and the pacemaker monitors these variables and the effect of the control sequence applied by the pacemaker to determine a future control sequence. Once the discrepancy between the target value and the measured value is low enough, the control sequence may be terminated. As can be appreciated, one advantage of a cardiac controller over a pacemaker is that it can control many aspect of the heart's activation profile. As a result, the controller can determine a proper tradeoff between several different aspects of the activation profile of the heart, including, heart output, oxygenation of the cardiac muscle, contractile force of the heart and heart rate.

Another aspect of the invention relates to modifying the relation between the contraction of the left ventricle and the contraction of the right ventricle. In a healthy heart, increased contractility of the left ventricle is followed by increased contractility of the right ventricle, as a result of the increased output of the left ventricle, which causes an increase in the preload of the right ventricle. Decreased left ventricular output reduces the right ventricular output in a similar manner. In some cases, such as pulmonary edema, it may be desirable to modify the flow from one ventricle without a corresponding change in the flow from the other ventricle. This may be achieved by simultaneously controlling both ventricles, one control increasing the flow from one ventricle while the other control decreases the flow from the other ventricle. This modification will usually be practiced for short periods of time only, since the vascular system is a closed system and, in the long run, the flow in the pulmonary system is the same as in the general system. In a preferred embodiment of the invention, this modification is practiced by controlling the heart for a few beats, every certain period of time.

Another aspect of the present invention relates to performing a complete suite of therapies using a single device. A controller in accordance with a preferred embodiment of the invention includes several therapies which it can apply to the bean, including for example, increasing contractility, defibrillation, fencing, heart rate control and pacing. The controller senses (using physiological sensors) the state of the body and decides on an appropriate short-term therapy, for example, defibrillation to overcome fibrillation, increasing the heart rate to increase the cardiac outflow or applying fences to restrain a sudden arrhythmia Additionally or alternatively, such a controller can change the applied control sequence in response to long term therapeutic goals. For example, if increasing contractility is used to increase the muscle mass in a portion of the hear once a required muscle mass is reached, the control sequence may be stopped. This is an example of a therapeutic treatment affected by the controller. In another example, a few weeks after the device is implanted and programmed to increase the cardiac output to a certain target variable, the target variable may be changed. Such a change may be mandated by an expected period of time over which the heart adapts to the controller. One such adaptation is that the heart becomes stronger and/or more efficient. Another such adaptation may be that the heart reduces its response to the control sequence, so that a different control sequence may be required to achieve the same goals. In a preferred embodiment of the invention, the control sequence is varied every certain period of time and/or when the response of the heart to the control sequence is reduced below a predetermined level.

In an alternative embodiment of the invention a control device includes a human operator in the loop, at least during a first stage where the controller must "learn" the distinctive aspects of a particular heart/patient. At a later stage, the operator may monitor the therapeutic effect of the controller on a periodic basis and change the programming of the controller if the therapeutic effect is not that which the operator desires.

In an additional embodiment of the invention, the controller is not implanted in the body. Preferably, the control sequence is applied using one or more catheters which are inserted into the vascular system. Alternatively, electrodes may be inserted directly through the chest wall to the heart.

In another preferred embodiment of the invention a controlling current (or electric field) is applied from electrodes eternal to the body. One inherent problem in external controlling is that the controlling current will usually electrify a large portion of the heart. It therefore important to delay the application of the current until the heart is refractory. One method of achieving this objective is to sense the ECG using external electrodes. Preferably, an electrode array is used so that a local activation time in predetermined portions of the heart may be determined.

Another method of external controlling combines controlling with external pacing, thereby simplifying the task of properly timing the controlling pulse relative to the pacing pulse. In a preferred embodiment of the invention, the delay between the pacing pulse and the controlling pulse is initially long and is reduced until an optimum delay is determined which gives a desired improvement in pumping and does not cause fibrillation.

Additionally or alternatively, the external pacemaker includes a defibrillator which applies a defibrillation pulse if the controlling pulse causes fibrillation.

It should be appreciated that pacemakers and controllers in accordance with various embodiments of the present invention share many common characteristics. It is anticipated that combining the functions of a controller and of a pacemaker in a single device will have many useful applications. However, several structural differences between pacemakers, defibrillators and controllers in accordance with many embodiments of the present invention are notable.

One structural difference relates to the size and shape of the electrodes. Pacemakers usually use bipolar activation electrodes or unipolar electrodes where the pacemaker case is the other electrode. The design of the electrodes is optimized to enhance the contact between the electrodes and the heart at a small area, so that the power drain in the pacemaker will be as low as possible. In a defibrillator, there is an opposite consideration, namely, the need to apply a very large amount of power to large areas of the heart without causing damage to the heart. In preferred embodiment of the present invention, small currents are applied, however, it is desirable that the current will flow through large portions of the cardiac tissue, in a controlled manner.

Another structural difference relates to the power supply. Pacemaker power supplies usually need to deliver a short (2 msec), low power, pulse once a second. Defibrillators usually need to deliver a short (6 8 msec), high power, pulse or series of pulses at long intervals (days). Thus, pacemakers, usually drain the power from a capacitor having a short delay and which is directly connected to the battery, while defibrillators usually charge up both a first and a second capacitor so that they may deliver two sequential high-power pulses. A controller in accordance with some embodiments of the present invention, is required to provide a long low power pulse once a second. Preferably, the pulse is longer than 20 msec, more preferably longer than 40 msec and still more preferably, longer than 70 msec. Such a pulse is preferably achieved using a slow-decay capacitor and/or draining the power directly from a battery, via an constant current, a constant voltage and/or a signal forming circuit. Preferably, the electrodes used in a controller in accordance with the present invention slowly release a steroid, to reduce inflammation at the electrodes point of contact with the heart.

Another structural difference relates to the placement of the electrodes. In a pacemaker a single electrode is placed in the apex of the heart (in some pacemakers, one electrode per chamber, or sometimes, more than one). In a defibrillator, the electrodes are usually placed so that most of the heart (or the right atrium in AF defibrillators) is between the electrodes. In a controller according to some embodiments of the present invention, the electrodes are placed across a segment of heart tissue, whose control is desired. Regarding sensing, many pacemakers utilize sensing in one chamber to determine a proper delay before electrifying a second chamber. For example, in a heart whose AV node is ablated, the left ventricle is synchronized to the right atrium by a pacemaker which senses an activation front in the right atrium and then, after a suitable delay, paces the left ventricle. It is not, however, a usual practice to sense the activation front in a chamber and then pace the selfsame chamber after a delay. Even when such same chamber sensing and pacing is performed, the sensing and pacing are performed in the right atrium and not the left ventricle. Further, sensing at the pacing electrode in order to determine a delay time for electrification of the electrode is a unique aspect of some aspects of the present invention, as is sensing midway between two pacing electrodes. Another unique aspect of some embodiments of the present invention is pacing in one chamber (the right atrium), sensing an effect of the pacing in another chamber (the left ventricle) and then pacing the other chamber (the left ventricle). The use of multiple pairs of electrodes disposed in an array is another unique aspect of certain embodiments of the present invention.

Due to the wide range of possible signal forms for a controller, a preferred controller is programmable, with the pulse form being externally downloadable from a programmer. Telemetry systems for one- and two-directional communication between an implanted pacemaker and an external programmer are well known in the art. It should be noted that various embodiments of the present invention can be practiced, albeit probably less efficiently, by downloading a pulse form in accordance with the present invention to a programmable pacemaker. In a preferred embodiment of the invention, such a programmer includes software for analyzing the performance and effect of the controller. Since analysis of the performance of the controller may include information not provided by the controller, such as an ultrasound image or an external body ECG, such software may be run from a separate computer.

It should be appreciated that a controller in accordance with the present invention is preferably personalized for particular patient before implantation therein. Alternatively or additionally, the personalizations may be performed by programming the device after it is implanted. The heart of the patient is preferably mapped, as described above, in order to determine the preferred placement of the control electrodes and/or the sensing electrodes and/or in order to determine the proper timings.

In one example, where the left ventricle is controlled, it is useful to determine the earliest activated area in the left ventricle, for implantation of the sensing electrode. In another example, the heart is mapped to determine viable tissue portions which are suitable for implantation of electrodes (such that current will flow between the two electrodes). In another example, the activation profile of the heart is determined so that it is possible to estimate propagation times between various portions of the heart, and in particular, the pacing source (natural or artificial) and the controlling electrodes. In another example, the propagation of the activation front in the heart is determined so that the proper orientation of the electrodes with respect to the front may be achieved and/or to properly locate the sensing electrode(s) with respect to the controlling electrodes. It is also useful to determine arrhythmias in the heart so as to plan anti-arrhythmic treatment in accordance with the present invention.

In another example, the amount of increase in contractility is determined by the amount of live tissue between the controlling electrodes. A viability map may be used to determine a segment of heart tissue having a desired mount of live tissue.

The timing of the activation of cardiac muscle relative to the rest of the heart is an important factor in determining its contribution to the cardiac output. Thus, it is useful to determine the relative activation time of the segment of the heart which is to be controlled, prior to implanting the electrodes.

Figure 5:
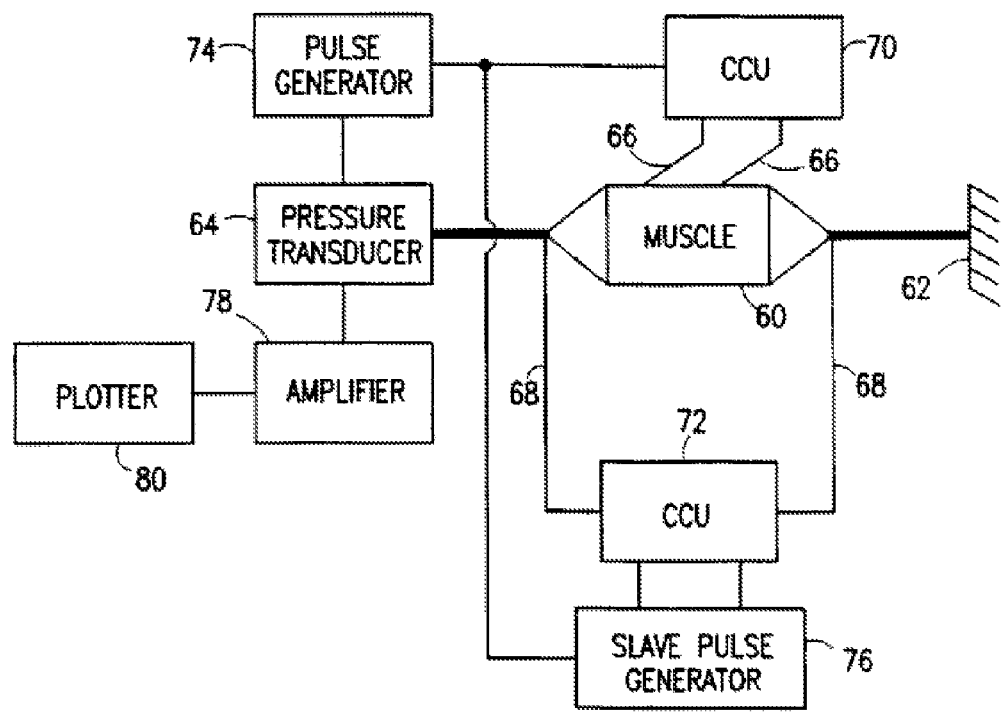
FIG. 5 is a schematic diagram of an experimental setup used for testing the feasibility of some embodiments of the present invention, in accordance with an embodiment of the present invention.

FIG. 5 shows an experimental setup designed and used to test some embodiments of the present invention, in accordance with an embodiment of the present invention. A papillary muscle 60, from a mammalian species (in the first set of experiment, a guinea pig), was connected between a support 62 and a pressure transducer 64 in a manner such that isometric contraction could be achieved. Muscle 60 was stimulated by a pair of electrodes 66 which were connected to a pulsed constant current source 70. A pulse generator 74 generated constant current pacing pulses for electrodes 66. A pair of electrodes 68 were used to apply an electric field to muscle 60. A slave pulse generator 76, which bases its timing on pulse generator 74, electrified electrodes 68 via a pulsed constant current source 72. The force applied by the muscle was measured by transducer 64, amplified by an amplifier 78 and drawn on a plotter 80. Pulse generator 74 selectably generated short activation pulses 500, 750, 1000 and 1500 msec (t1) apart for variable activation of muscle 60, i.e., 2, 1.33, 1 and 0.66 Hz. Pulse generator 76 generated a square wave pulse which started t2 seconds after the activation pulse, was t3 seconds long and had a selected current (in mA) higher than zero (in amplitude).

Figure 6A:
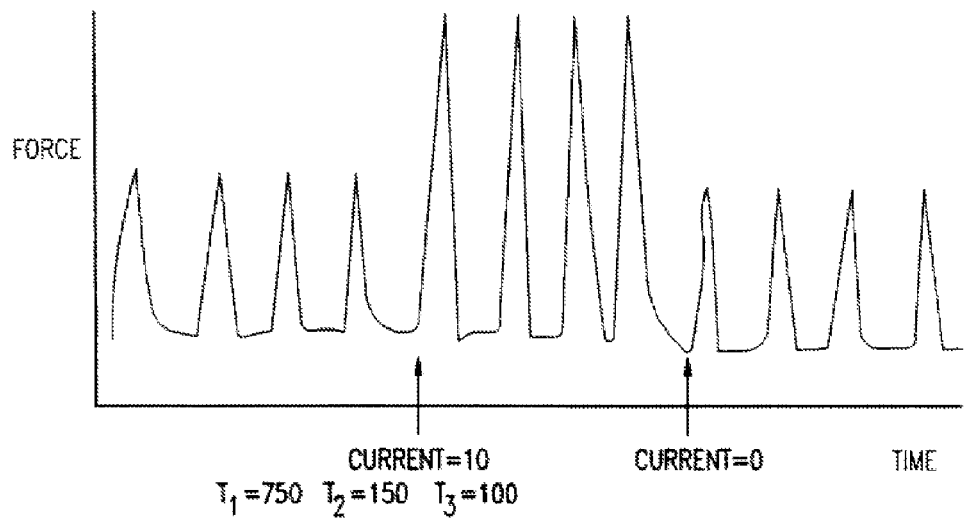
Figure 6B:
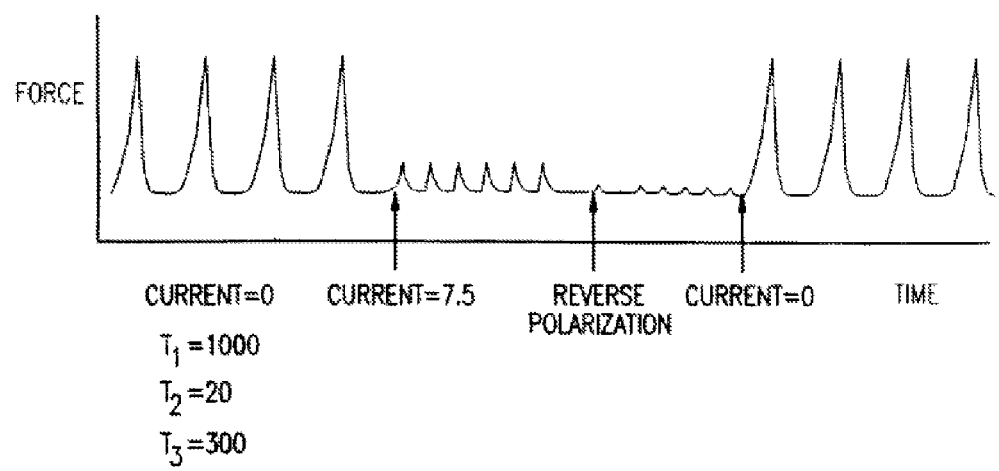

FIGS. 6A-6C are graphs showing some results of respective experiments of the present invention. In general, the results shown are graphs of the force of the muscle contractions after muscle 60 reaches a steady state of pulsed contractions. FIG. 6A is a graph of the results under the following conditions:

t1 (pacemaker pulse)=750 msec;
t2 (delay)=150 msec;
t3 (pulse duration)=100 msec; and
current=10 mA.

As can be seen, the force exerted by the muscle was increased by a factor of 2.5 when the controlling pulse (electrodes 68) was used as opposed to when electrodes 68 were not activated.

FIG. 6B is a graph of the force of muscle contractions under the following conditions:

t1=1000 msec;
t2=20 msec;
t3=300 msec; and
current=7.5 mA.

As can be seen, the amplitude of the contractions is extremely attenuated. When the polarity of the controlling signal was inverted, after a few contractions, the contractions of muscle 60 were almost completely attenuated.

FIG. 6C is a graph of the force of muscle contractions under the following conditions:

t1=1000 msec;
t2=20 msec;
t3=300 msec; and
current=1 mA.

In this case, the effects of increasing the contractile force of muscle 60 remained for about two minutes after the electrification of electrodes 68 was stopped. Thus, the contraction of muscle 60 is dependent not only on the instantaneous stimulation and control but also on prior stimulation and control.

Using a similar experimental setup, additional experiments were performed, some on papillary muscles and some on cardiac septum muscles from the ventricles and atria walls. In these experiments, the test animal was usually a rabbit, however, in one case a rat was used. Most of these experiments used a DC constant current source which was in contact with the muscle, however, an electrical field scheme was also tested, and yielded similar results. In the electric field scheme, the electrodes were placed in a solution surrounding the muscle segment and were not in contact with the muscle segment. The current used was 2-10 mA. In a few experiments, no increase in contractile force was induced, however, this may be the result of problems with the electrodes (interaction with ionic fluids) and/or the current source, especially since Ag—AgCl electrodes, which tend to polarize, were used in these experiments. In general, many cycles of increases in contractility and return to a base line were performed in each experiment. In addition, the increases in contractility were repeatable in subsequent experiments. These increases were obtained over a pacing range of 0.5 Hz to 3 Hz.

Figure 7A:
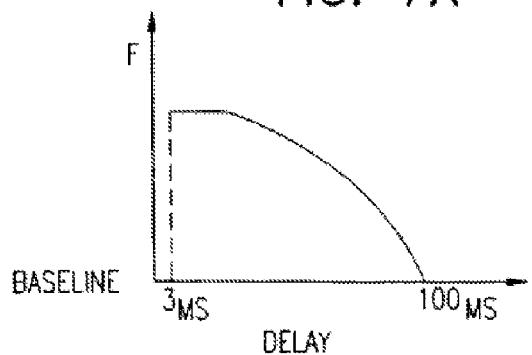
FIG. 7A is a graph summarizing results of experimentation on an isolated segment of cardiac muscle fibers, and showing the effect of a delay in applying a pulse in accordance with an embodiment of the invention, on the increase in contractile force, in accordance with an embodiment of the present invention.
Figure 7B:
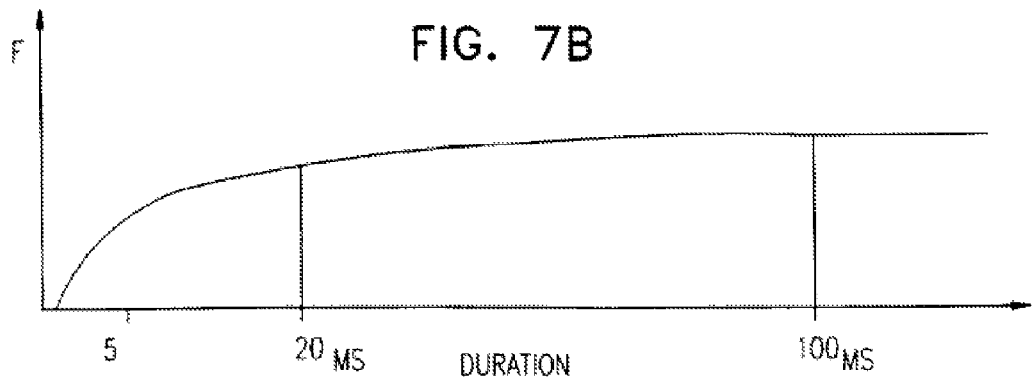
FIG. 7B is a graph summarizing results of experimentation on an isolated segment of cardiac muscle fibers, and showing the effect of a duration of the pulse on the increase in contractile force, in accordance with an embodiment of the present invention.
Figure 7C:
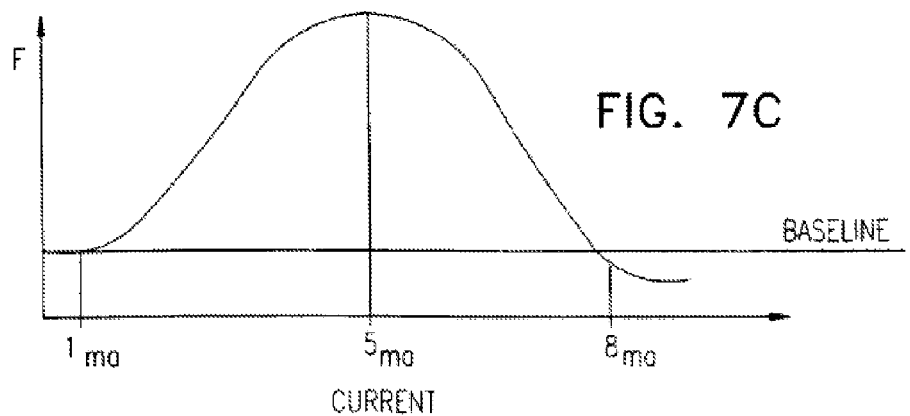
FIG. 7C is a graph summarizing results of experimentation on an isolated segment of cardiac muscle fibers, and showing the effect of a current intensity of the pulse on the increase in contractile force, in accordance with an embodiment of the present invention.

FIGS. 7A-7C summarize the results obtained in these further experiments, in accordance with respective embodiments of the present invention. It should be appreciated, that the time scales of the applied pulse are strongly associated with the pacing rate and with the animal species on which the experiment was performed. In these experiments, the pacing rate was usually about 1 Hz. Within the range of 0.5 Hz to 3 Hz the pulse form required for an increase in contraction force is not substantially affected by the pacing rate. The intensities of the currents used in the experiments are affected by the electrode types used, and possibly by the animal species, so that if other electrode types are used, different current intensities may be required for the same effect. Ten experiments were performed on a left papillary muscle, of which 8 showed an increase in contractility due to an applied non-excitatory current. Four experiments were performed on a right papillary muscle, of which three showed an increase in contractility. Two experiment were performed on left ventricular muscle, both showed an increase in contractility. On the average, an increase in contractile force of .about.75% was obtained. The range of increases was between 43% and 228% depending on the exact experimental configuration.

FIG. 7A shows the effect of a delay in the onset of the applied current on the increase in contractile force. A small delay does not substantially affect the increase in contractile force. It should be noted that as the delay increases in duration, the increase in contractility is reduced. It is theorized that such a pulse, applied at any delay, affects the plateau and/or the refractory period. However, the increase in contractility is only possible for a window of time which is more limited than the entire activation cycle of a muscle fiber.

Changing the polarity of the applied current sometimes affected the contractility. Usually, a first polarity generated an greater increase in contractile force, while the other polarity generated a lower increase than the first polarity. In some experiments, reversing the polarity during an experiment decreased the contractile force, for a short while or for the entire duration of the pulse, to a level lower than without any applied current. One possible explanation is that papillary muscle has a preferred conduction direction (which may not be as pronounced in ventricular tissue). Another explanation is artifacts relating to the ionization of the electrodes used in the experiments.

FIG. 7B shows the effect of pulse duration on the increase in contractile force of a papillary muscle. A very short pulse, on the order of 1 msec, does not substantially affect the contractile force. In a pulse between about 1 msec and 20 msec the contractility increases with the duration. In a pulse of over 20 msec, the increase in contractile force as a function of pulse duration is reduced; and in a pulse with over about 100 msec duration there is no apparent further increase in the contractile force of an isolated papillary muscle.

FIG. 7C shows the effect of the current intensity on the increase in contractile force. It should be noted that above about 8 mA the contractile force actually decreases below the baseline condition (where no current was applied). It may be that this effect is related to the above described theory of intra-cellular calcium stores, and that too much calcium in the cardiac muscle cell reduces the availability of these stores, and therefore, the cell's contractility.

In addition to the above summarized results, several experimental results deserve special notice.

Figure 8A:
FIG. 8A is a graph showing the effect of a controlling current on a heart rate, in accordance with a preferred embodiment of the invention.

In one experiment, shown in FIG. 8A, a segment of a right atrium from a rabbit was allowed to set its own, intrinsic, pace (about 2 Hz to 3 Hz). A non-excitatory current which was a constant current of 2 mA was driven through the tissue, constantly, as shown. As a result, the self pacing rate of the segment increased, as did the contractility (after a first, short, reduction in force).

In a second, multi-step experiment, a right rabbit papillary muscle was paced at 1.5 Hz. The applied current was constant at between 2 mA and 4 mA (depending on the experimental step), in a pulse 70 msec long and no delay after the pacemaker pulse. The contractility increased by between 45% and 133% (depending on the step). The increased contractility was sustained at 3 mA for as long as two hours. Stopping the applied field caused a rapid return to the original (uncontrolled) contractile force. Re-application of the field repeated the previous results.

In a third experiment, increasing the pulse duration of a 2 mA current over the range of 10 msec to 100 msec in a left rabbit papillary muscle increased the contractile force; however, no effect on the duration of the muscle twitch was observed.

FIG. 8B is a series of graphs which shows an increase in contractility in several different cardiac muscle types (the horizontal bar indicates the application of a controlling electric field), in accordance with an embodiment of the present invention.

Two more experiments, not included in the above discussion, were performed on a papillary muscle. In these experiments, a triangular shaped pulse, having a duration of 120 msec and a peak of 5 mA, was applied with no delay after a standard pacing pulse (2 mA, 2 msec). The increase in contractility of the muscle was about 1700%, from 10 mg to 178 mg. The duration of the contraction increased from 220 msec to 260 msec.

In another series of experiments, a whole living heart was removed from a rabbit (1-2 Kg in weight) and controlled using methods as described hereinabove. The apparatus for keeping the heart alive was an Isolated Heart, size 5, type 833, manufactured by Hugo Sachs Elektronik, Gruenstrasse 1, D-79232, March-Hugstetten, Germany. In these experiments, only the left ventricle is functional. The Pulmonary veins are connected to a supply hose, in which supply hose there is a warm (about 37 degrees C.) isotonic, pH balanced and oxygenated solution. The solution is pumped by the heart into the aorta. The heart itself is supplied with oxygen from the aorta, through the coronary arteries. The coronary veins empty into the right ventricle, from which the solution drips out. The solution which drips out (coronary blood flow) can be measured by collecting it in a measuring cup. Both the preload and the afterload of the vascular system can be simulated and preset to any desirable value. In addition, the afterload and preload can be measured using this apparatus.

The heart was connected to an ECG monitor, a pacemaker and a programmable pulse generator. The electrodes for applied the field typically had an area of between 2 cm.sup.2 and 3 cm.sup.2. The left ventricular pressure (LVP) was measured using a pressure probe inserted into the ventricle. The flow through the aorta was measured using an electromagnetic flowmeter. Various parameters, such as pH, pO.sub.2, pCO.sub.2 and temperature may be measured by attaching additional measurement devices. All the measurement devices may be connected to a computer which collects, and preferably analyzes the results.

A most notable experimental result was an increase in flow from the heart as a result of electrical control. Another notable result was an increase in afterload as a result of the control. Still another notable result was an increase in the developed left ventricular pressure in the heart, when electrical control was applied.

A summary of 26 experiments using an isolated heart is as follows, in 20 experiments an increase in cardiac output was observed, while in six experiments, no increase in cardiac output was observed. Possible reasons for the failure to increase cardiac output include, biological damage to the heart while it was being extracted from the animal. In some cases, this damage is clear from the reduced cardiac output in one isolated heart as compared to a second, otherwise similar, rabbit heart. Other reasons include, incorrect placement of electrodes (over the right ventricle instead of over the left ventricle), encrustation of the electrodes with proteins and technical problems with the equipment which delivers the controlling electric field. In 11 experiments where the left ventricle was paced, the average increase in cardiac output was 17% with a standard deviation of 11%. In eight experiments where the right atrium was paced, the average increase was 9.+−0.4%. In nine experiments, where the heart was not paced and a controlling field was applied based on a sensing of local activation times, the increase was 7.+−0.2%. It should be noted that the number of experiments is over 26, since in some experiments two different pacing paradigms were tried.

Figure 9:
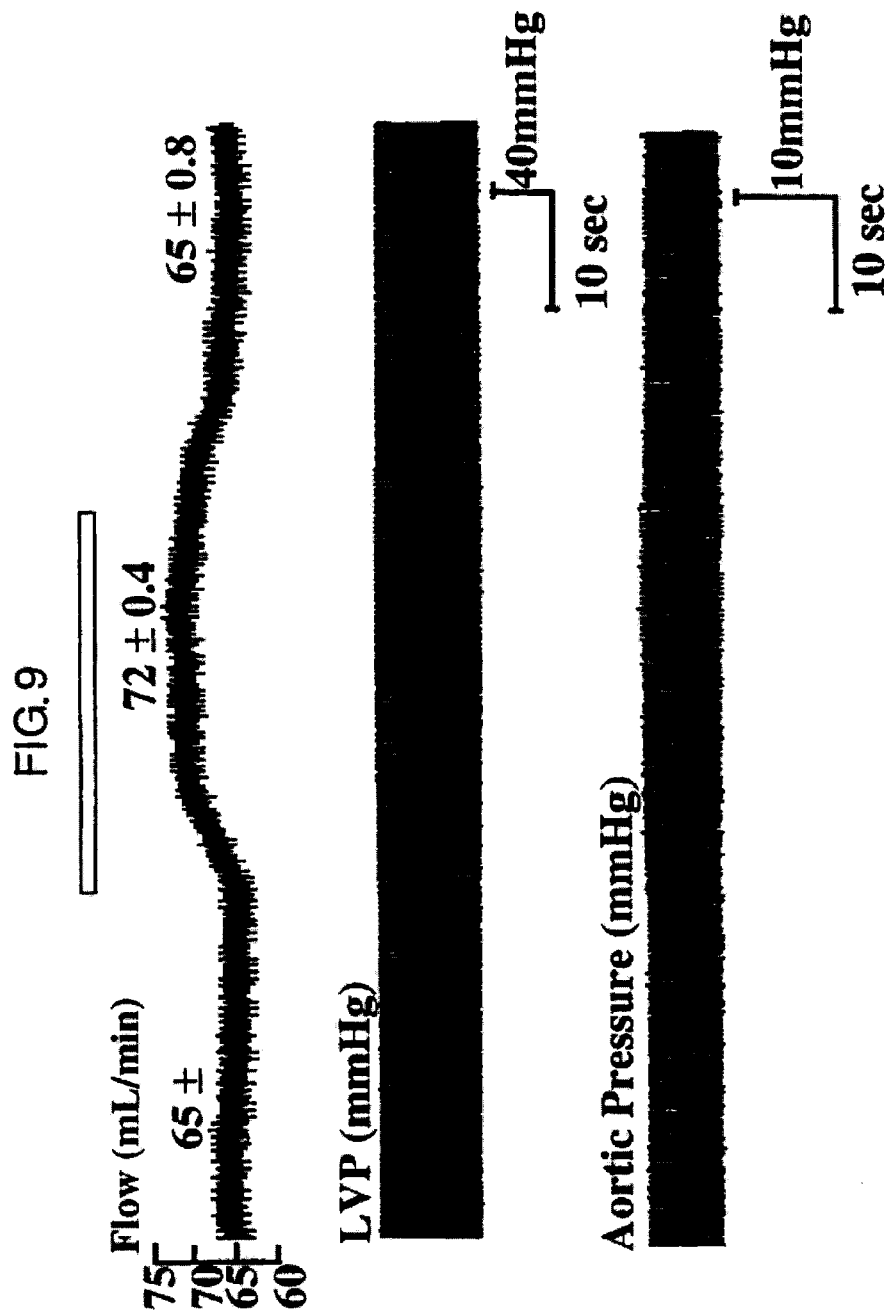

FIG. 9 is a series of graphs showing the results of an experiment in which a 10 mA constant current pulse, having a duration of 20 msec and delayed 5 msec after the pacing of the heart, was applied, in accordance with an embodiment of the present invention. Two wire electrodes were used to apply this pulse, one electrode was placed at the apex of the heart overlaying the left ventricle and one electrode was placed at the base of the left ventricle. The pacing was performed using a bipolar electrode, also placed near the apex of the heart on the left ventricle. The pacing rate was approximately 10% higher than the normal pace. The pacing pulse was 2 msec long, 2 mA in amplitude and was applied at a frequency of 3.5 Hz. The application of the constant current pulse is indicated in the Figure (and in the following ones) by a bar (filled or unfilled).

In this experiment, an increase in the afterload (the actual pressure developing in the Aorta) of about 5% and an increase in LVP (Left ventricle pressure) of about 3% were observed. The increase in LVP was only in the end systole pressure, not in the end diastole pressure. An increase in flow of about 11% is clearly shown in FIG. 9. The increase in flow is very important since one of the main problems with patients with congestive heart failure is a low cardiac flow.

Figure 10:
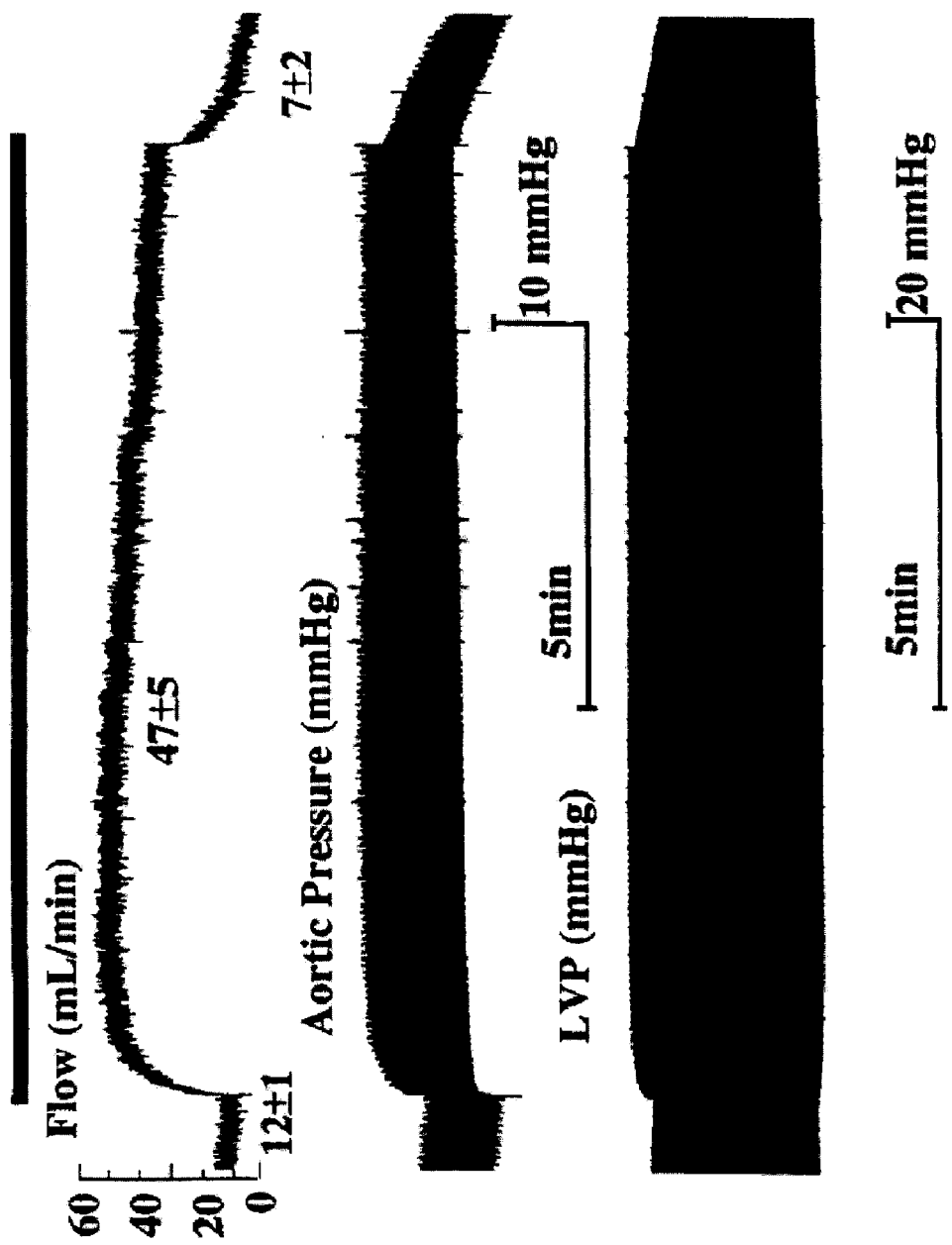

FIG. 10 is a series of graphs showing the results of an experiment in which a 5 mA constant current pulse, having a duration of 80 msec and delayed 2 msec after the pacing of the heart was applied, in accordance with an embodiment of the present invention. The wiring and pacing in this experiment were similar to the experiment described with reference to FIG. 9, except that carbon electrodes were used for applying the constant current pulse.

In this experiment, a noticeable increase in afterload can be determined from the graph. An increase in LVP (Left ventricle pressure) of about 6% can also be observed. It should be noted that the increase in afterload is observed for both the diastolic pressure and the systolic pressure, while inside the left ventricle, the pressure increase is mainly in the systole. In fact, there is a slight reduction in diastolic pressure, which may indicate an increase in contractility and/or an improvement in diastolic wall motion. An increase in flow of several hundred percent is clearly shown in FIG. 10. It should be noted that a healthy heart may be expected to have a flow of about 100 ml/min. The low initial flow (12 ml/min.) is probably a result of damage to the heart, such as ischemia.

Figure 11:
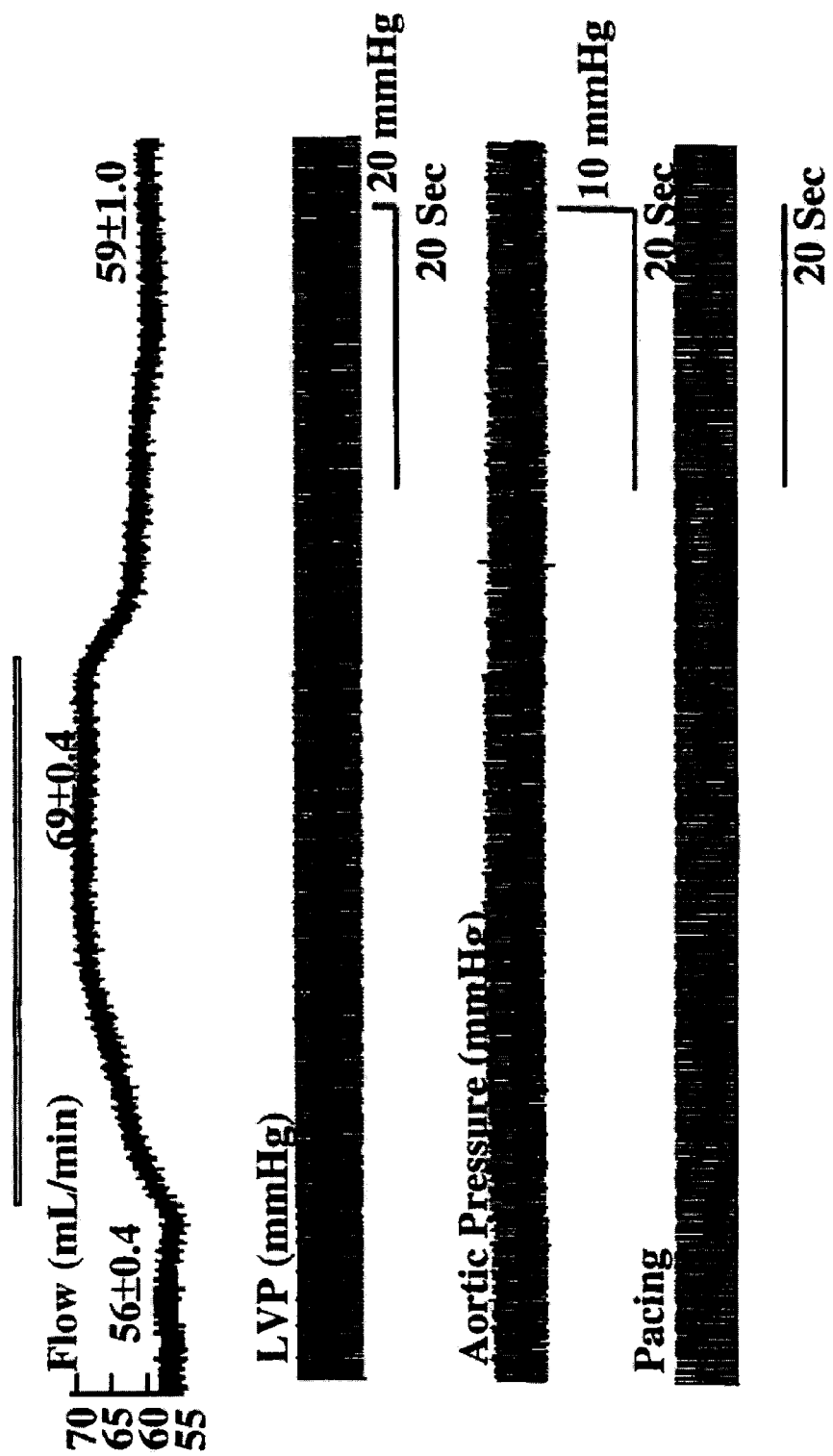

FIG. 11 is a series of graphs showing the results of an experiment in which a 5 mA constant current pulse, having a duration of 20 msec and delayed 2 msec after the local activation time at the ventricle was used, in accordance with an embodiment of the present invention. The pacing and wiring in this experiment were similar to the experiment described with reference to FIG. 9. A sensing electrode was placed on the left ventricle halfway between the two controlling electrodes and the delay was measured relative to the local activation time at the sensing electrode. The sensing electrode comprised two side by side "J" shaped iridium-platinum electrodes. A pacing pulse was applied using an additional Ag—AgCl electrode at the apex of the heart. In this experiment, the sensing electrode is shut off for 200 msec after the local activation is sensed, so that the controlling pulse is not erroneously detected by the sensing electrode as a local activation.

In this experiment, an increase in the afterload and an increase in LVP were observed. The increase LVP was only evident in the end systole pressure, not in the end diastole pressure. An increase in flow of about 23% is clearly shown in FIG. 11.

Figure 12:
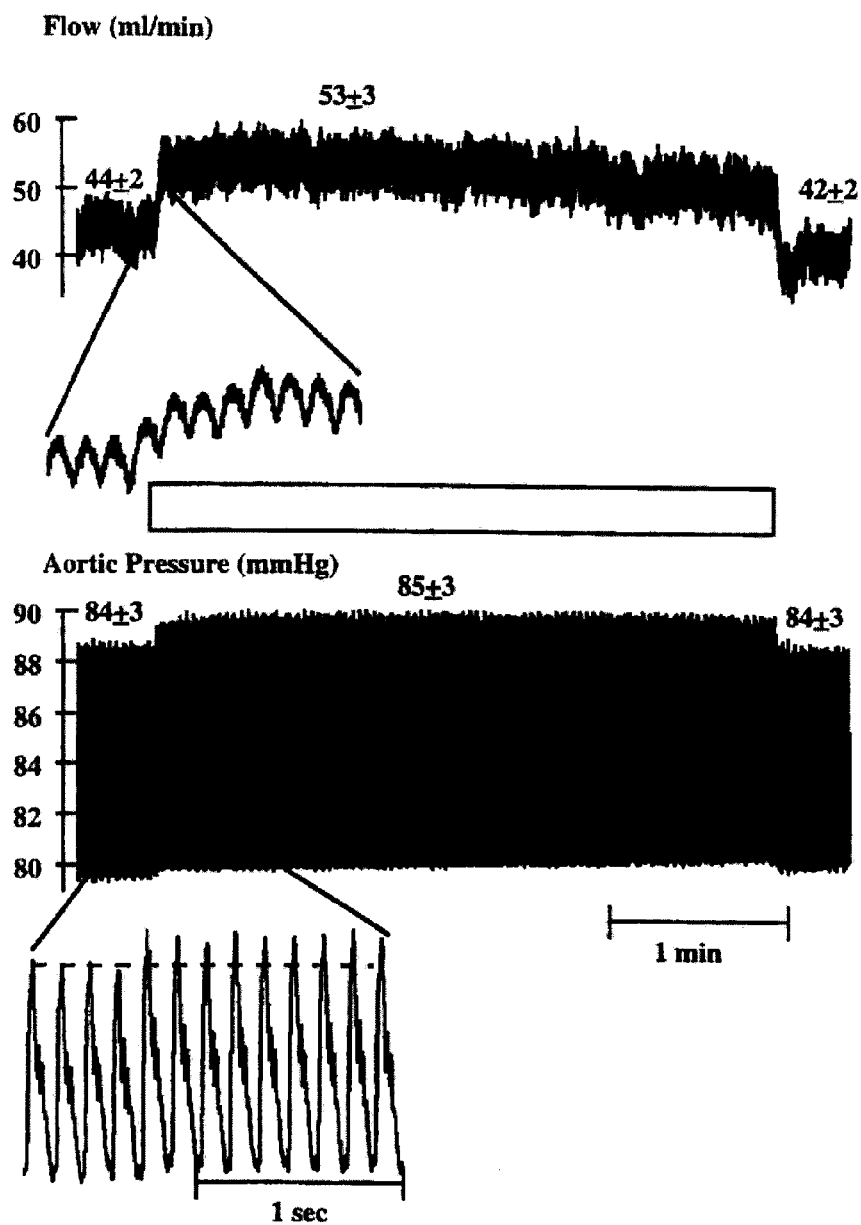

FIG. 12 is a series of graphs showing experimental results from another experiment, showing an significant increase in aortic flow and in aortic pressure, in accordance with an embodiment of the present invention. The pulse parameters were 5 mA, 70 msec duration and a 5 msec delay. Pacing and wiring are as in the experiment of FIG. 9.

Figure 13:
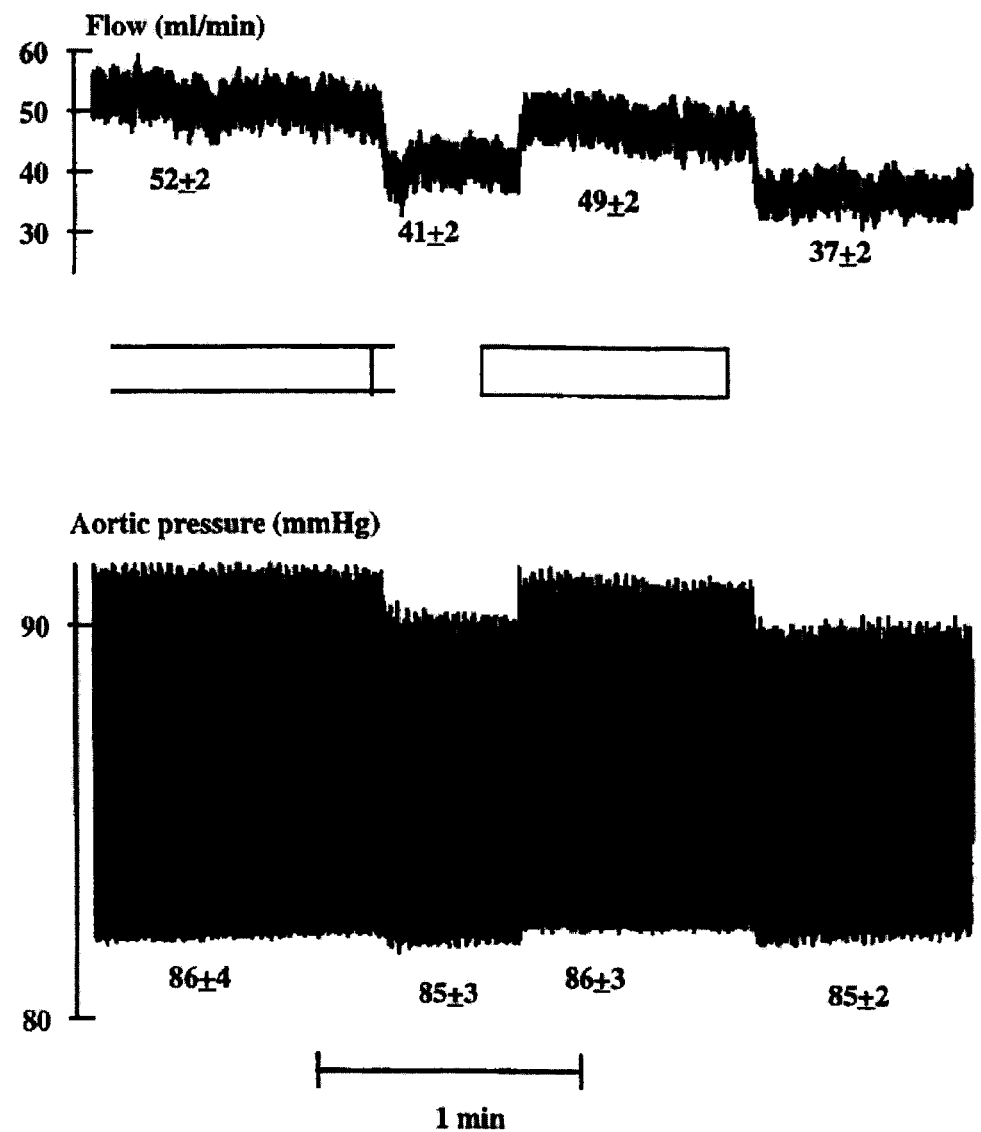

FIG. 13 is a series of graphs showing experimental results from repeating the experiment of FIG. 12, showing that the increase in aortic flow is controlled by the electrification of the electrodes, in accordance with an embodiment of the present invention. Thus, when the electrification is stopped, the flow returns to a baseline value; when the electrification is restarted the flow increases again and when the electrification is stopped again, the flow returns to the baseline value.

Figure 14:
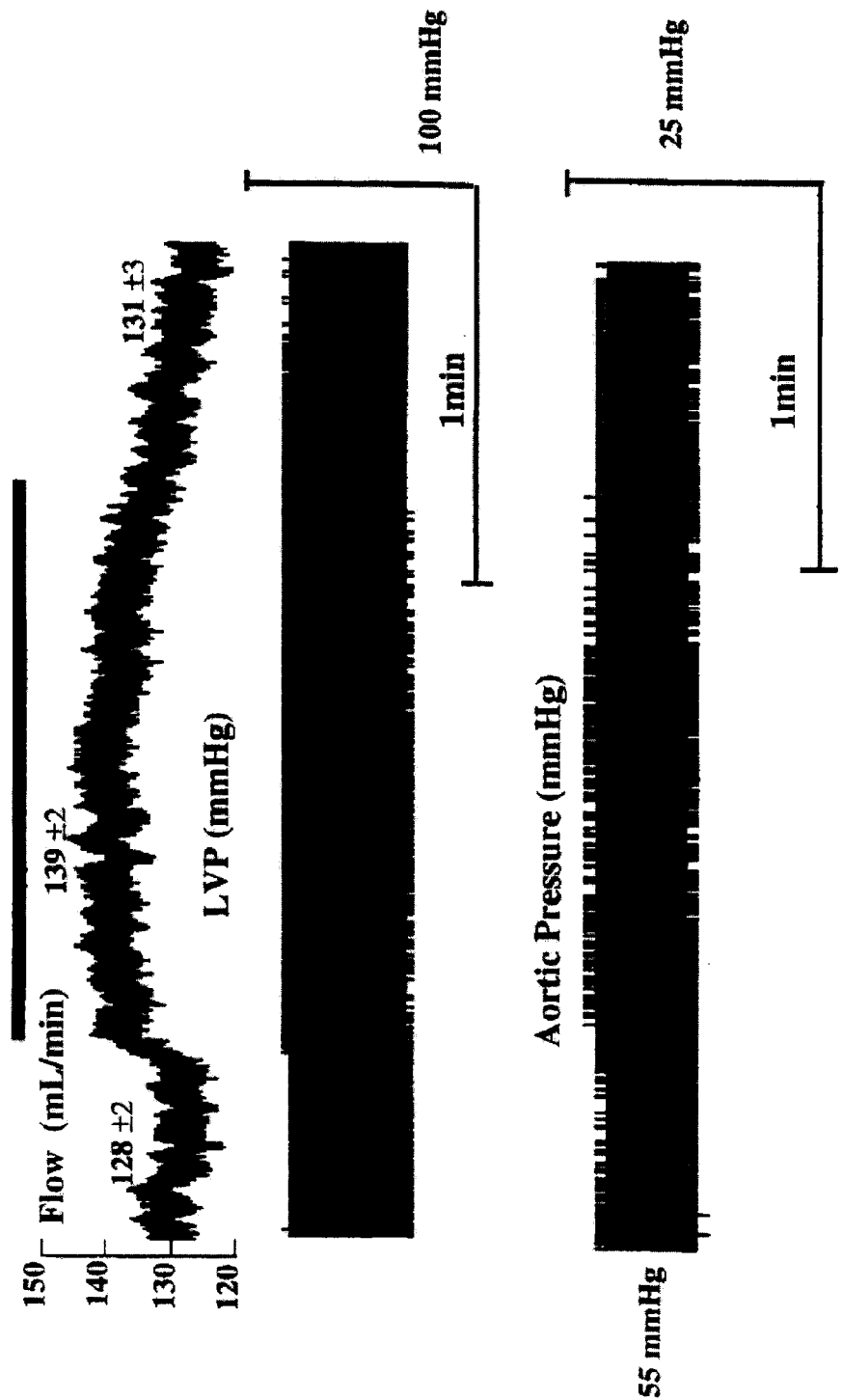

FIG. 14 is a series of graphs showing experimental results from another experiment, in which the right atrium was paced at 3 Hz, rather than the left ventricle being paced at 3.5 Hz, as in previously described experiments, in accordance with an embodiment of the present invention. Pacing and wiring are similar to those in the experiment of FIG. 11, except that the pacing electrodes are in the right atrium and the action potential is conducted from the right atrium to the left ventricle using the conduction pathways of the heart. The pulse parameters are 5 mA for 20 msec, with no delay after sensing a local action potential. The sensing electrode is shut off for 100 msec after it senses the local action potential, to reduce the possibility of identifying the controlling pulse as a local activation potential. In this experiment, an increase in flow of 9% was observed.

FIG. 15 is a series of graphs showing experimental results from another experiment, similar to the experiment of FIG. 14, except that instead of using two controlling electrodes, four controlling electrodes were used, in accordance with an embodiment of the present invention. The controlling electrodes were arranged in a square, with the sensing electrode at the center of the square. One pair of controlling electrodes comprised an electrode at the apex of the left ventricle and an electrode at the base. The other two electrodes were located in the halfway between the base and the apex of the left ventricle and near the right ventricle (at either side of the left ventricle). The applied pulse was 10 mA for 20 msec at a delay of 2 msec. Both pairs of electrodes are electrified simultaneously.

In this experiment, an increase in the afterload and an increase in end-systolic LVP were observed. In addition, a decrease in end-diastolic LVP was observed. An increase in flow of about 7% is also shown in FIG. 15.

FIG. 16 is a series of graphs showing experimental results from another experiment, similar to the experiment of FIG. 14, except that no sensing electrode is used, in accordance with an embodiment of the present invention. Rather, an activation signal propagation time is estimated for calculation of the desired delay between pacing the right atrium and controlling the left atrium. The activation propagation time is estimated by measuring the time between the pacing signal and the contraction of the left ventricle. The delay time is 5 msec more than the calculated average propagation time and was about 140 msec. In this experiment, an increase in the afterload and an increase in LVP were observed. An increase in flow of about 14% is also shown in FIG. 16.

FIG. 17 is a series of graphs showing experimental results from another experiment, similar to the experiment of FIG. 14, except that no pacing electrodes are used, in accordance with an embodiment of the present invention. Rather, the isolated heart is allowed to pace at its own rhythm. The pulse parameters are a 20 msec long pulse of 10 mA applied to both pairs of electrodes simultaneously, at a delay of 2 msec after the sensing electrode senses a local activation potential.

In this experiment, an increase in the afterload and an increase in LVP were observed. An increase in flow of about 7% is also shown in FIG. 17. It should be noted that the baseline output of the heart was about 110 ml/min., which indicates an output of a healthy heart.

Figure 18A:
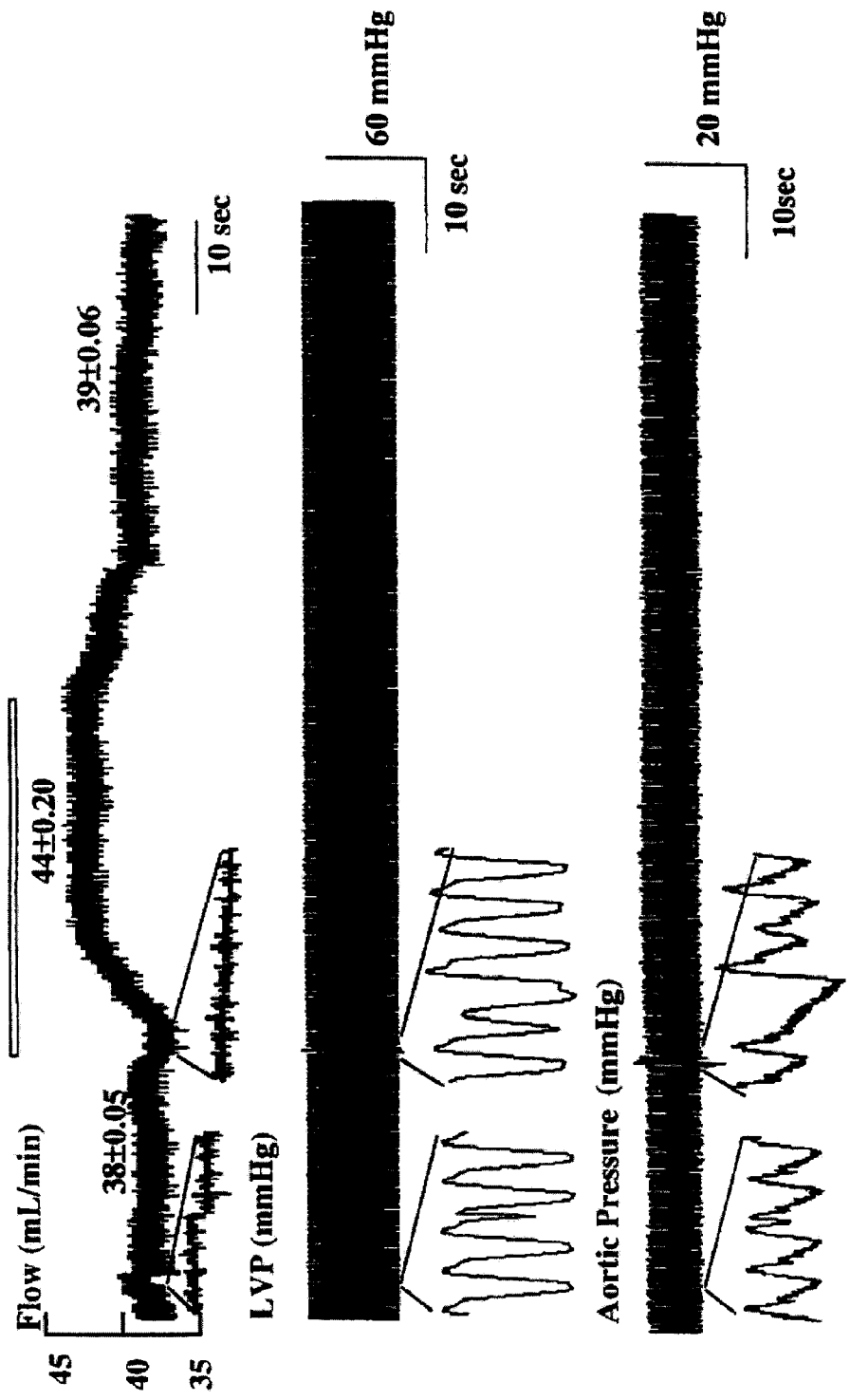

FIG. 18A is a series of graphs showing experimental results from another experiment in which the heart was made ischemic, in accordance with an embodiment of the present invention. The wiring is similar to that of FIG. 17, except that only one pair of controlling electrodes was used, one at the apex and one at the base of the left ventricle. The ischemia was designed to simulate a heart attack by stopping the flow of oxygenated solution to the coronary arteries for about ten minutes. After the flow of oxygenated solution was restarted a reduction in the cardiac output from 100 ml/min. to 38 ml/min. was observed. In addition, various arrhythmias in the activation of the heart were observed as a result of the ischemic incident. Controlling the heart, using a 20 msec pulse of 5 mA delayed 2 msec after the pacing, increased the flow by 16%. The sensing was blocked for between 100 and 200 msec after the sensing of a local activation. It should be noted that the controlling sequence worked even though the heart was arrhythmic.

One interesting result of the isolated heart experiments relates to pulse forms which do not induce fibrillation in the heart. It was determined that the pulse should not extend more than about half the duration of the left ventricle pressure wave (in this experimental setup, the pressure wave is measured, not electrical activity). In addition, a small delay (.about.5 msec) between the pacing and the pulse also appears to protect against fibrillation when the left ventricle is paced.

Figure 18B:
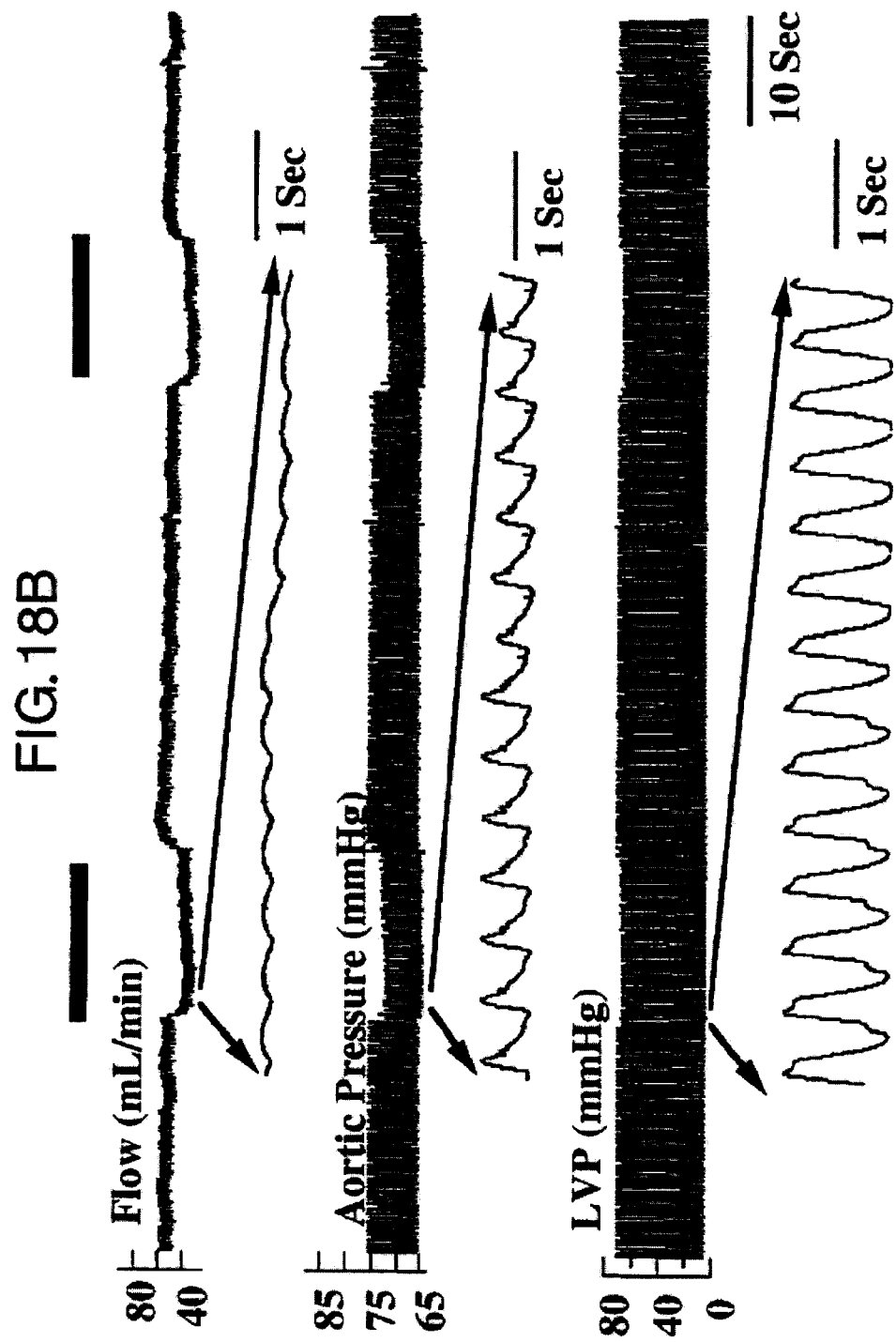

FIG. 18B is a series of graphs showing experimental results from another experiment in which the output of the heart was reduced, in accordance with an embodiment of the present invention. The heart was paced at the right atrium, using a pacing scheme similar to that of the experiment of FIG. 14. A controlling current was applied to the left ventricle using carbon electrodes. The controlling current was a 20 msec pulse of 5 mA amplitude applied at a delay of 30 msec after the pacing at the right atrium. Flow, LVP and Aortic pressure were all noticeably reduced as a result of this pulse.

Reducing the cardiac output is desirable in several circumstances, one of which is the disease "Hyperthropic Cardiomyopathy (HOCM)." This controlling scheme reduces the output of the left ventricle and the resistance against which the left ventricle is working, both of which are desirable for the above disease. It is hypothesized that the early controlling pulse (it is applied before the activation front from the right atrium reaches the left ventricle) works by extending the refractory periods of some of the cells in the left ventricle, thereby reducing the number of cells which take part in the systole and reducing the cardiac output. Presumably, different cells are affected each cardiac cycle. Alternatively, it may be that the precise delay determines which cells are affected. It is known to shorten the AV interval in order to improve the conditions of patients with HOCM. However, in the art, the entire ventricle is paced, albeit earlier. In the embodiment of the invention just described, the early applied electric field does not cause an early contraction of the ventricle, and does not effectively shorten the AV interval, as done in the art.

Figure 19:
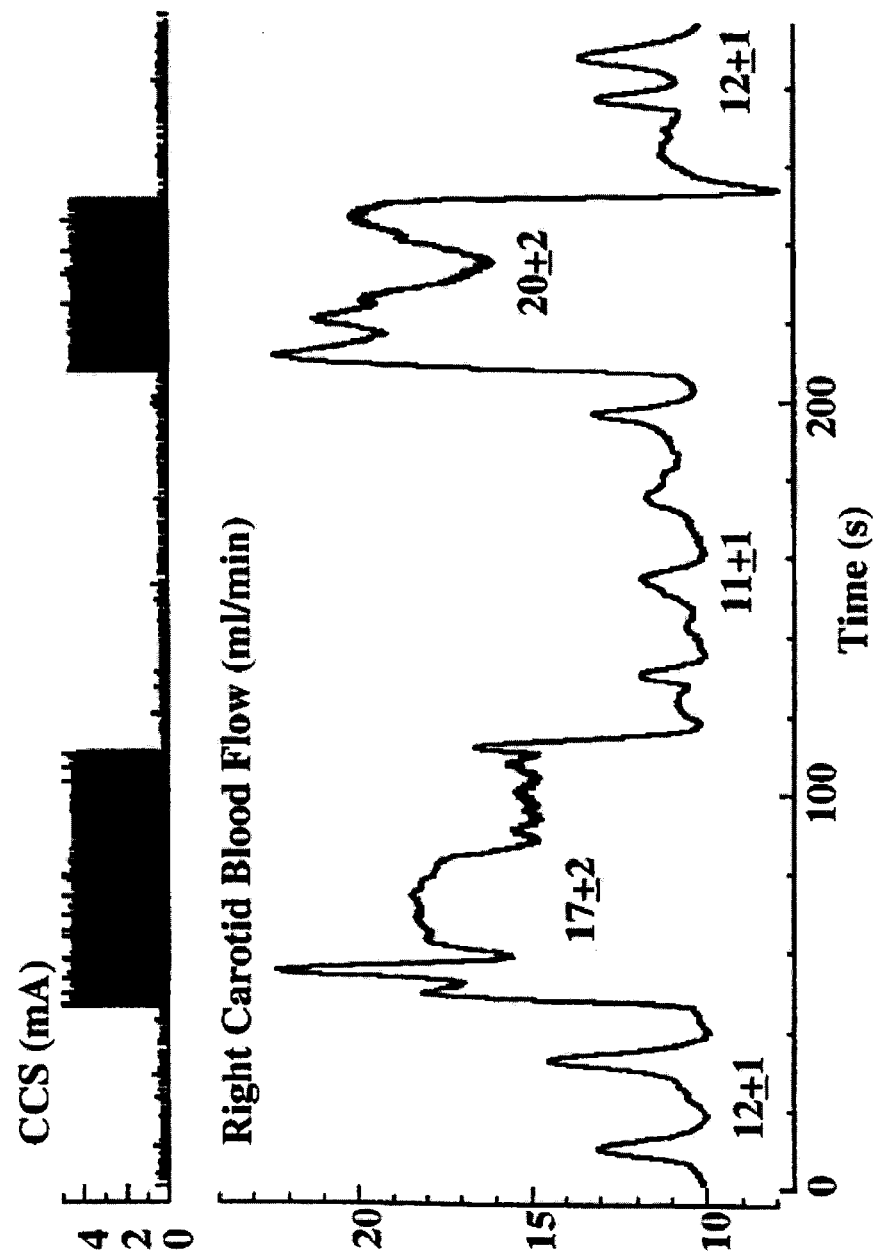
FIGS. 19-23 are each a series of graphs showing experimental results from experiments in which an in-vivo rabbit heart was controlled in accordance with an embodiment of the present invention.
Figure 20:
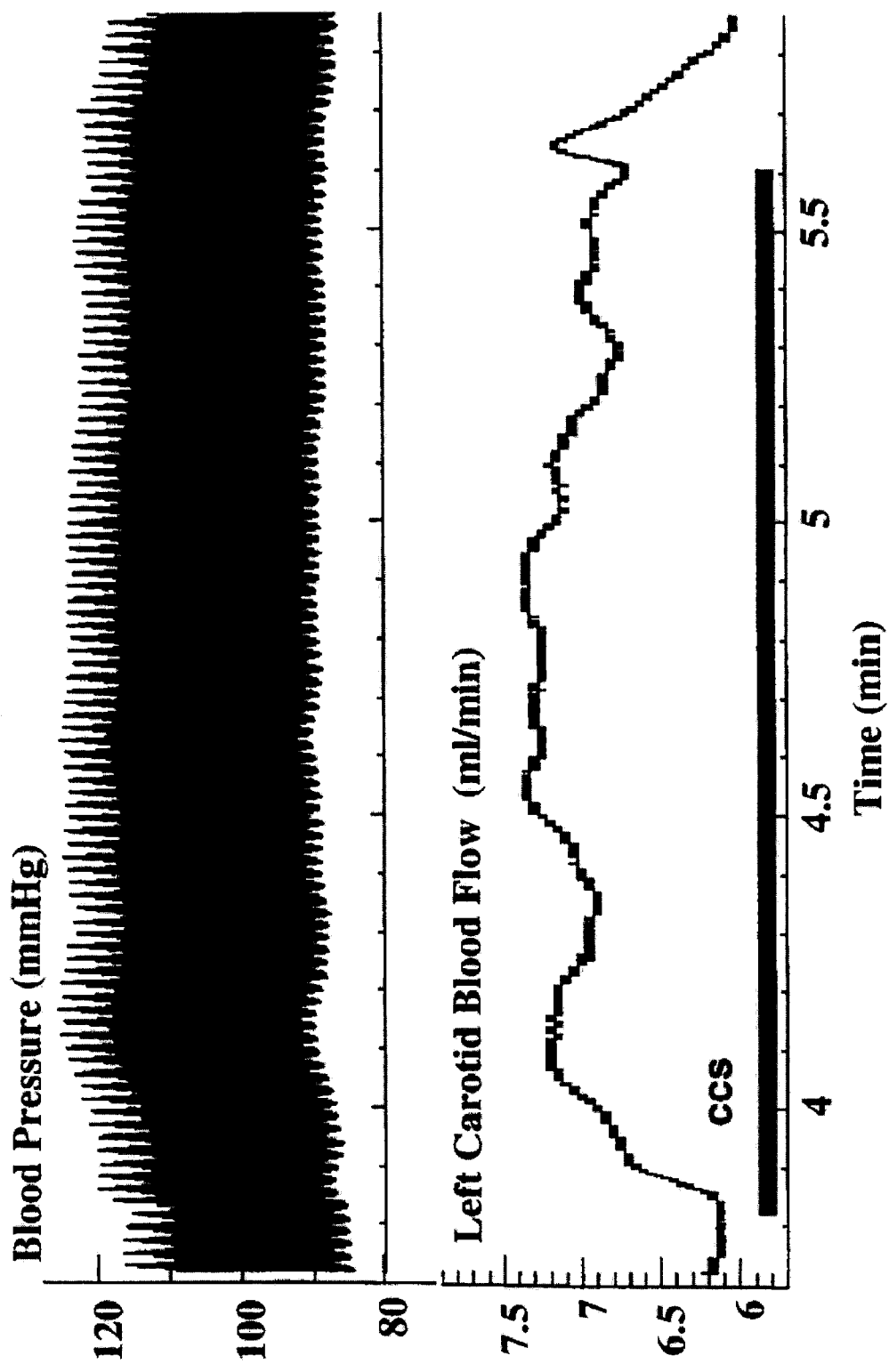

FIGS. 19 and 20 show the results of experiments performed on live animals on an in-vivo heart, in accordance with respective embodiments of the present invention. In the experiment whose results are shown in FIG. 19, a live 2.5 Kg rabbit was anesthetized using a venous access in its pelvic region with its chest opened to expose the heart. The pericardium of the heart was removed to provide direct contact between the heart and electrodes. The heart was paced via the left ventricle using a pair of titanium electrodes and the controlling current was applied using a pair of carbon electrodes. As in previous experiments, the pacing was applied at the apex of the left ventricle and the controlling electrodes were applied one at the base and one at the apex of the left ventricle. The rabbit was artificially respirated and liquids were supplied through the venous access. A blood-pressure catheter was inserted into the left femoral artery to measure the arterial blood pressure. The right carotid artery was exposed and a magnetic flowmeter was placed thereon to measure the flow in the carotid artery. The flow in a carotid artery was measured rather than the flow in the aorta for reasons of convenience. However, it should be noted that the carotid arteries have a feedback mechanism by which they attempt to maintain a constant blood supply to the brain by contracting the artery if the flow is too high.

The controlling signal was a 40 msec pulse having a amplitude of 4 mA and applied 5 msec after the pacing signal. The pacing signal was a 2 msec, 2 mA pulse at 5 Hz. An increase in flow in the right carotid artery of between 54 and 72% was observed during the application of the controlling signal.

The experiment whose results are shown in FIG. 20 had a similar design to the experiment of FIG. 19, except that the flow was measured using an ultrasonic flowmeter. The controlling current was a 20 msec pulse having an amplitude of 2 mA and delayed 5 msec from the pacing signal (which was the same as in the experiment of FIG. 19). Both an increase in flow and in blood pressure were observed in this experiment.

Figure 21:
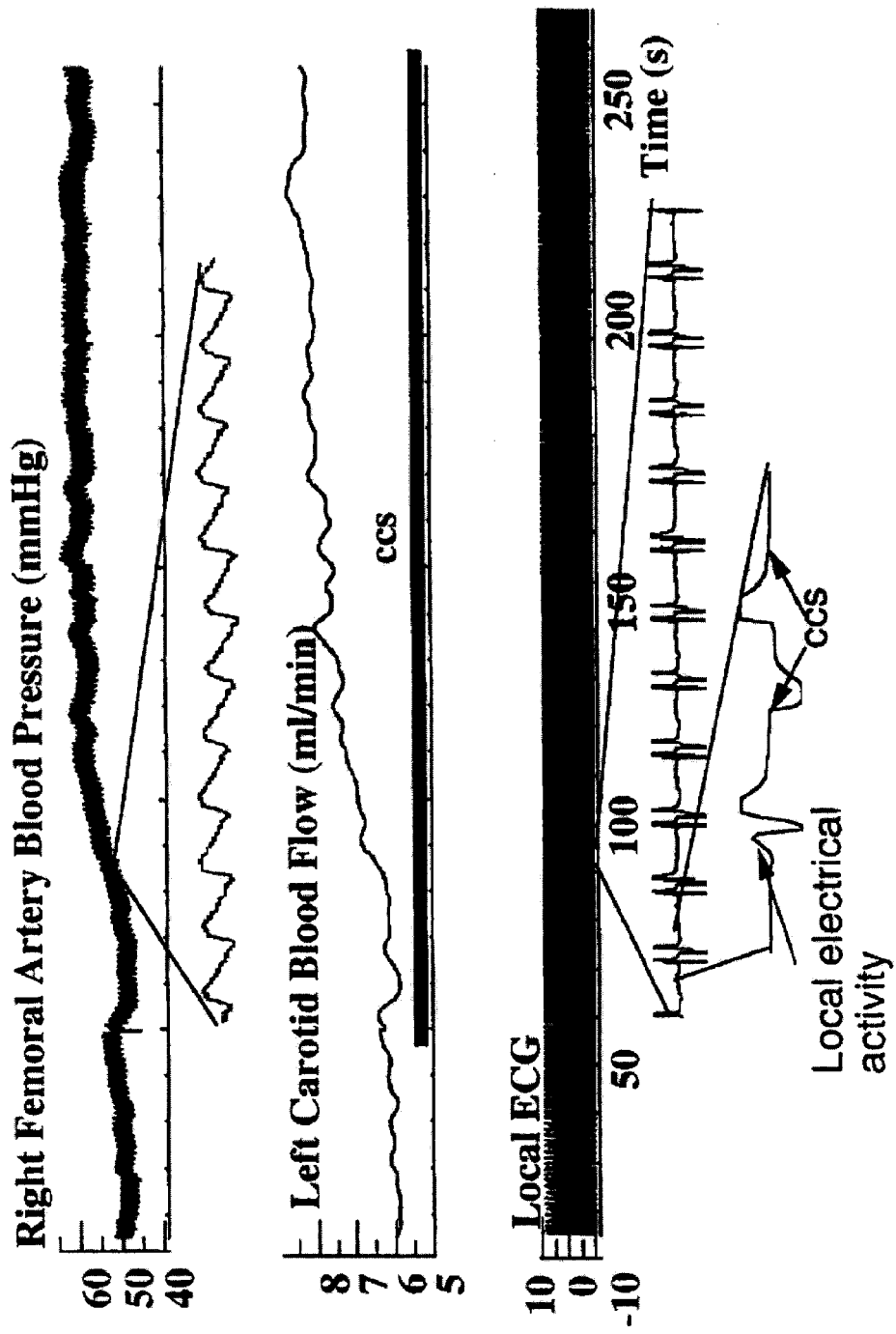

FIG. 21 shows the results of an experiment in an in-vivo heart in which the heart was not paced. It is similar to the experiments of FIGS. 19 and 20, in that blood pressure was measured in the right femoral artery and flow was measured, using an ultrasonic flowmeter, through the right carotid artery. The controlling pulse was applied using titanium-nitride electrodes, at the apex and at the base of the left ventricle. An iridium-platinum bi-polar electrode was placed at the apex of the left ventricle to sense the arrival of an activation front from the SA node of the heart. The controlling current was a 20 msec pulse, having an amplitude of 2 mA and applied 30 msec after the activation front was sensed. Increases in both the blood flow and the blood pressure were observed in this experiment.

Figure 22:
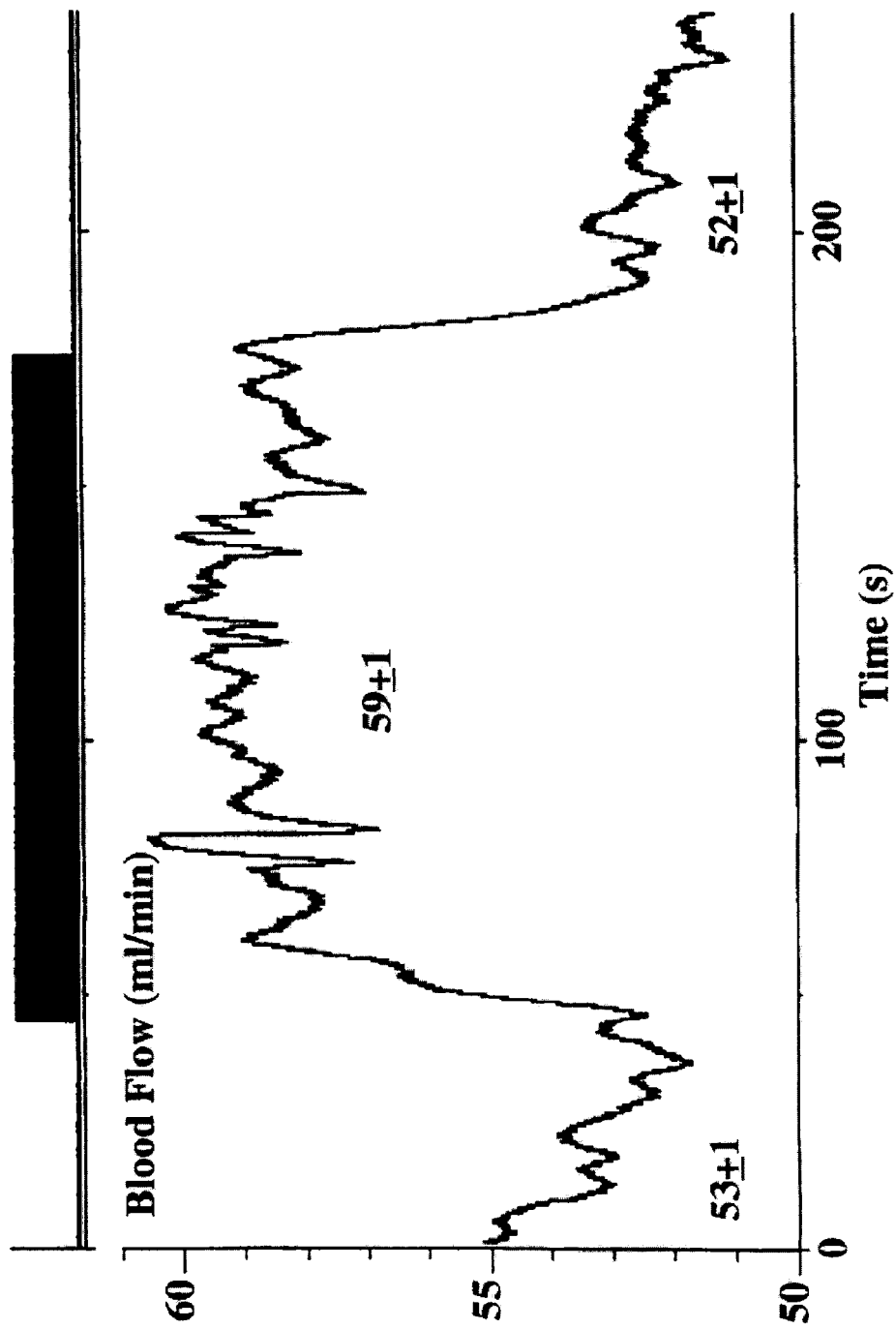
Figure 23:
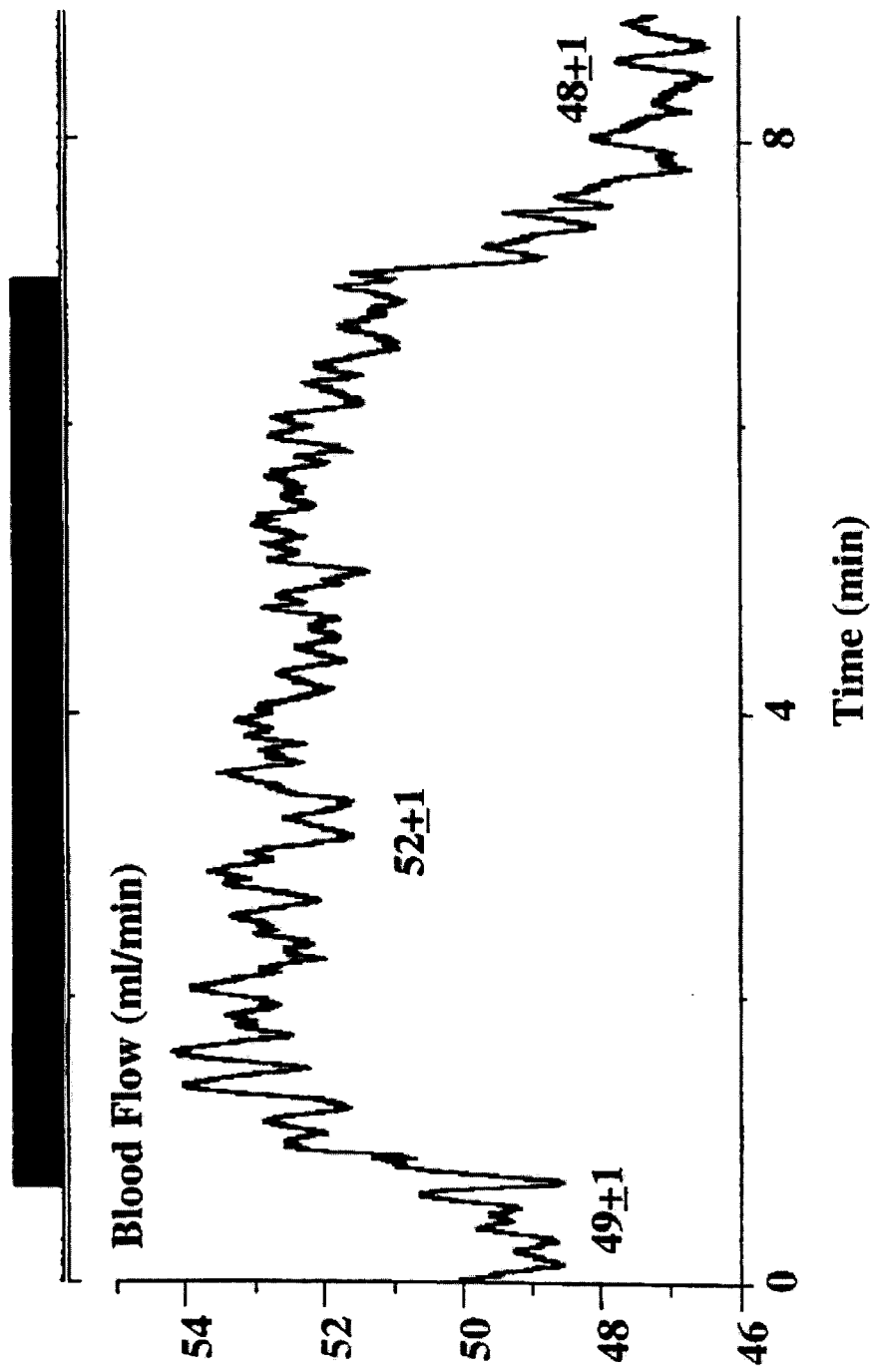

FIGS. 22 and 23 show the results of two experiments, similar to the experiment of FIG. 21, in which the flow parameter was measured on the ascending aorta. The heart of a 1.1 Kg rabbit was exposed and a sensing electrode (bipolar) was inserted, using a needle, into the apex of the heart, in accordance with an embodiment of the present invention. Two carbon electrodes were used to apply a controlling pulse to the heart, at the apex and the base of the left ventricle. The heart was not paced, it intrinsic pace was about 5 Hz. The control pulse was a 5 mA in amplitude and had a duration of 40 msec. There was no delay between the sensing of an activation front at the sensing electrodes and application of the pulse.

FIG. 22 shows an increase of about 11% in the aortic flow. FIG. 23, which shows the results of a repetition of the same experiment on the same animal at a later time, shows an increase of about 8%.

Although the present invention has been described mainly with reference to the heart, it should be appreciated that preferred embodiments of the present invention may be applied to other types of excitable tissue. In one example, skeletal muscle and smooth muscle can be controlled as described hereinabove. It should however be appreciated, that most muscles have different ion channels and different resting potentials than cardiac muscle, so that the general principles must be adapted to the individual physiology. In addition, the effects in a skeleton muscle may be due to recruitment of muscle fibers. Further, the present invention may be applied to neural tissue. For example, epileptic fits and tetanization may be controlled by damping the excitability of neural tissue, as described above. Alternatively, electrical control may be used in conjunction with electrical stimulation of denervated or atrophied muscles to increase the precision of stimulation. Additionally or alternatively, electrical control may be used to block or enhance conduction of stimuli along nervous pathways, for example, to control pain.

In a preferred embodiment of the invention, epileptic fits are controlled by suppressing Golgi cells, thus, reducing the excitability of associated neural tissues by reducing the amount of available calcium.

The above description of the present invention focuses on electrical control of cardiac tissue. However, since some aspect of the control may be related to calcium ion transport in the cardiac tissue, non-electrical control is also possible. One major advantage of non-electrical control is that even though incorrect synchronization of the control to the cardiac cycle may reduce the cardiac output, there is little or no danger of fibrillation. In one preferred embodiment of the present invention light is used to control calcium transport in portions of the heart. Laser light may be used to affect the calcium transport directly. Alternatively, a light activated chelator, which is introduced into at least some of the cells in a heart, may be activated by regular light to change the availability (increasing or reducing) of calcium in the illuminated cells. A controller in accordance with this embodiment of the invention, will include at least a light source and a light guide, preferably an optical fiber, which will convey the light to desired portions of the heart. Preferably, the optical fiber is a silicon-rubber optical fiber which is resistant to breakage. Alternatively, the controller comprises a plurality of light emitting elements, such as laser diodes, placed directly on the controlled tissue. Further alternatively, the light is provided by a catheter inserted into the heart and either floating in the heart or fixed to the heart wall. The controller preferably includes an ECG sensor for sensing local and/or global activation times, as described above.

One limitation of light over electrical current is that unless the body tissues are transparent to the particular wavelength used, light can only have a very localized effect, a global effect requires many light sources, which is invasive. One type of less invasive light source which may be useful is an optical fiber having a partially exposed sheath. Light will leak out of the fiber at the exposed portions, so a single fiber can illuminate a plurality of localities.

In an alternative embodiment of the invention, electromagnetic radiation at low and/or radio frequencies is used to affect calcium transport in the cardiac tissue. Several methods may be used to provide electromagnetic radiation. In one method, the entire heart is irradiated, preferably in synchrony with a sensed ECG of the heart. In another method, a phased array is used to aim the radiation at the heart. As noted above, the non-arrhythmic heart substantially repeats its position each cycle, so there is no problem of registration between an external source and a portion of the heart. In yet another method, an implanted device includes a plurality of antennas, each disposed adjacent to a portion of tissue to be controlled. The antennas may be powered by a central source. Alternatively, the antenna are concentrate externally applied radiation. Further alternatively, the antennas are coils which generate localized AC magnetic fields. It should be noted that electromagnetic radiation appears to be suitable for reducing calcium availability, which makes it suitable for reducing the oxygen demands of an infarcted tissue after a heart attack. In embodiments using electromagnetic-radiation as in light and electric current, there may be a long term reduction in the effectiveness of the controller due to adaptation mechanisms of the heart. Thus, in a preferred embodiment of the invention, the controller is not used continuously, with preferred rest periods between uses, being minutes, hours, days or weeks depending on the adaptation of the heart.

In a preferred embodiment of the invention, two or more control modalities are applied simultaneously, for example, applying both light radiation and electric fields. Alternatively, these modalities may be applied alternately, so as to cope with adaptation mechanisms. Preferably, each modality is applied until adaptation sets in, at which point the modality is switched.

Although the present invention has been described using a limited number of preferred embodiments, it should be appreciated that it is within the scope of the invention to combine various embodiments, for example, increasing the contractility of the left ventricle, while controlling the heart rate in the right atrium. It is also in the scope of the present invention to combine limitations from various embodiments, for example, limitations of pulse duration and pulse delay relative to an activation or limitations on electrode type and electrode size. Further, although not all the methods described herein are to be construed as being performed using dedicated or programmed controllers, the scope of the invention includes controllers which perform these methods. In some cases, limitations of preferred embodiments have been described using structural or functional language for clarity, however, the scope of the invention includes applying these limitations to both apparatus and methods.

Figure 25:
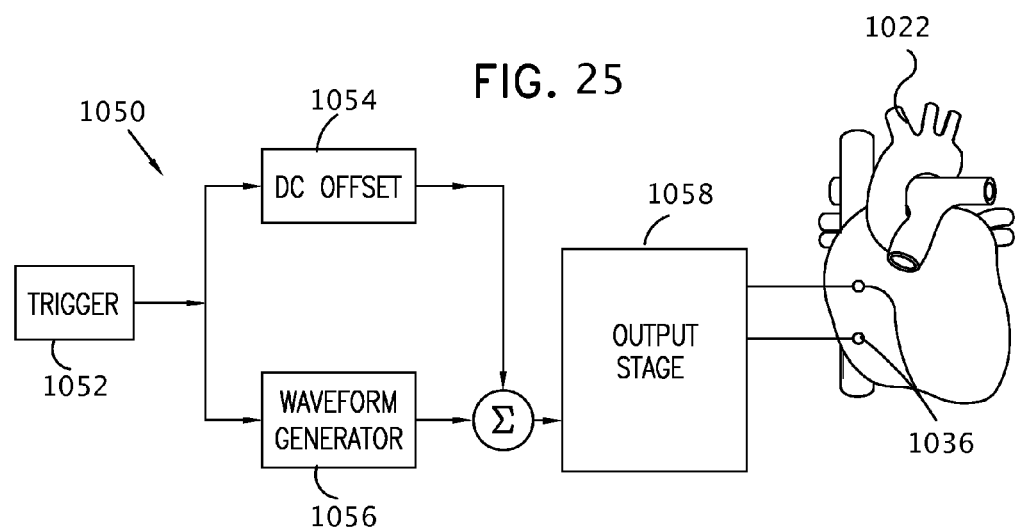
FIG. 25 is a schematic block diagram illustrating a pulse train generator for applying extended pacing signals to a heart, in accordance with a preferred embodiment of the present invention.

Reference is now made to FIG. 25, which is a schematic block diagram illustrating a pulse train generator 1050, which generates and applies extended pacing signals to heart 1022 via electrodes 1036, in accordance with a preferred embodiment of the present invention. Generator 1050 is preferably used as part of a complete pacing system (shown below in FIGS. 29A an 29B), but it has also been used by the inventors in experimental assessment of the principles of the present invention, as described hereinbelow with reference to FIGS. 27 and 28.

Generator 1050 comprises a waveform generator 1056 and, preferably, a DC offset generator 1054, which are synchronized by a trigger generator 1052. The outputs of the waveform and DC offset generators are summed and input to an output stage 1058, which preferably comprises a voltage output stage or, alternatively, a voltage-to-current converter. Trigger generator 1052, waveform generator 1056, DC offset generator 1054 and output stage 1058 comprise electrical elements that are known in the pacemaking art, but are suitably modified to provide relatively longer pulses and higher energy levels.

FIG. 26A is a timing diagram illustrating an extended signal 1060 applied by generator 1050 to electrodes 1036, in accordance with a preferred embodiment of the present invention. The signal preferably comprises a train of biphasic pulses, having an overall duration $T_5$, which is preferably at least three times the chronaxie time, and is most preferably at least 10 ms and no more than about 100 ms. Preferably, the signal begins with an initial cathodic pulse 1062, and has a period $T_4$ which is most preferably approximately 20 ms, but may be either longer or shorter. The signal peak-to-peak amplitude is preferably at least three times the threshold, unlike pacemakers known in the art, which generally operate at no more than twice the pacing threshold. Although signal 1060 is shown as having a duty cycle of approximately 50%, a lower duty cycle is also possible, preferably as low as 10% in order to reduce energy expenditure. When a low duty cycle is used, initial pulse 1062 may itself have a duration as short as 1 ms, or even less. Various other possible extended pacing signals, in accordance with preferred embodiments of the present invention, are shown and described hereinbelow.

Signal 1060 is shown in FIG. 26A as comprising a periodic train of three biphasic (cathodic plus anodic) square wave pulses, as signals comprising two or more biphasic pulses have been found to give the greatest relative increase in cardiac output, by comparison with ordinary pacing pulses known in the art. The pulse train preferably has a repetition frequency between 50 and 200 Hz (period between 5 and 20 ms), for maximal enhancement of hemodynamic function, and is superimposed on a DC offset. Other signals may also be used, however, for example:

a single extended pulse, either cathodic or anodic;

one or more biphasic pulses that begin with an anodic pulse, rather than with the cathodic pulse as shown in the figure;

a train of uniphasic pulses, either cathodic or anodic;

a train of pulses having non-square shape, such as sinusoidal pulses; or a pulse train including more or fewer pulses than are shown in the figure.

Furthermore, pulses in the train may have a substantially uniform amplitude, or the pulse amplitudes may vary according to a predetermined envelope function.

An essential feature of signal 1060 is its long overall duration $T_5$, which must be substantially greater than the duration of pacing pulses commonly used in the art. Preferably, the period of the signal, $T_4$, is itself also substantially longer than ordinary pacing pulses. As noted hereinabove, in order to generate action potentials in the heart, pacing pulses need have a duration of no more than 1-2 ms, whereas $T_4$ is several times that long, and $T_5$ is many times longer. Therefore, only a small, initial fraction of signal 1060 is needed for actually pacing the heart, and the remainder of the energy in the signal is applied to increase the contractility. $T_5$ is preferably kept less than about 100 ms in order to reduce or eliminate the likelihood that a later portion of signal 1060 will give rise to an additional, arrhythmic stimulation of the heart tissue.

FIG. 26B is a timing diagram showing a signal 1061 in accordance with an alternative preferred embodiment of the present invention. Signal 1061 is substantially similar to signal 1060, shown in FIG. 26A and described hereinabove, except that it has a relatively long, smoothly-decaying trailing edge 1064. Preferably, the decay of edge 1064 is generally exponential. Because of the slow decay of edge 1064, the magnitude of the rate of change of the voltage (dV/dt) applied to heart 1022 by electrodes 1036 in this portion of the signal will be relatively small, by comparison with the sharp trailing edge of signal 1060. Therefore, the likelihood of an undesired, arrhythmic stimulation due dV/dt of the trailing edge is substantially reduced when signal 1061 is used.

Figure 27:
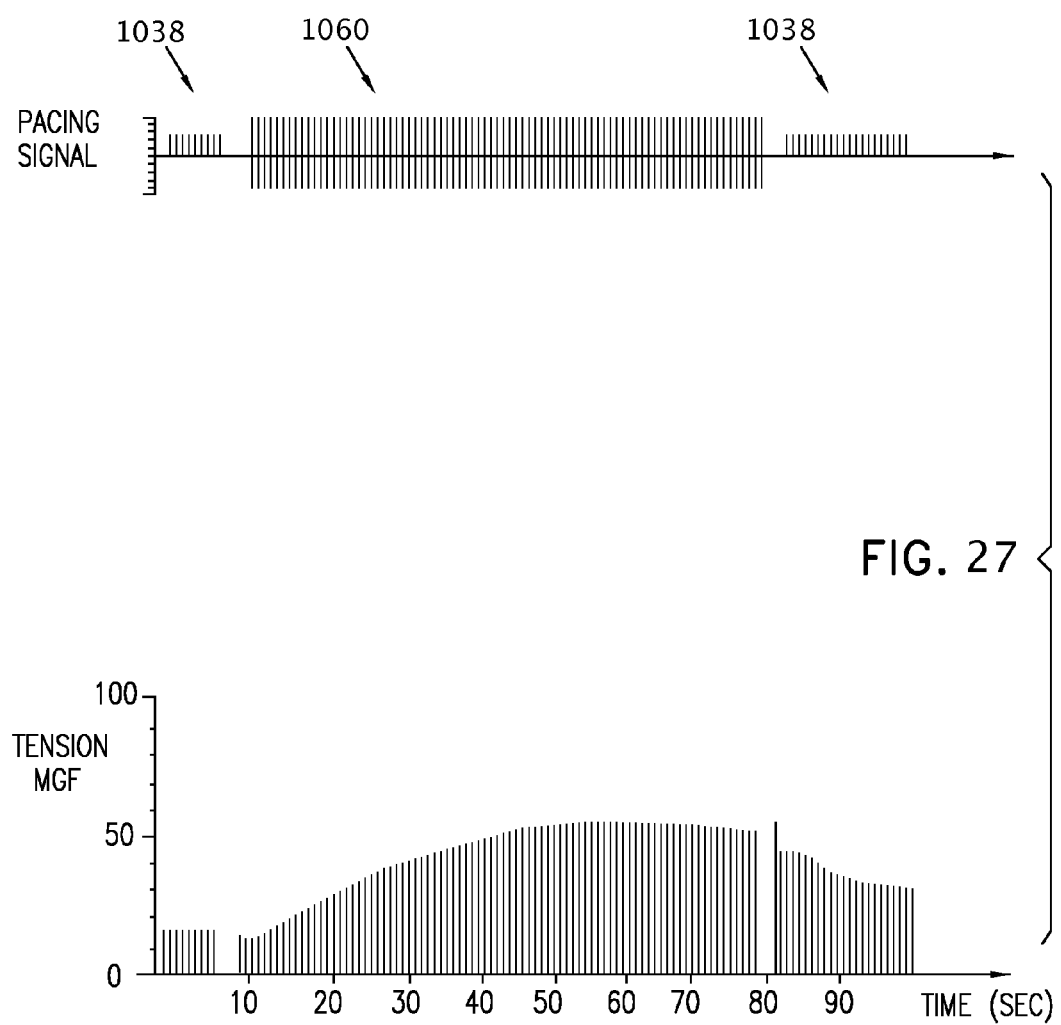
FIG. 27 is a graph that schematically illustrates experimental results showing increased muscular tension obtained upon application of extended pacing signals to muscle fibers, in accordance with a preferred embodiment of the present invention.

FIG. 27 is a graph showing experimental measurements of muscular tension as a result of pacing with extended pacing signals, in accordance with a preferred embodiment of the present invention. Carbon electrodes were fixed to a rabbit right papillary muscle, which was paced at 1 Hz. A muscle tendon was hooked onto a force transducer (D-7806 DC Bridge Amplifier, with ±10 gram input range, produced by Hugo Sachs Electronics, Germany). The muscle was hooked at an optimal muscle length for enabling isometric contraction measurements. The tension was monitored and recorded at a rate of 1000 Hz per channel, with A/D resolution of 12 bits.

Figure 24A:
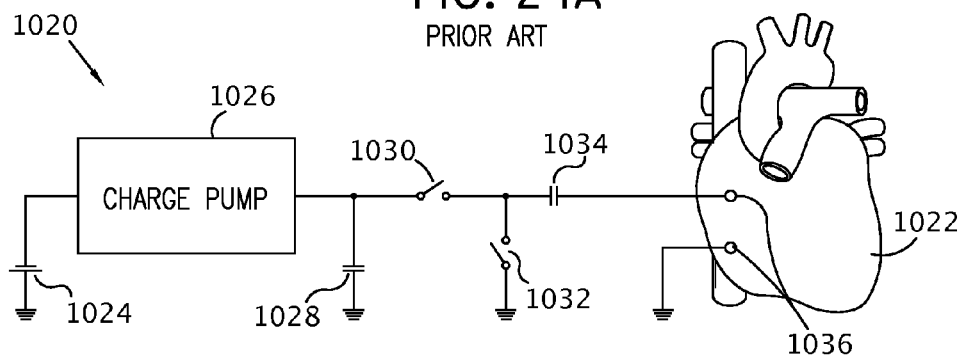
FIG. 24A is a schematic electrical diagram of a pacemaker pulse generator, as is known in the art.
Figure 24B:
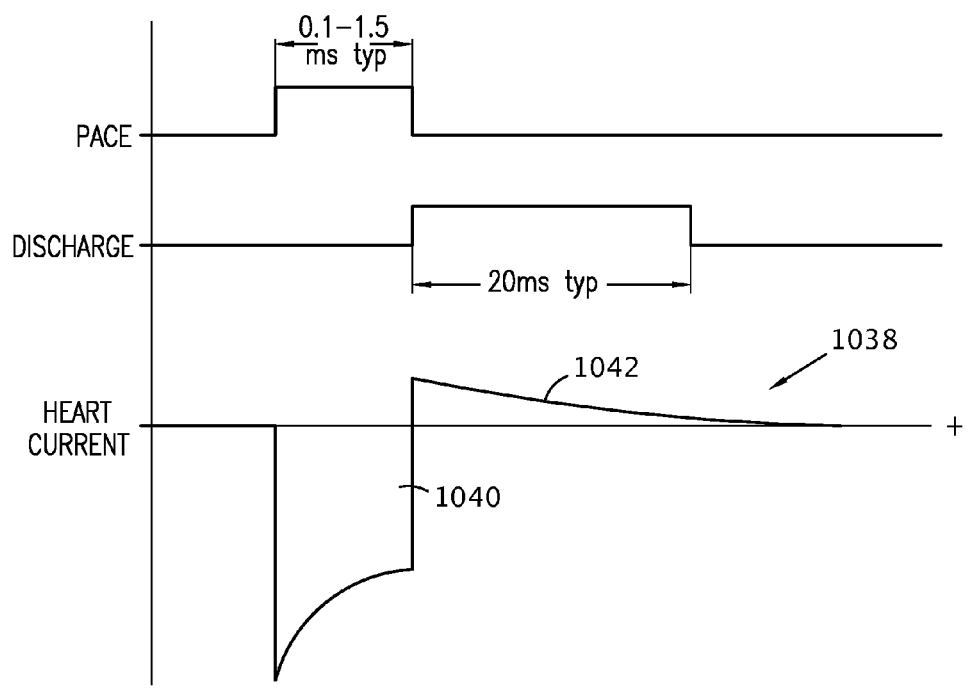
FIG. 24B is a timing diagram illustrating signals associated with the pacemaker of FIG. 24A.

Initially, the muscle was paced with a conventional pacing signal, such as waveform 1038 (FIG. 24B). An extended signal similar to signal 1060, was then applied, having a period $T_4$=10 ms and duration $T_5$=60 ms and a peak-to-peak amplitude of 6 mA. The tension of the muscle was observed to increase gradually over a period of 30-40 sec, until it leveled off at about 3-4 times its initial value, which was measured under conventional pacing. When the extended signal was discontinued, and conventional pacing resumed, the tension dropped gradually back to its previous value.

Figure 28:
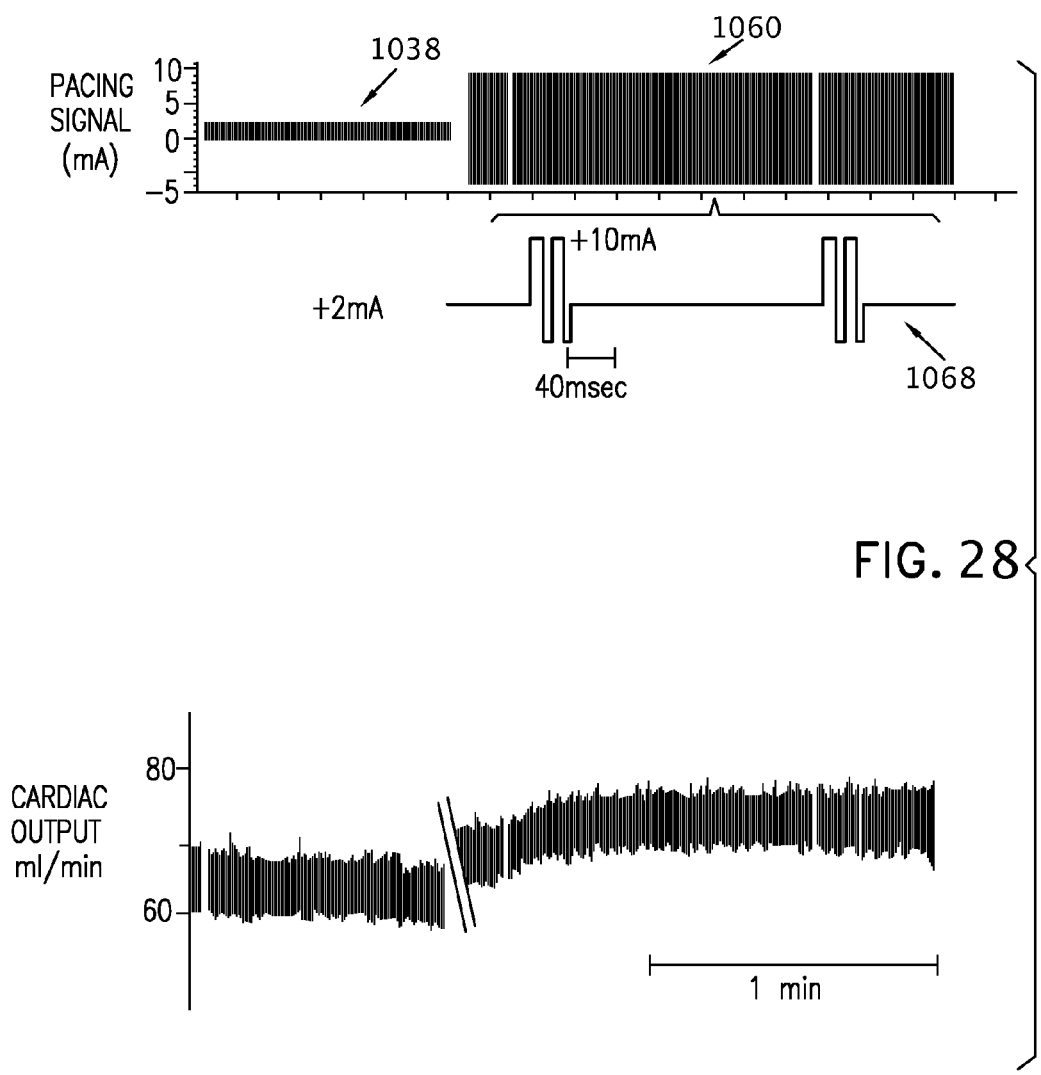
FIG. 28 is a graph that schematically illustrates experimental results showing an enhancement of cardiac output due to application of extended pacing signals, in accordance with a preferred embodiment of the present invention.

FIG. 28 is a graph showing further experimental results, illustrating an increase in cardiac output due to pacing with extended pacing pulses, in accordance with a preferred embodiment of the present invention. A rabbit heart was dissected out and perfused with a balanced isotonic solution, using the Langerdorff working heart apparatus, under standard experimental conditions known in the art. Two graphite vacuum electrodes were epicardially positioned at the left ventricle of the heart, and the pacing signal shown at the top of FIG. 28 was applied between the electrodes. Initially, with a conventional pacing signal such as waveform 1038, mean cardiac output was measured to be 65 ml/min. An extended signal similar to signal 1060 was then applied, and the cardiac output was observed to rise gradually to about 75 ml/min, which was maintained for as long as the extended signal was applied, a period of 2 min. In this case, as shown by an inset 1068 in FIG. 28, the extended signal comprises two biphasic pulses, each beginning with an anodic pulse having an amplitude of about 10 mA, followed by a cathodic pulse of about 6 mA, with a DC level of about ±2 mA. The overall signal duration $T_5$ was about 40 ms. Since the heart rate was held constant, at 180 beats/min, the increase in cardiac output was attributable to an increase in the heart's stroke volume.

Figure 29A:
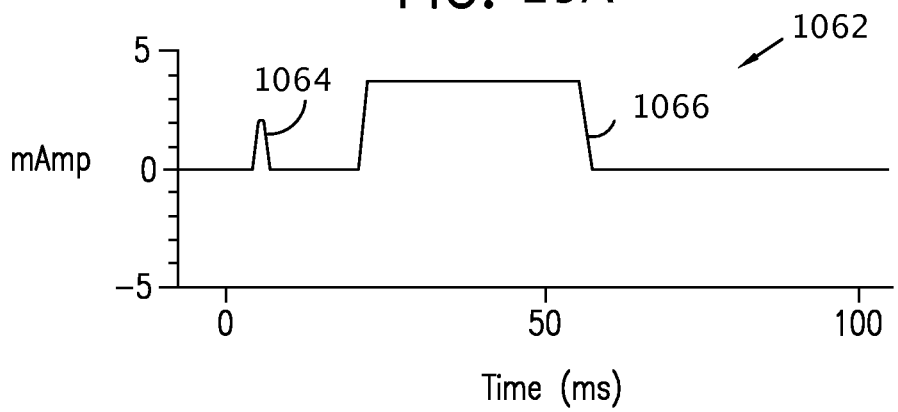
FIG. 29A is a graph that schematically illustrates an extended pacing signal, in accordance with another preferred embodiment of the present invention.

FIG. 29A schematically illustrates another extended pacing signal 1062, in accordance with a preferred embodiment of the present invention. Signal 1062 comprises a train of two anodic pulses: an initial, relatively short pulse 1064, approximately 2 ms long and has an amplitude of 2 mA, followed by a longer pulse 1066 having a duration of 30-40 ms and variable amplitude.

Figure 29B:
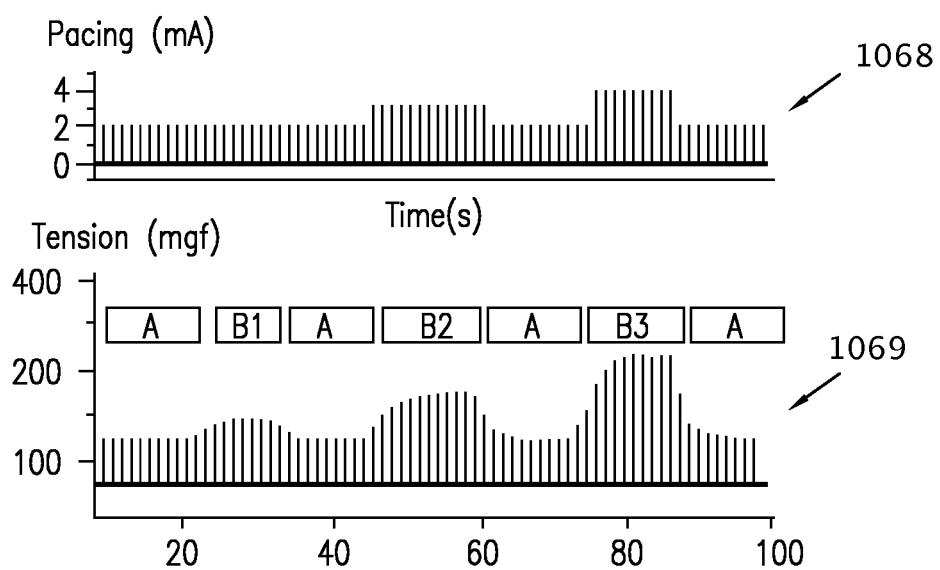
FIG. 29B is a graph that schematically illustrates experimental results obtained using pacing signals of the form shown in FIG. 29A.

FIG. 29B shows experimental measurements of changes in muscle tension due to application of signal 1062, in which the amplitude of pulse 1066 was varied, in accordance with a preferred embodiment of the present invention. In this figure, an upper trace 1068 shows the applied pacing signal, and a lower trace 1069 shows the muscle tension measurement. A rabbit right papillary muscle was placed in an organ bath and perfused continuously with Krebs solution at 37° C. The muscle was stretched to an optimal length (Lmax), and its isometric tension was sampled at 1000 Hz. The muscle was paced unipolarly by applying signal 1062 through a Teflon-coated platinum-iridium wire (0.125 mm diameter) at 1 Hz, against two reference electrodes (uncoated graphite, 0.9 mm diameter) at either end of the bath.

Pacing of the muscle was divided into several periods, labeled in FIG. 29B, during which the amplitude of pulse 1066 was set to different values, as given by Table I, below:

TABLE I

| Period | Amplitude of pulse 1066 |
| --- | --- |
| A (control) | Zero |
| B1 | 2 mA |
| B2 | 3 mA |
| B3 | 4 mA |

As can be seen in FIG. 29B, the muscle tension increased strongly, nearly doubling from its control level (A) to that obtained during period B3.

Figure 30:
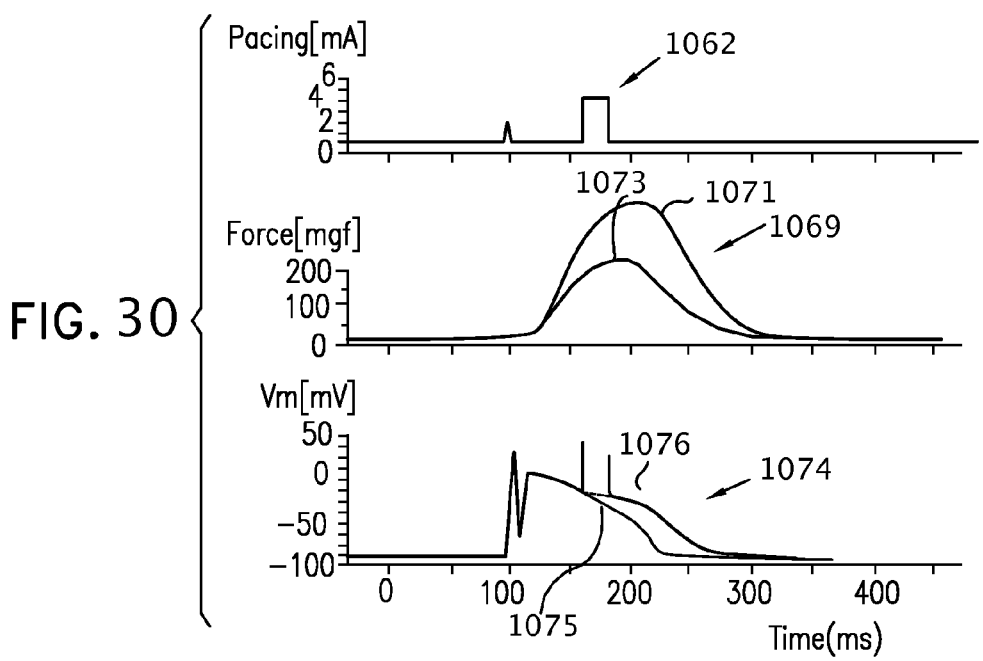
FIG. 30 is a graph schematically illustrating modulation of contraction force and action potentials using the pacing signal of FIG. 29A.

FIG. 30 schematically illustrates further experimental results obtained using pacing signal 1062, in accordance with a preferred embodiment of the present invention. Trace 1069 in FIG. 30 illustrates a detail of the force measurements shown in FIG. 29B, wherein a pressure wave 1071 obtained during period B3 is seen to be substantially higher and longer than a corresponding wave 1073 measured under conventional pacing during the control period.

Trace 1074 in FIG. 30 shows measurements of action potentials obtained under the conditions described with reference to FIG. 29B. An ordinary potential 1075 obtained during the control period has a duration of about 100 ms. During period B3, however, a lengthened action potential 1076 is obtained, having a duration of about 150 ms. (An initial portion of potential 1076 overlaps in shape and amplitude with potential 1075 and is therefore indistinguishable from it in the figure.) Similar lengthening of the action potentials, relative to those measured under conventional pacing, has also been observed to occur when other types of extended pacing signals are applied, in accordance with the principles of the present invention.

By comparison, in the article by Thakor et al., mentioned above, action potentials were observed to propagate faster through the tissue, but no extension of their duration was reported. Furthermore, although Thakor observed slightly increased pressure and faster pressure onset in isolated muscle fibers, he did not measure or report an increase in cardiac output, as the present invention has been shown to engender. The range of signal durations (2-8 ms) and the total energy applied to the heart in Thakor's experiments were both roughly an order of magnitude less than corresponding values in preferred embodiments of the present invention, as described hereinabove. The enhancement of cardiac output observed by the present inventors due to the use of extended pacing signals, and the pacing methods and pacemaker apparatus based thereon, are therefore believed to be substantively different from those reported by Thakor or by other investigators and to represent a more advantageous form of therapy.

Figure 31:
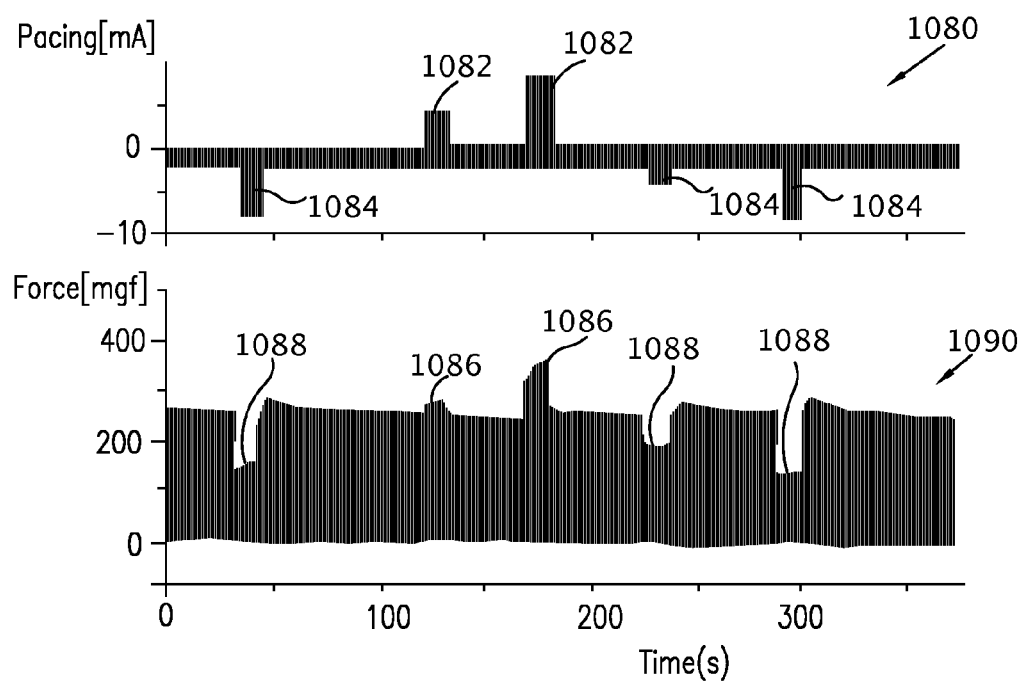
FIG. 31 is a graph schematically showing further experimental results, in accordance with a preferred embodiment of the present invention.

FIG. 31 is a graph that schematically illustrates further experimental results, in accordance with a preferred embodiment of the present invention, in which extended pacing signals are used alternatively to increase and to decrease muscular force. Decreasing the muscular force may be useful under some clinical conditions in order to reduce local strain on the heart muscle and to engender a redistribution of the heart's work load among different areas of the heart.

An upper trace 1080 in FIG. 31 shows unipolar pacing signals applied to the heart, wherein positive peaks 1082 indicate application of anodic extended pacing signals, and negative peaks 1084 indicate cathodic extended pacing signals. The extended pacing signals have the general form of signal 1062, shown in FIG. 29A, except that the cathodic signals are inverted. The remainder of trace 1080, other than the peaks, represents conventional pacing.

A lower trace 1090 in the figure shows measurements of tension made under the general conditions described above with reference to FIG. 29B. The anodic extended pacing signals engendered increased contractile force of the muscle, whereas the cathodic extended pacing signals had the opposite effect. The magnitude of the increase or decrease was generally proportional to the amplitude of pulse 1066.

Figure 32:
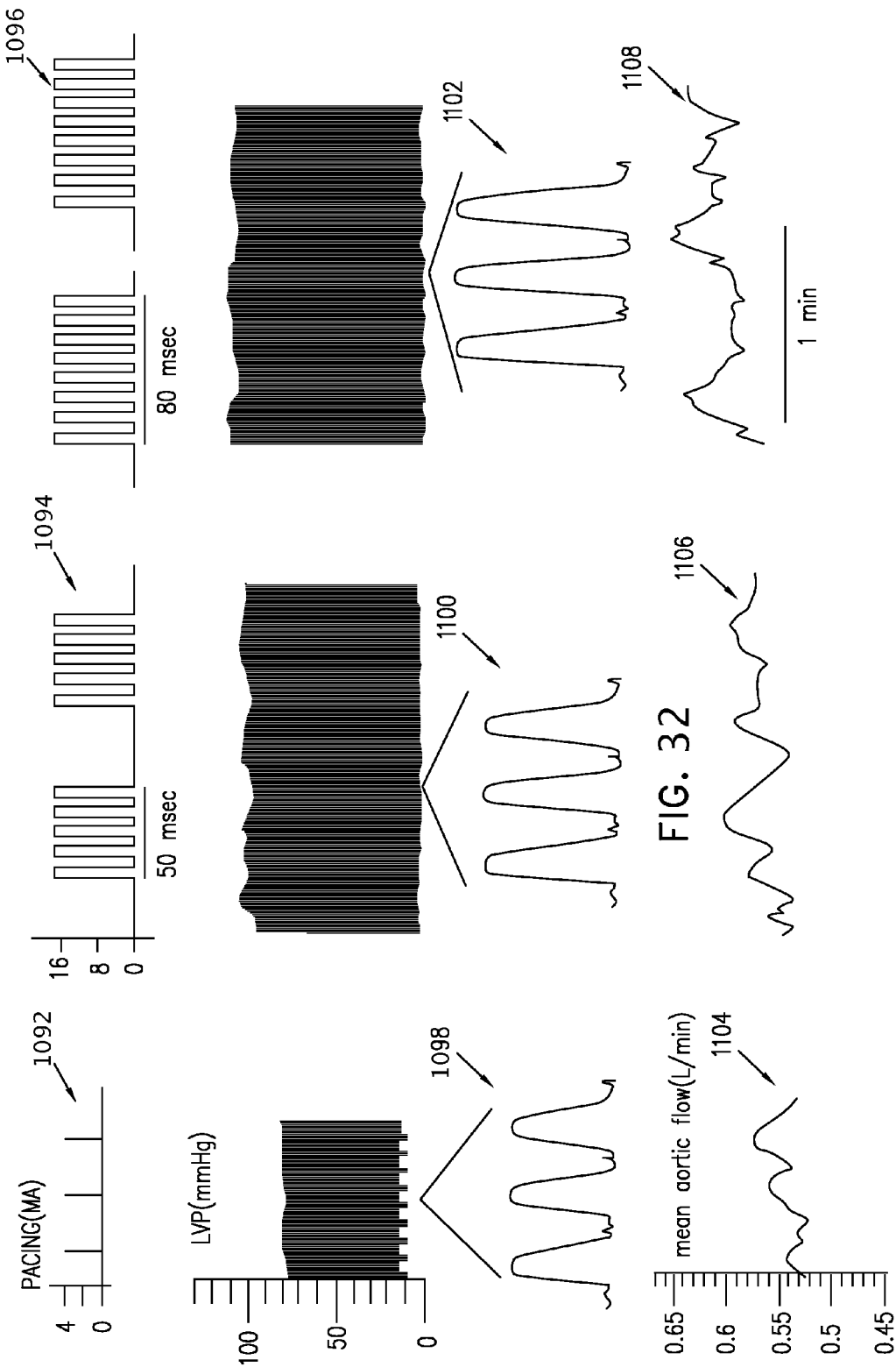
FIG. 32 is a graph that schematically shows enhancement of ventricular pressure and aortic flow due to application of extended pacing signals, in accordance with another preferred embodiment of the present invention.

FIG. 32 schematically illustrates further experimental results, showing the influence of extended pacing signals 1094 and 1096 in enhancing the heart's pulsatile flow, in accordance with a preferred embodiment of the present invention. In these experiments, a 27 kg dog was anesthetized with chloralose-urethane, intubated to the trachea and mechanically ventilated. After chest surgery, the dog's pericardium was opened, and carbon electrodes were placed epicardially at the right and left ventricles. A conventional pacing signal 1092, of 4 mA amplitude and 2 ms duration, was applied (VOO mode) as a control at the right ventricle. Signal 1092 was replaced for two-minute intervals with either signal 1094 or 1096, applied at the left ventricle. Signals 1094 and 1096 comprised anodic pulse trains having repetition frequencies of 100 Hz and amplitudes of 16 mA with respective overall durations of 50 and 80 ms.

In measurements of the dog's left ventricular pressure (LVP), it was observed that pacing with signal 1096 caused the peak pressure to increase by 34-36% relative to the LVP under conventional pacing signal 1092. Signal 1094 caused a somewhat smaller pressure increase. The positive impact of the extended pacing signals on the heart's pulsatile flow is demonstrated by the increased amplitude of pressure waveforms 1100 and 1102, obtained when the extended pacing signals were used, relative to that of waveform 1098 with conventional pacing. Furthermore, the mean aortic flow from the heart was observed to increase due to the extended pacing signals, up to about 12-13% more than the flow obtained under conventional pacing conditions.

FIG. 33 is a schematic block diagram showing a pacemaker 1170 for application of extended pacing pulses via electrodes 1136 to heart 1122 of a patient, for the purpose of enhancing the contractility of the heart, in accordance with a preferred embodiment of the present invention. Pacemaker 1170 is generally similar to implantable pacemakers known in the art, except that it is built around pulse train generator 1150, as described hereinabove, and is programmed to apply extended pacing signals. Such signals may be applied substantially continuously, or they may be applied only as needed, for example, at certain hours of the day or upon demand by the patient, when the patient needs a boost in cardiac output.

Although electrodes 1136 are shown only schematically in FIG. 33, it will be appreciated that a variety of different numbers and placements of the electrodes may be used. For example, pacemaker 1170 may be coupled to drive more than two electrodes, which may be placed either in the same chamber or in multiple different chambers of the heart. The extended pacing signal, such as signal 1060 (FIG. 26A) or signal 1061 (FIG. 26B), may be applied to electrodes 1136 in either unipolar or bipolar fashion. The electrodes are preferably placed endocardially, but may alternatively be placed epicardially, within a blood vessel, intramuscularly or in any other suitable location. The electrodes may be aligned along a normal conduction direction in the heart or perpendicular to the normal conduction direction. Preferably, the electrodes are placed in the heart responsive to a map of the heart's electrical and/or mechanical activity, in positions chosen so as to give a desired change in contraction of the heart muscle or, alternatively or additionally, to engender a desired redistribution of cardiac muscle mass. The electrodes preferably comprise highly conductive material with a large effective area, and are most preferably coated with a high-capacitance material, such as titanium nitride, iridium oxide, pyro-carbon or vitreous carbon.

In a preferred embodiment of the present invention, when more than two electrodes are used, the signals applied respectively to the electrodes are mutually timed so as to optimize the heart's systolic contraction. For example, one or more electrodes may be placed in one of the atria of the heart, and another one or more in the corresponding ventricle, in which case the signal is preferably applied first to the atrial electrodes. Alternatively, a conventional, low-energy pacing pulse may be applied to the atrial electrodes and an extended pacing signal applied after a delay to those in the ventricle. Similarly, electrodes may be applied in both right and left ventricles, with stimulation preferably applied first in the right ventricle. In any case, the signals are applied to the electrodes in such order and timing as to optimize hemodynamic performance.

Pacemaker 1170 comprises a microprocessor 1176, which is coupled to timer circuits 1172 and memory 1174 (RAM and/or ROM) and controls the operation of generator 1150. The microprocessor and ancillary timer and memory circuits are substantially similar to such circuits and devices as are known in the pacemaking art. They differ from the prior art largely in that they are programmed to administer extended pacing signals, as described hereinabove, either instead of or in addition to conventional pacing signals. A sense amplifier 1178, as is similarly known in the art, receives and amplifies electrogram signals from electrodes 1136. These signals are conveyed to microprocessor 1176, which preferably regulates the operation of generator 1150 responsive to the signals.

A key purpose of sense amplifier 1178 is to inhibit the delivery of the extended pacing signal at the time of the heart chamber's repolarization, so as to prevent undesired, arrhythmic stimulation of the heart. In a preferred embodiment of the present invention, one or more of electrodes 1136 are used in Monophasic Action Potential (MAP) measurements of the heart's electrical activity, as are known in the art and described in the above-mentioned articles by Franz. To perform these measurements, a fixed potential is created, for example, by applying pressure at a location in the endocardium, and a unipolar action potential is measured by one or more of the electrodes relative to the fixed potential. Because the MAP measurements determine the action potential locally, the effect of "far-field" cardiac potentials is substantially reduced or eliminated. Such measurements can therefore be used to accurately monitor repolarization and sense local variations that may arise due to the extended pacing signal.

In another preferred embodiment, two of electrodes 1136 are placed close together and used to capture electrophysiological signals using close bipolar sensing. A differential signal measured between the two electrodes reflects propagation of the action potentials in a small area, having dimensions on the order of the distance between the electrodes. The differential signal is thus used to determine the time of onset and the duration of the local action potential at the location of the electrode and to accurately observe changes in the action potential due to application of the extended pacing signals. As described above, microprocessor 1176 preferably controls the extended pacing signal so that the pacing signal duration does not exceed that of the refractory period and discontinues the extended pacing signals if abnormal local electrical activity is observed to result from the pacing.

Thus, based on signals from amplifier 1178, microprocessor 1176 preferably detects a change in the local action potential indicative of a possible arrhythmic excitation of the heart due the signal, using the MAP measurement and/or other electrical parameters. When such a change is detected, the microprocessor limits the pacing signal duration accordingly, so as substantially not to exceed the length of the refractory period and avoid undesirable, arrhythmic stimulation. In addition, microprocessor 1176 may be programmed so that pacemaker 1170 functions as a rate-responsive pacemaker, introducing pacing pulses to electrodes 1136 in response to detection of bradycardia, for example, or to other heart rate changes or arrhythmias, as is known in the art.

Preferably, a sensor 1180 is coupled to heart 1136 or elsewhere to the body of the patient, and provides an additional physiological input to microprocessor 1176. Sensor 1180 may comprise any suitable physiological sensor, or a plurality of sensors, known in the art. In particular, sensor 1180 preferably comprises a stroke volume sensor or contractility sensor, such as a sensor based on intracardiac impedance measurement, as is known in the art, or alternatively or additionally, an oxygen sensor or pressure sensor. The sensor may then be used as part of a feedback loop, wherein microprocessor 1176 controls the waveform generated by pulse train generator 1150 in order to achieve and maintain a desired level of cardiac output.

Further preferably, microprocessor 1176 is coupled by a wireless link, as is known in the art, to a telemetry system 1182. This system is used in programming the microprocessor initially and in monitoring and adjusting its performance in later follow-up examinations of the patient.

As noted above, pacemaker 1170 is preferably implanted in the patient's chest. It therefore preferably receives its power from a battery 1184, which is suitably coupled to microprocessor 1176, pulse train generator 1150 and other power-consuming components. Because generator 1150 applies substantially more energy to heart 1122 than do pacemakers known in the art, the power drain on battery 1184 is substantially higher. Therefore, battery 1184 preferably comprises a rechargeable battery, for example, a lithium ion solid electrolyte type battery, as is known in the art. Periodically, battery 1184 is recharged using a charger 1186, which preferably charges the battery without forming a wired connection therewith, most preferably by inductive coupling of energy, as is generally known in the art.

It will be appreciated that the preferred embodiments described above are cited by way of example, and the full scope of the invention is limited only by the claims.

For some applications, techniques described herein are practiced in combination with techniques described in one or more of the references cited in the Cross-references section or the Background section of the present patent application, which are incorporated herein by reference.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus comprising: sensing circuitry configured for sensing electrical activity of a muscle segment of a heart; one or more implantable electrodes, wherein said electrodes are adapted to convey an electrical signal to the muscle segment of the heart; and pacing circuitry for pacing the heart, wherein said pacing circuitry is adapted to drive the electrodes to apply the signal to the segment by driving an electrical current into the segment, the current having an amplitude of at least 3 mA and less than 20 mA, and a signal duration, in a cardiac cycle, of between 10 and 140 msec, wherein the signal is applied in response to the sensing with a delay relative to the preceding sensed electrical activity.

2. The apparatus according to claim 1, wherein the amplitude of the current is less than 8 mA.

3. The apparatus according to claim 2, wherein the amplitude of the current is less than 5 mA.

4. The apparatus according to claim 1, wherein the duration is between 20 and 100 msec.

5. The apparatus according to claim 1, wherein the pacing circuitry is configured to apply the current with a strength of between 50 and 500 micro joules.

6. The apparatus according to claim 1, wherein the pacing circuitry is configured to drive the current into a left ventricle.

7. The apparatus according to claim 1, wherein the pacing circuitry is configured to drive the current into a right ventricle.

8. The apparatus according to claim 1, wherein the pacing circuitry is configured to drive the current into a left atrium.

9. The apparatus according to claim 1, wherein the pacing circuitry is configured to drive the current into a right atrium.

10. The apparatus according to claim 1, wherein the pacing circuitry is configured to apply the signal as a constant amplitude pulse.

11. The apparatus according to claim 1, wherein the pacing circuitry is configured to apply the signal as a biphasic pulse form.

12. The apparatus according to claim 1, wherein the pacing circuitry is configured to apply the current as an AC electric field.

13. The apparatus according to claim 1, wherein the pacing circuitry is configured to apply the signal as a train of pulses.

14. The apparatus according to claim 1, wherein the pacing circuitry is configured to apply the signal only once every number of heart beats.

15. The apparatus according to claim 1, wherein the pacing circuitry configures the signal to not disrupt regular activation of the heart.

16. The apparatus according to claim 1, wherein the pacing circuitry is configured to apply the signal in a substantial number of cardiac cycles.

17. A method comprising; sensing electrical activity of a muscle segment of a heart; implanting one or more electrodes in a subject; and driving, by pacing circuitry for pacing a heart of the subject, the electrodes to apply an electrical signal to a muscle segment of the heart by driving an electrical current into the segment, the current having an amplitude of at least 3 mA and less than 20 mA, and a signal duration, in a cardiac cycle, of between 10 and 140 msec, wherein the signal is applied in response to the sensing with a delay relative to the preceding sensed electrical activity.

18. The method according to claim 17, wherein the amplitude of the current is less than 8 mA.

19. The method according to claim 18, wherein the amplitude of the current is less than 5 mA.

20. The method according to claim 17, wherein the duration is between 20 and 100 msec.

21. The method according to claim 17, wherein driving comprises driving the electrodes to apply the current with a strength of between 50 and 500 micro joules.

22. The method according to claim 17, wherein driving comprises driving the current into a left ventricle.

23. The method according to claim 17, wherein driving comprises driving the current into a right ventricle.

24. The method according to claim 17, wherein driving comprises driving the current into a left atrium.

25. The method according to claim 17, wherein driving comprises driving the current into a right atrium.

26. The method according to claim 17, wherein driving comprises driving the electrodes to apply the signal as a constant amplitude pulse.

27. The method according to claim 17, wherein driving comprises driving the electrodes to apply the signal as a biphasic pulse form.

28. The method according to claim 17, wherein driving comprises driving the electrodes to apply the current as an AC electric field.

29. The method according to claim 17, wherein driving comprises driving the electrodes to apply the signal as a train of pulses.

30. The method according to claim 17, wherein driving comprises driving the electrodes to apply only once every number of heart beats.

31. The method according to claim 17, wherein driving comprises configuring the signal to not disrupt regular activation of the heart.

32. The method according to claim 17, wherein driving comprises driving the electrodes to apply the signal in a substantial number of cardiac cycles.

33. The apparatus according to claim 1, wherein said pacing circuitry is configured to pace a heart as a replacement or assistance for natural pacing.

34. The apparatus according to claim 1, wherein said apparatus includes a battery and is implantable.

* * * * *